US009867807B2

(12) United States Patent
Sacchettini et al.

(10) Patent No.: US 9,867,807 B2
(45) Date of Patent: *Jan. 16, 2018

(54) COMPOSITIONS AND METHODS FOR DRUG-SENSITIZATION OR INHIBITION OF A CANCER CELL

(71) Applicant: The Texas A&M University System, College Station, TX (US)

(72) Inventors: James Sacchettini, College Station, TX (US); Niam Zhou, College Station, TX (US); Dwight Baker, College Station, TX (US); Steven A. Maxwell, College Station, TX (US); Deeann Wallis, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/362,272

(22) Filed: Nov. 28, 2016

(65) Prior Publication Data

US 2017/0071905 A1  Mar. 16, 2017

Related U.S. Application Data

(63) Continuation of application No. 14/834,160, filed on Aug. 24, 2015, now Pat. No. 9,539,237, which is a continuation of application No. 14/322,727, filed on Jul. 2, 2014, now Pat. No. 9,134,329, which is a continuation of application No. PCT/US2013/057369, filed on Aug. 29, 2013.

(60) Provisional application No. 61/695,041, filed on Aug. 30, 2012, provisional application No. 61/784,416, filed on Mar. 14, 2013.

(51) Int. Cl.
| | |
|---|---|
| A61K 31/00 | (2006.01) |
| A61K 31/435 | (2006.01) |
| A61K 31/7034 | (2006.01) |
| A61K 31/395 | (2006.01) |
| A61K 45/06 | (2006.01) |
| A61K 31/122 | (2006.01) |
| A61K 31/136 | (2006.01) |
| A61K 31/337 | (2006.01) |
| A61K 31/4745 | (2006.01) |
| A61K 31/475 | (2006.01) |
| A61K 31/5377 | (2006.01) |
| A61K 31/573 | (2006.01) |
| A61K 31/675 | (2006.01) |
| A61K 31/69 | (2006.01) |
| A61K 31/704 | (2006.01) |
| A61K 31/7068 | (2006.01) |
| A61K 33/24 | (2006.01) |
| A61K 38/08 | (2006.01) |
| C07D 498/22 | (2006.01) |
| G01N 33/58 | (2006.01) |
| G01N 33/84 | (2006.01) |

(52) U.S. Cl.
CPC ......... *A61K 31/395* (2013.01); *A61K 31/122* (2013.01); *A61K 31/136* (2013.01); *A61K 31/337* (2013.01); *A61K 31/435* (2013.01); *A61K 31/475* (2013.01); *A61K 31/4745* (2013.01); *A61K 31/5377* (2013.01); *A61K 31/573* (2013.01); *A61K 31/675* (2013.01); *A61K 31/69* (2013.01); *A61K 31/704* (2013.01); *A61K 31/7068* (2013.01); *A61K 33/24* (2013.01); *A61K 38/08* (2013.01); *A61K 45/06* (2013.01); *C07D 498/22* (2013.01); *G01N 33/582* (2013.01); *G01N 33/84* (2013.01); *G01N 2800/52* (2013.01)

(58) Field of Classification Search
CPC ... A61K 31/00; A61K 31/435; A61K 31/7034
See application file for complete search history.

(56) References Cited

U.S. PATENT DOCUMENTS

| | | | |
|---|---|---|---|
| 4,086,225 | A | 4/1978 | Marsili et al. |
| 4,219,478 | A | 8/1980 | Marsili et al. |
| 7,884,099 | B2 | 2/2011 | Ding et al. |
| 2005/0203085 | A1 | 9/2005 | Li et al. |
| 2007/0225266 | A1 | 9/2007 | Barluenga Mur et al. |
| 2009/0143373 | A1 | 6/2009 | Ding et al. |

FOREIGN PATENT DOCUMENTS

| | | |
|---|---|---|
| DE | 2825445 | 6/1978 |
| IL | 54784 A | 5/1981 |
| WO | WO 2004/005298 | 1/2004 |
| WO | WO 2005/070940 | 8/2005 |
| WO | WO 2006/027397 | 3/2006 |
| WO | WO 2009/097651 | 8/2009 |
| WO | WO 2010/019511 | 2/2010 |

OTHER PUBLICATIONS

Office Action received for European Patent Application No. 13762654.5, dated Mar. 13, 2017; 5 pages.

(Continued)

*Primary Examiner* — Bruck Kifle
(74) *Attorney, Agent, or Firm* — Baker Botts L.L.P.

(57) ABSTRACT

The disclosure provides rifamycin and rifamycin derivative compositions, including rifabutin and rifabutin derivative compositions able to cause drug-sensitization in a cancer cell or inhibition of a cancer cell. The disclosure also provides methods of administering such compositions to cancer cells to sensitize them to drugs, such as chemotherapeutics, or directly inhibit them. The disclosure also provides methods of administering such compositions to increase reactive oxygen species (ROS), particularly superoxides, in cancer cells. The disclosure further provides methods of determining whether a cancer will respond to chemotherapeutics and whether to administer rifamycin or a rifamycin derivative based on ROS levels in cancer cells of a patient.

20 Claims, 50 Drawing Sheets

(15 of 50 Drawing Sheet(s) Filed in Color)

(56) References Cited

OTHER PUBLICATIONS

International Search Report and Written Opinion; PCT/US2013/057369; pp. 18, dated Feb. 13, 2014.

Bai et al.; "Blocking NF-kB and Akt by Hsp90 inhibition sensitizes Smac mimetic compound 3-induced extrinsic apoptosis pathway and results in synergistic cancer cell death"; Apoptosis, vol. 16, No. 1; pp. 16, 2011.

Barluenga et al.; "New rifabutin analogs: Synthesis and biological activity against *Mycobacterium tuberculosis*"; Bioorganic & Medicinal Chemistry Letters, vol. 16; pp. 5717-5722, 2006.

Fiqueiredo et al.; "Synthesis and evaluation of rifabutin analogs against *Mycobacterium avium* and H37Rv, MDR and NPR *Mycobacterium tuberculosis*"; Bioorganic & Medicinal Chemistry, vol. 17; pp. 503-511, 2009.

Bartolucci et al.; "21. Synthesis, Reactivity Studies, and X-Ray Crystal Structure of (11R)-25-O-Deacetyl-11-deoxo-11-hydroxy-21,23-O-isopropylidenerifamycin S"; Helvetica Chimica Acta, vol. 73; pp. 185-198, 1990.

Romagnoli et al.; "Synthesis and biological evaluation of 2-amino-3-(3',4',5'-trimethoxybenzoyl)-6-substituted-4,5,6,7-tetrahydrothienol[2,3-c]pyridine derivatives as antimitotic agents and inhibitors of tubulin polymerization"; Bioorganic & Medicinal Chemistry Letters, vol. 18, pp. 5041-5045, 2008.

Jorand-Lebrun; "Use of Triphosgene for Direct Preperation of Carbamoyl Chlorides From Tertiary Benzylamines"; Synthetic Communications, vol. 28, No. 7; pp. 1189-1195, 1998.

Santos et al.; "Structural characterization by NMR of rifabutinol, a derivative of rifabutin"; Magnetic Resonance in Chemistry, vol. 38; pp. 937-945, 2000.

Invitation to Pay Additional Fees; PCT/US2013/057369; pp. 6, dated Nov. 5, 2013.

Adamson; "Evaluation of the Antitumor Activity of Rifamycin SV"; Arch. int. Pharmacodyn; vol. 192; pp. 61-65, 1971.

Benator et al.; "Clinical evaluation of the nelfinavir-rifabutin interaction in patients with tuberculosis and human immunodeficiency virus infection"; Elsevier Science Publishers; pp. 2, 2007.

Fardel et al.; "Rifampicin Enhances Anti-Cancer Drug Accumulation and Activity in Multidrug-Resistant Cells"; Biochemical Pharmacology, vol. 49, No. 9, pp. 1255-1260, 1995.

Furusawa et al.; "Potentiation of Pirarubicin Activity in Multidrug Resistant Cells by Rifampicin"; Biol. Pharm. Bull.; vol. 20, No. 12; pp. 1303-1306, 1997.

Granzotto et al.; "Rifampicin and verapamil induced the expression of P-glycoprotein in vivo in Ehrlich ascites tumor cells"; Cancer Letters; vol. 205; pp. 107-115, 2004.

COMPOSITIONS AND METHODS FOR DRUG-SENSITIZATION OR INHIBITION OF A CANCER CELL

CROSS-REFERENCE TO RELATED APPLICATION

The present application is continuation pending U.S. patent application Ser. No. 14/834,160 filed Aug. 24, 2015; which is a continuation of U.S. patent application Ser. No. 14/322,727 filed Jul. 2, 2014, now U.S. Pat. No. 9,134,329 granted Sep. 15, 2015; which is a continuation of International Patent Application PCT/US2013/057369 filed Aug. 29, 2013; which claims priority under 35 U.S.C. §119 to U.S. Provisional Patent Application Ser. No. 61/695,041 filed Aug. 30, 2012, and to U.S. Provisional Patent Application Ser. No. 61/784,416 filed Mar. 14, 2013. Each application is incorporated by reference herein in its entirety.

TECHNICAL FIELD

The present disclosure relates to compositions for drug-sensitization of cancer cells. In particular, it relates to compositions including rifamycin or a rifamycin derivative, such as rifabutin or a rifabutin derivative. The present disclosure also relates to methods of sensitizing a cancer cell to another drug or combination of drugs by applying rifamycin or a rifamycin derivative, such as rifabutin or a rifabutin derivative to the cancer cell. The present disclosure additionally relates to methods of damaging cancer cells by applying rifamycin or a rifamycin derivative.

BACKGROUND

Cancer Therapeutics

Effective cancer treatment is frequently inhibited by the inability of the patient to withstand an effective dose of a therapeutic drug, by the development of resistance to therapeutic drugs by cancer cells, or both. These problems are exhibited across a wide range of cancers and therapeutic drugs. Physicians and researchers have attempted to address these problems through various approaches, such as administering multiple therapeutic drugs at once or in series, but these solutions are not optimal because they frequently pose additional risks to the patient, such as increased rates of relapse, increased chances of opportunistic infections due to increased length of treatment, and increased chances of adverse drug reactions due to exposure to more drugs.

Many of these problems could be avoided or lessened by rendering the cancer cells more sensitive to one or more therapeutic drugs. However, safe and effective methods for sensitizing cancer cells in such a manner are lacking.

Rifamycin and Rifabutin

Rifabutin is a member of the rifamycin class of antibiotics. Rifabutin was approved for use as an antibiotic in the United States in 1992. Although rifabutin has been tested for other antibiotic and anti-inflammatory uses, its most common use remains the treatment of tuberculosis and other *Mycobacterium* infections. Rifampicin, another member of the rifamycin class of antibiotics, was introduced in 1967 and is also used to treat tuberculosis and similar infections.

SUMMARY

The present disclosure, in one embodiment, relates to a composition including a rifamycin derivative or a pharmaceutically acceptable salt, hydrate, or prodrug thereof. The derivative is operable to induce drug-sensitization in a cancer cell. The derivative is also operable to inhibit a cancer cell.

According to another embodiment, the disclosure provides a method of sensitizing a cancer cell to a drug by administering rifamycin or a rifamycin derivative to the cancer cell in an amount and for a time sufficient to sensitize the cancer cell to the drug.

According to a third embodiment, the disclosure provides a method of increasing the amount of a chemotherapeutic in a cancer cell by administering rifamycin or a rifamycin derivative in an amount and for a time sufficient to decrease activity of or inhibit a p-glycoprotein (P-gp) efflux pump in the cell by.

According to a fourth embodiment, the disclosure provides a method of increasing reactive oxygen species (ROS) in a cancer cell by administering rifamycin or a rifamycin derivative to the cancer cell in an amount and for a time sufficient to increase ROS in the cancer cell.

According to a fifth embodiment, the disclosure provides a method of inhibiting a cancer cell with a drug by administering rifamycin or a rifamycin derivative to the cancer cell in an amount and for a time sufficient to sensitize the cancer cell to the drug and administering the drug to the cancer cell in an amount and for a time sufficient to inhibit the cancer cell. The amount or time of administration with respect to the drug are less than that required to achieve the same inhibition in the absence of rifamycin or a rifamycin derivative with respect to a given cancer cell type.

A sixth embodiment of the disclosure relates to a method of increasing susceptibility of a cancer cell to a drug by administering rifamycin or a rifamycin derivative to the cancer cell in an amount and for a time sufficient to increase reactive oxygen species (ROS) in the cancer cell and administering the drug to the cancer cell in an amount and for a time sufficient to inhibit the cancer cell. The amount or time of administration with respect to the drug is less than that required to achieve the same inhibition in the absence of increased ROS.

A seventh embodiment of the disclosure provides a method of inhibiting a cancer cell by administering rifamycin or a rifamycin derivative to the cancer cell in an amount and for a time sufficient to inhibit the cell.

According to an eighth embodiment, the disclosure provides a method of increasing susceptibility of a cancer cell to a drug by administering rifamycin or a rifamycin derivative to a cancer cell in an amount and for a time sufficient to increase the amount of the drug in the cancer cell as compared to the amount of the drug that would be present in the absence of the rifamycin or rifamycin derivative and administering the drug to the cancer cell in an amount and for a time sufficient to inhibit the cancer cell.

According to a ninth embodiment, the disclosure provides a method of increasing susceptibility of a cancer cell to a drug by administering rifamycin or a rifamycin derivative to the cancer cell in an amount and for a time sufficient to inhibit a p-glycoprotein (P-gp) efflux pump in the cell and administering the drug to the cancer cell in an amount and for a time sufficient to inhibit the cancer cell, wherein the amount or time are less than that required to achieve the same inhibition in the absence of inhibition of the P-gp pump.

A tenth embodiment of the disclosure provides a method of determining whether to administer rifamycin or a rifamycin derivative to a patient with cancer. The method includes obtaining a cancer cell sample from the patient, measuring the reactive oxygen species (ROS) amount in the sample, and determining if the ROS amount is low for the cancer cell type. A low ROS level indicates that administration of rifamycin or a rifamycin derivative to the patient may be beneficial The following abbreviations are used throughout the specification:
CHOP—cyclophosphamide, doxorubicin, vincristine, prednisone
NHL—non-Hodgkin's lymphoma
ROS—reactive oxygen species
RTI-x—designates a rifamycin derivative in which "x" is replaced by an identification number used in the present specification to designate a particular composition.
DOX—doxorubicin.

BRIEF DESCRIPTION OF THE DRAWINGS

The patent or application file contains at least one drawing executed in color. Copies of this patent or patent application publication with color drawings will be provided by the Office upon request and payment of the necessary fee. A more complete understanding of the present embodiments and advantages thereof may be acquired by referring to the following description taken in conjunction with the accompanying drawings, which depict embodiments of the present disclosure, and in which like numbers refer to similar components, and in which.

DETAILED DESCRIPTION

Figure 1:
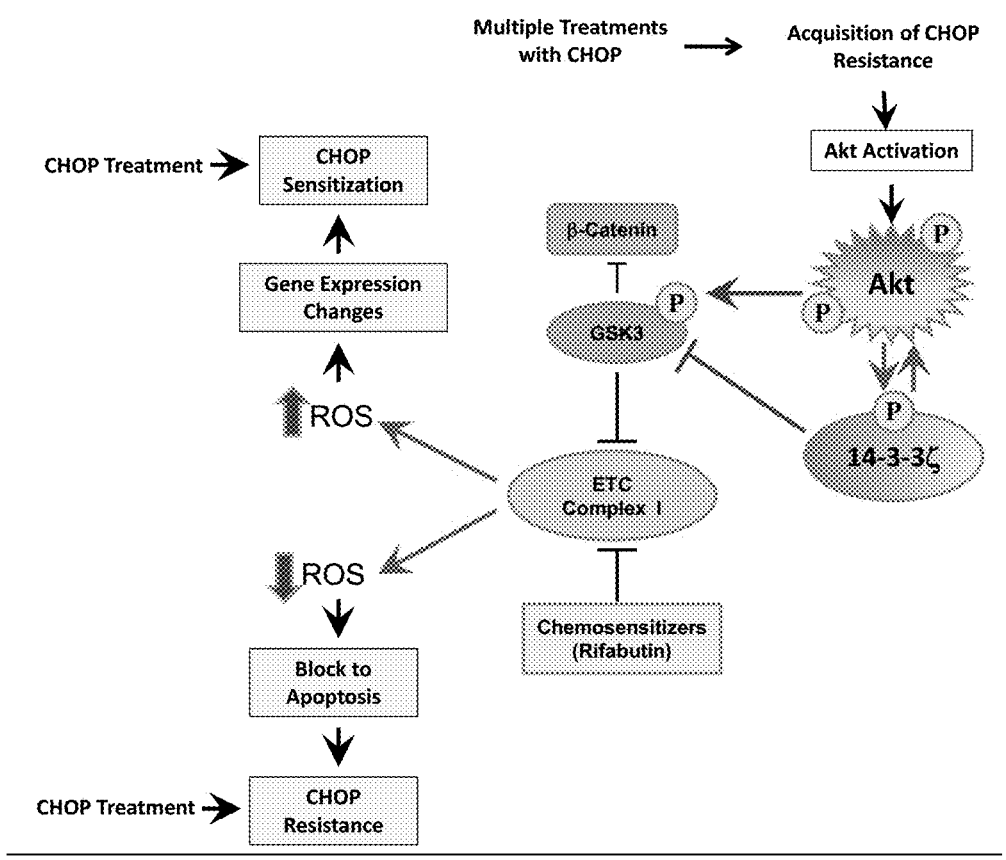
FIG. 1 illustrates a cellular network via which rifabutin or a rifabutin derivative may cause drug-sensitization and an example drug-sensitization effect in CHOP-resistant DLBCL cells.

The present disclosure relates to compositions and methods for drug-sensitization of a cancer cell or for inhibiting a cancer cell, as well as methods for diagnosis of whether a cancer cell may respond to a chemotherapeutic or to a composition described herein. These compositions and methods are described in further detail below.

Unless otherwise indicated by the specific context of this specification, a cancer cell may include a cell of any type of cancer. Furthermore, it may include a cancer cell in a patient, either in a cancerous growth, such as a tumor, or in isolation from other cancer cells, such as during metastasis. The patient may be any animal. In particular, the patient may be a mammal, such as a human, a pet mammal such as a dog or cat, an agricultural mammal, such as a horse, cow, pig, sheep, or goat, or a zoo mammal. Although many embodiments herein are expressed in terms of a cancer cell, the same or similar effects may be seen in groups of cancer cells in a patient.

Drug-sensitization, unless otherwise indicated by the specific context of this specification, may include increased sensitivity to a drug, decreased resistance to a drug, or potentiation of a drug's activity or efficacy. Any effect may be measured using any methods accepted in the art. In a specific embodiment, drug-sensitization may be determined by an increased ability of the drug to inhibit a cell. Cellular inhibition may include killing the cell, such as via apoptisis or necrosis, reducing the growth of the cell, thus reducing the growth of the cancer containing the cell, rendering the cell more susceptible to the immune system, preventing or reducing metastasis, reducing the size of a tumor containing the cell, or otherwise negatively affecting a cancer cell. An increased ability of the drug to inhibit a cancer cell may be demonstrated by an ability to inhibit the cell with a reduced amount of drug or in a shorter period of time than in the absence of drug-sensitization. In the case of drug-resistant cancer cells, which include cells with inherent or acquired resistance, drug-sensitization may result in a renewed or newly acquired ability of the drug to inhibit a cancer cell or type of cancer cell.

Compositions

The present disclosure includes drug-sensitization compositions, such as chemosensitizer compositions, including rifamycin and rifamycin derivatives, such as rifabutin or rifabutin derivatives or rifampicin and rifampicin derivatives. The present disclosure also includes compositions for inhibition of cancer cells including rifamycin and rifamycin derivatives, such as rifabutin or rifabutin derivatives or rifampicin (also called rifampin) and rifampicin derivatives. Other rifamycin derivates include rifapentine and rifalazil.

In certain embodiments, the present disclosure provides derivatives of rifabutin according to one of the following general structures:

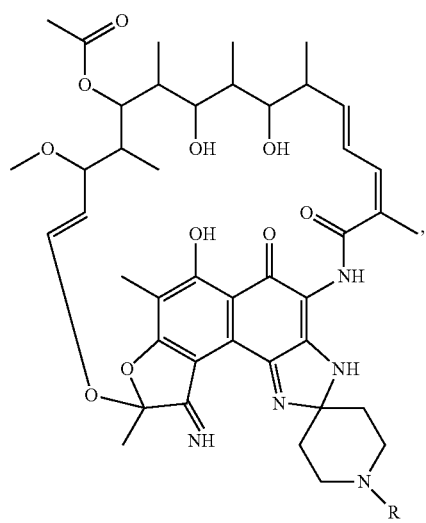
(I)
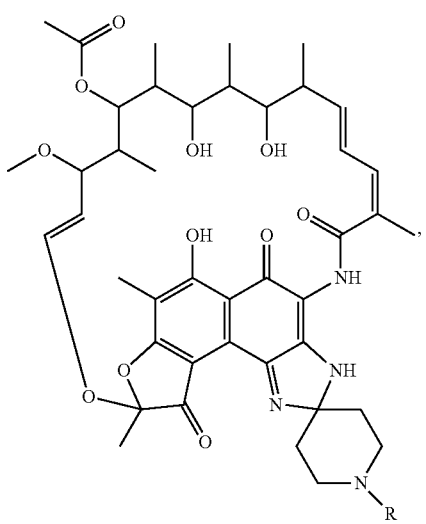
(II)
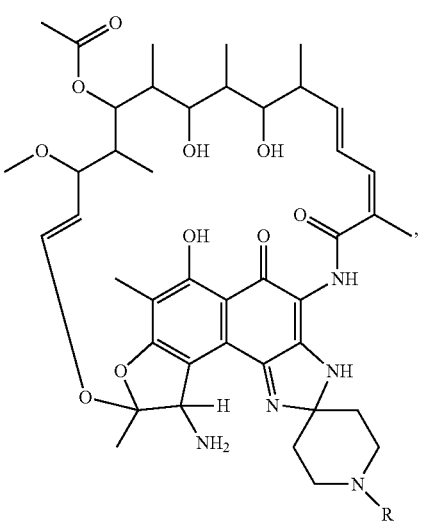
(III)
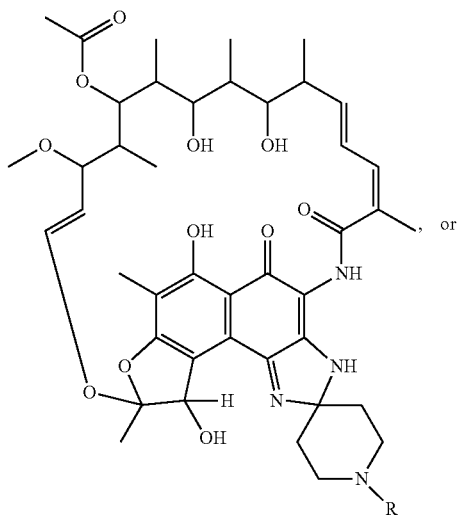
(IV)
, or
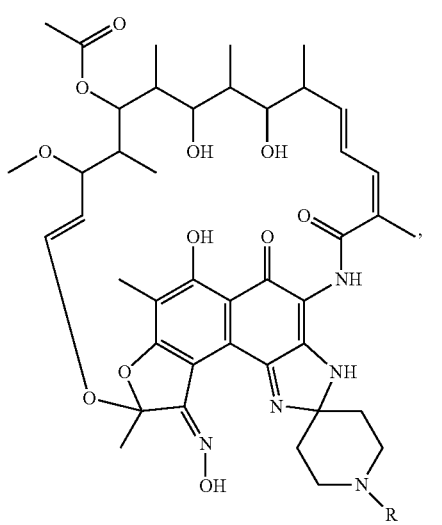
(V)
in which R may be an alkyl, aryl, or hetero aryl group.
In other embodiments, the present disclosure provides enantiomers of the general structures. In particular embodiments, it provides enantiomers with the following general chrial structures:
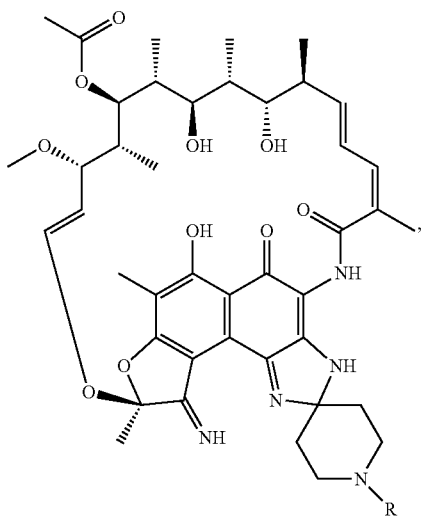
(Ia)

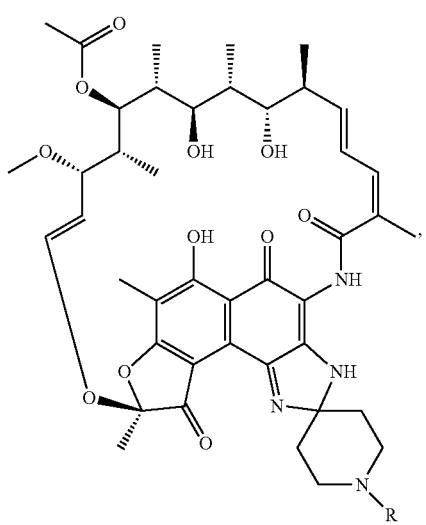

(IIa)

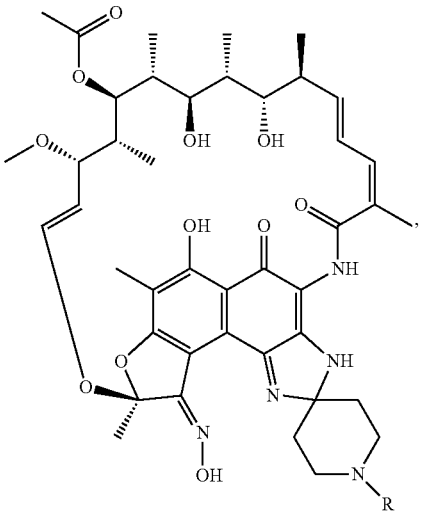

(Va)

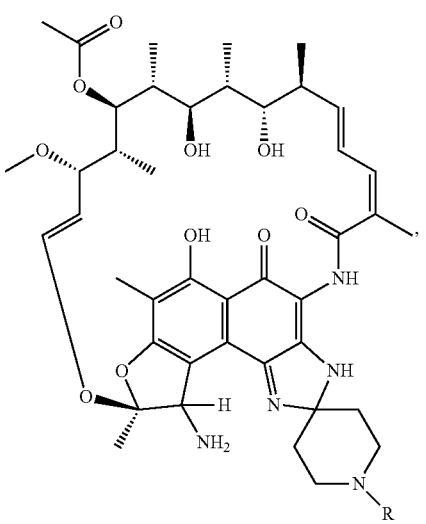

(IIIa)

in which R may be an alkyl, aryl, or hetero aryl group.

In certain embodiments having general structures I or II or general chiral structures Ia or IIa, R may be one of the following structures:

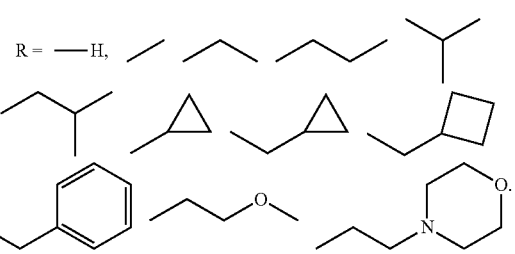

In certain embodiments, the present disclosure provides derivatives of rifabutin according to the following formula:

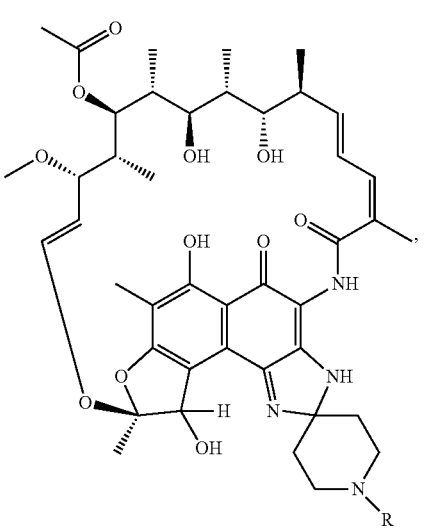

(IVa)

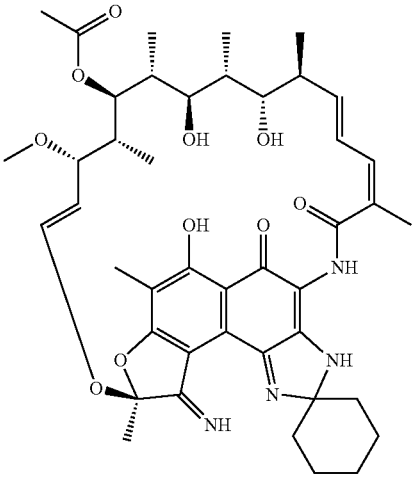

RTI-46

In certain embodiments, the present disclosure provides derivatives of rifabutin according to the following formula:

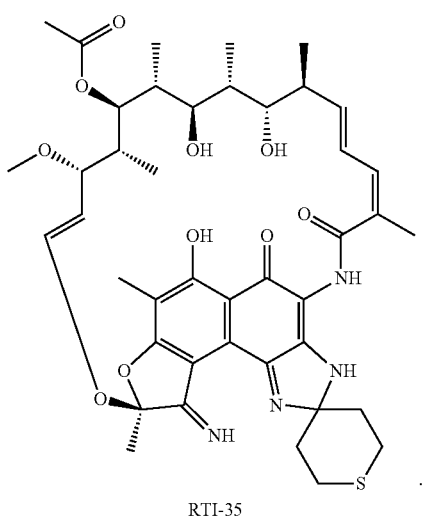

RTI-35

In certain embodiments, the present disclosure provides derivatives of rifabutin according to the following formula:

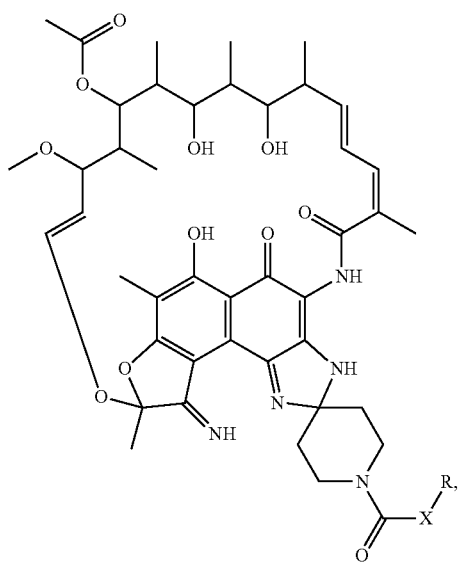

where X and R may include the following combinations:

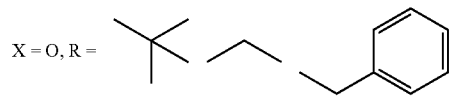

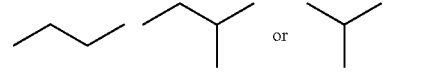

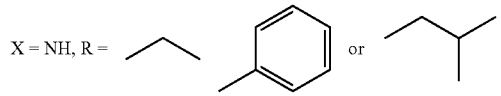

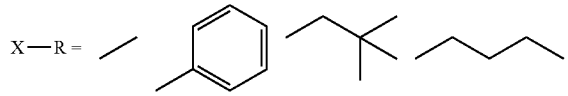

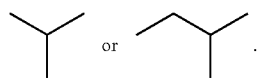

The structure with the general formula above may also be the following enantiomer:

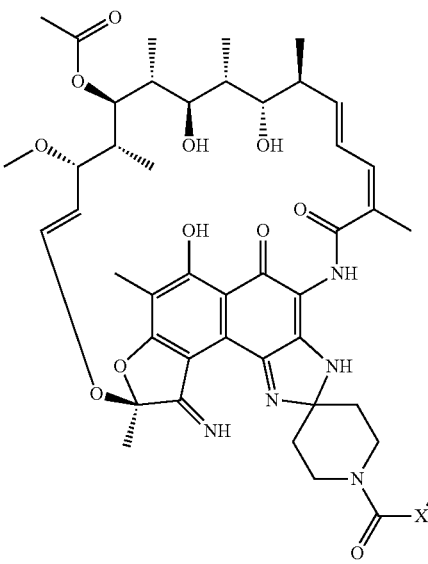

In certain embodiments, the present disclosure provides derivatives of rifabutin according to the following formula:

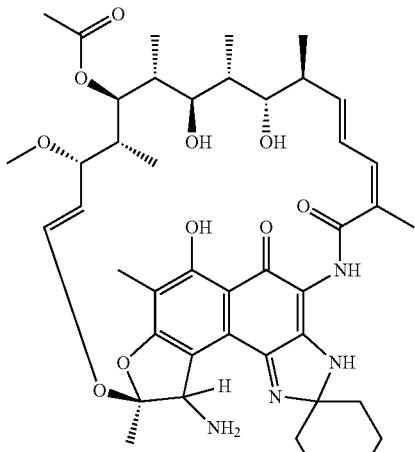

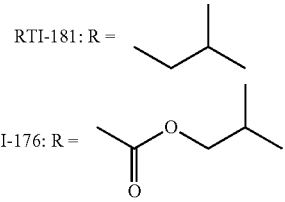

-continued

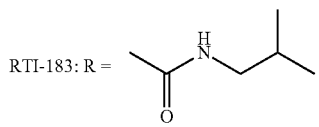

In certain embodiments having general structures III or IV or general chiral structures IIIa or IVa, R may be one of the following structures:

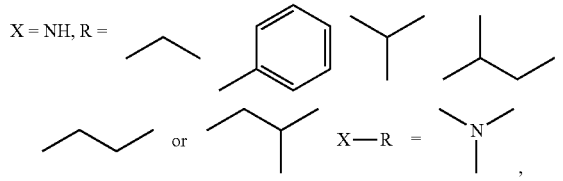

wherein X is a C, O, or N and R is an alkyl, aryl, or hetero-aryl group.

In another embodiment, the present disclosure provides derivatives of rifabutin according to the following formula:

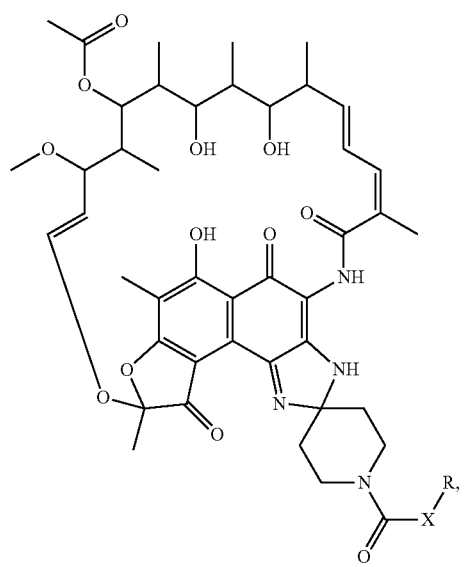

wherein X is a C, O, or N and R is an alkyl, aryl, or hetero-aryl group or wherein X and R are as follows:

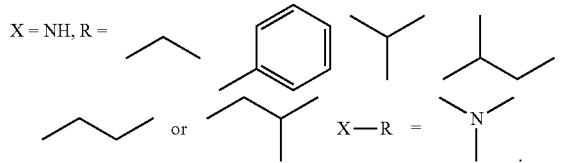

In one embodiment, a composition of the general formula above may be the following enantiomer:

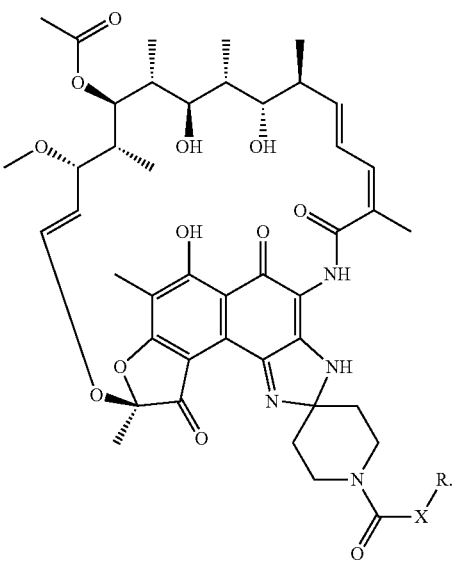

In certain embodiments, the present disclosure provides derivatives of rifabutin according to the following formula:

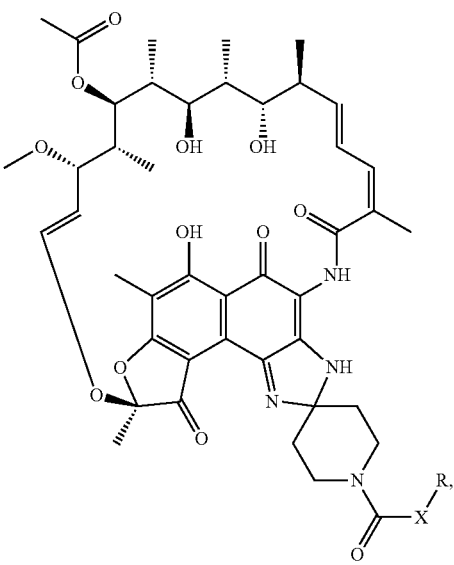

wherein X is a C, O, or N and R may include the structures listed below:

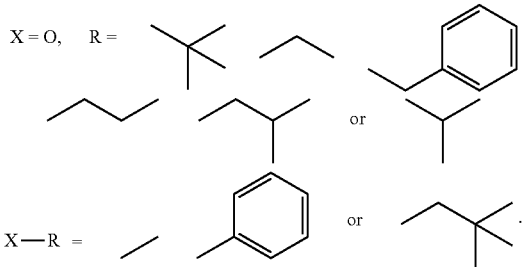

In certain embodiments, the present disclosure provides derivatives of rifabutin according to the following formula, wherein X is a C, O, or N:

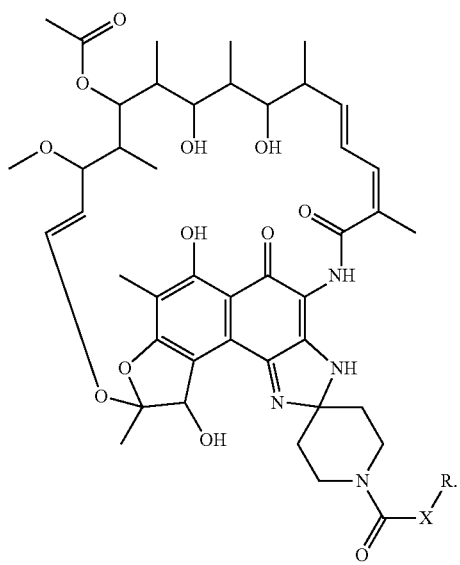

X = C, O, N

In certain embodiments, a composition with the general formula above may be the following enantiomer:

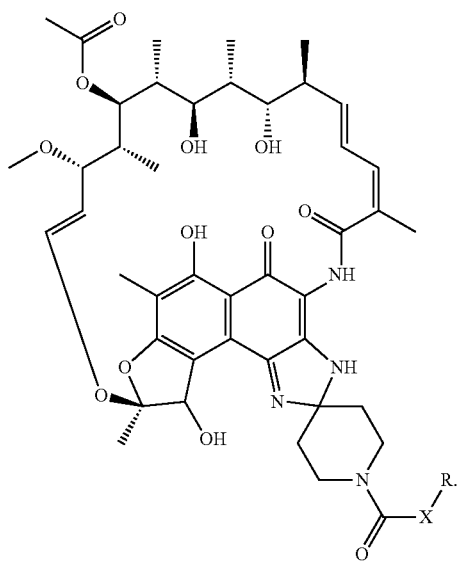

X = C, O, N

In certain embodiments, the present disclosure provides derivatives of rifabutin according to the following formula:

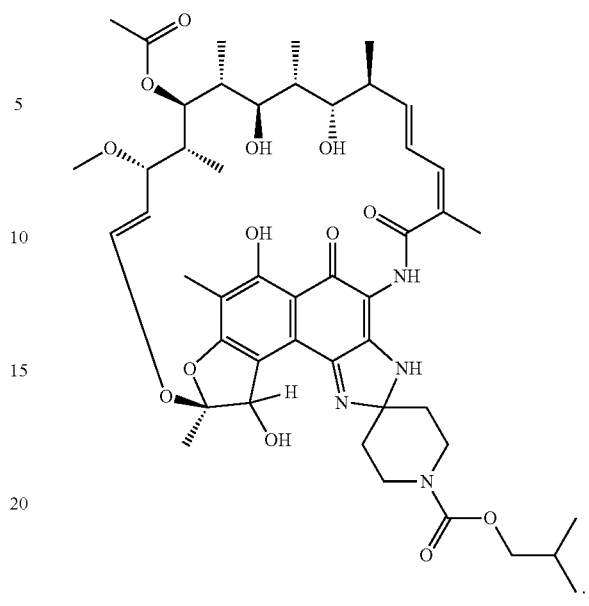

RTI-175

In certain embodiments, the present disclosure provides derivatives of rifabutin according to the following formula:

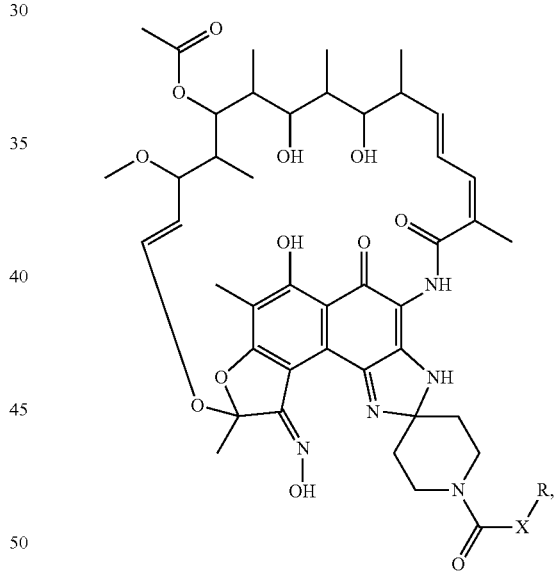

wherein X is a C, O, or N and R is an alkyl, aryl, or hetero-aryl group or wherein X and R are as follows:

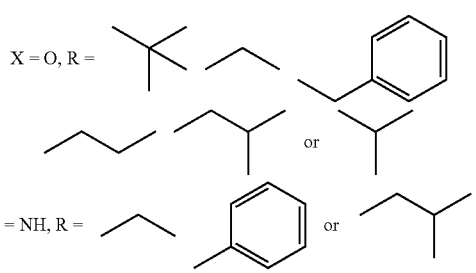

X—R = 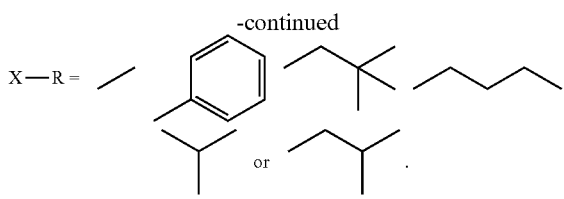

In certain embodiments, the present disclosure provides derivatives of rifabutin according to the following formula:

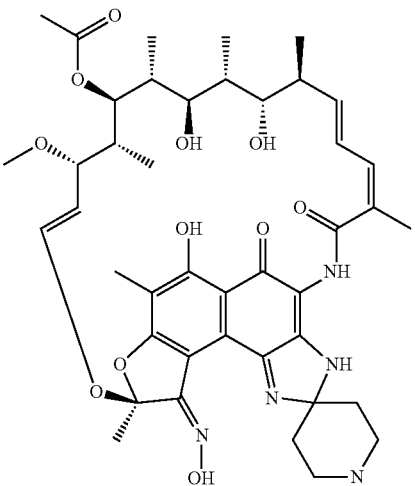

RTI-197: R = 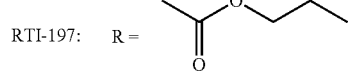

RTI-217: R = 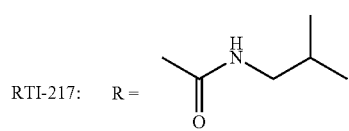

In other embodiments, the present disclosure provides a drug-sensitization composition including a series of 3,4-cyclo-rifamycin derivatives. Examples of such compositions are as follows:

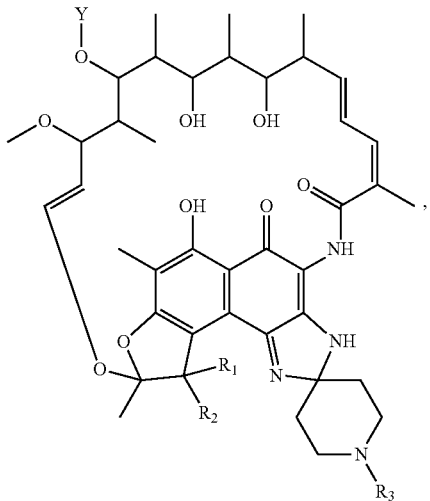

or the following enantiomer:

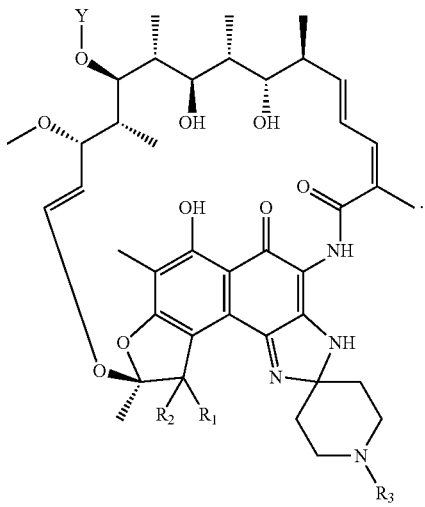

In certain embodiments X may be CH, S, SO, $SO_2$ or N. Y may be H or an acetyl group. R1 may be hydrogen. R2 may be a hydroxyl or an amino (—$NH_2$) group. R1 and R2 together may be an oxo or imine group. R3 may be one of the following groups: hydrogen, alkyl, alkenyl, alkynyl, cycloalkyl, aryl, heteroaryl and heterocycloalkyl groups that may be additionally substituted with from zero to four substituents chosen independently from halogen, hydroxy, alkoxy-alkyl, —CN, nitro, —S-alkyl, amino, alkylamino, dialkylamino, dialkylaminoalkyl, carboxy, carboalkoxy, acyl, carboxamido, alkylsulfoxide, acylamino, phenyl, benzyl, phenoxy, and benzyloxy. In certain embodiments, R3 may be —C(=O)—R4, —C(=O)—O—R4 and —C(=O)—NH—R4 where R4 is independently selected from alkyl, alkenyl, alkynyl, cycloalkyl, aryl, heteroaryl and heterocycloalkyl groups that may be additionally substituted with from zero to four substituents chosen independently from halogen, hydroxy, alkoxy-alkyl, —CN, nitro, —S-alkyl, amino, alkylamino, dialkylamino, dialkylaminoalkyl, carboxy, carboalkoxy, acyl, carboxamido, alkylsulfoxide, acylamino, phenyl, benzyl, phenoxy and benzyloxy.

In other embodiments, the present invention provides compositions of the following structure:

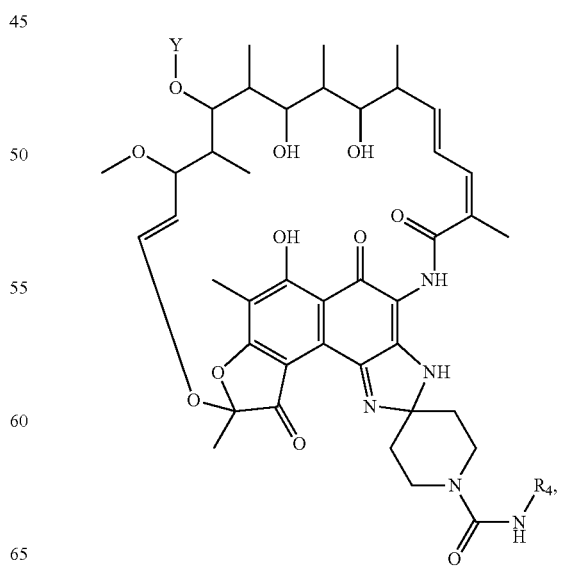

or the following enantiomer:

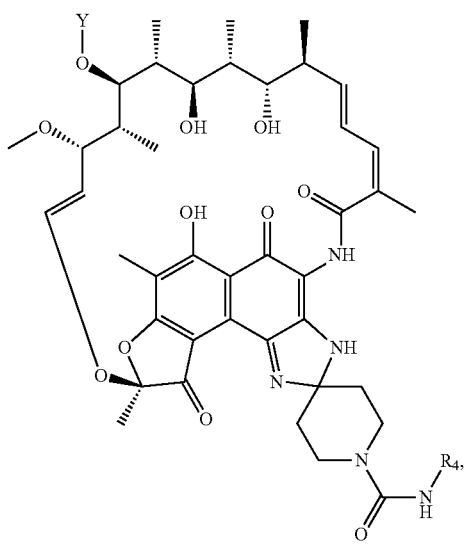

wherein Y is H or an acetyl group and R4 may be selected from alkyl, alkenyl, alkynyl, cycloalkyl, aryl, heteroaryl and heterocycloalkyl groups that may be additionally substituted with from zero to four substituents chosen independently from halogen, hydroxy, alkoxy-alkyl, —CN, nitro, —S-alkyl, amino, alkylamino, dialkylamino, dialkylaminoalkyl, carboxy, carboalkoxy, acyl, carboxamido, alkylsulfoxide, acylamino, phenyl, benzyl, phenoxy and benzyloxy.

In certain embodiments, the present invention provides compositions with the following structure:

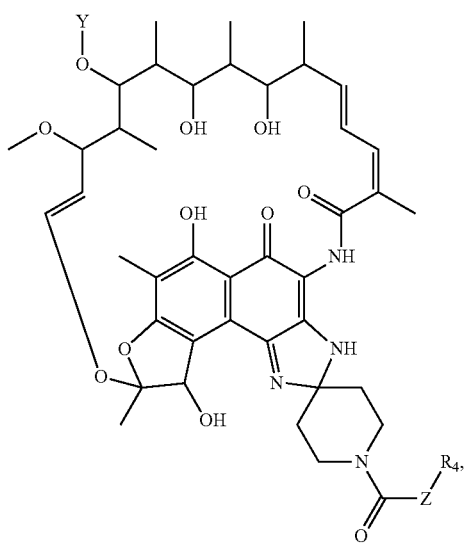

or the following enantiomer:

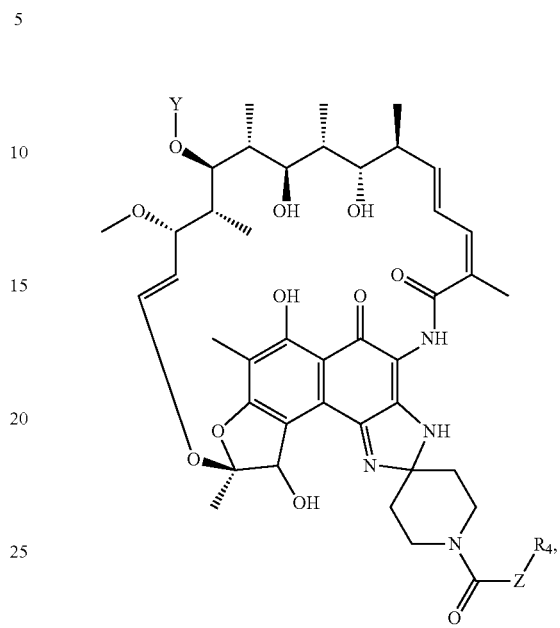

wherein Y is H, or acetyl group; Z is carbon, oxygen or nitrogen atom; and R4 is independently selected from alkyl, alkenyl, alkynyl, cycloalkyl, aryl, heteroaryl and heterocycloalkyl groups that may be additionally substituted with from zero to four substituents chosen independently from halogen, hydroxy, alkoxy-alkyl, —CN, nitro, —S-alkyl, amino, alkylamino, dialkylamino, dialkylaminoalkyl, carboxy, carboalkoxy, acyl, carboxamido, alkylsulfoxide, acylamino, phenyl, benzyl, phenoxy and benzyloxy.

Examples of drug-sensitization compositions in accordance with certain aspects of the present disclosure may include those listed in Table 1. Compositions of Table 1 are designated by like names throughout this specification.

TABLE 1

| | | Rifamycin Derivatives | |
|---|---|---|---|
| RTI-x | General structure | R | Name |
| 33 | I | ![structure] | 11-deoxy-11-imino-4-deoxy-3,4[2-spiro-[1-(t-butyloxycarbonyl)-piperidin-4-yl]]-(1H)-imidazo-(2,5-dihydro)rifamycin S |

TABLE 1-continued

Rifamycin Derivatives

| RTI-x | General structure | R | Name |
|---|---|---|---|
| 44 | I | —H | 11-deoxy-11-imino-4-deoxy-3,4[2-spiro-[piperidin-4-yl]]-(1H)-imidazo-(2,5-dihydro)rifamycin S |
| 49 | I | (benzyl) | 11-deoxy-11-imino-4-deoxy-3,4[2-spiro-[1-(benzyl)-piperidin-4-yl]]-(1H)-imidazo-(2,5-dihydro)rifamycin S |
| 51 | I | (2-methoxyethyl) | 11-deoxy-11-imino-4-deoxy-3,4[2-spiro-[1-(2-methoxyethyl)-piperidin-4-yl]]-(1H)-imidazo-(2,5-dihydro)rifamycin S |
| 53 | I | (2-morpholinoethyl) | 11-deoxy-11-imino-4-deoxy-3,4[2-spiro-[1-(2-morpholinoethyl)-piperidin-4-yl]]-(1H)-imidazo-(2,5-dihydro)rifamycin S |
| 57 | I | (cyclobutylmethyl) | 11-deoxy-11-imino-4-deoxy-3,4[2-spiro-[1-(cyclobutylmethyl)-piperidin-4-yl]]-(1H)-imidazo-(2,5-dihydro)rifamycin S |
| 59 | I | (cyclopropylmethyl) | 11-deoxy-11-imino-4-deoxy-3,4[2-spiro-[1-(cyclopropylmethyl)-piperidin-4-yl]]-(1H)-imidazo-(2,5-dihydro)rifamycin S |
| 60 | I | (isopropyl) | 11-deoxy-11-imino-4-deoxy-3,4[2-spiro-[1-(isopropyl)-piperidin-4-yl]]-(1H)-imidazo-(2,5-dihydro(rifamycin S |
| 61 | I | (t-ethyloxycarbonyl) | 11-deoxy-11-imino-4-deoxy-3,4[2-spiro-[1-(t-ethyloxycarbonyl)-piperidin-4-yl]]-(1H)-imidazo-(2,5-dihydro)rifamycin S |
| 63 | I | (acetyl) | 11-deoxy-11-imino-4-deoxy-3,4[2-spiro-[1-(acetyl)-piperidin-4-yl]]-(1H)-imidazo-(2,5-dihydro)rifamycin S |
| 64 | I | (n-propyl) | 11-deoxy-11-imino-4-deoxy-3,4[2-spiro-[1-(n-propyl)-piperidin-4-yl]]-(1H)-imidazo-(2,5-dihydro)rifamycin S |
| 65 | I | (cyclopropyl) | 11-deoxy-11-imino-4-deoxy-3,4[2-spiro-[1-(cyclopropyl)-piperidin-4-yl]]-(1H)-imidazo-(2,5-dihydro)rifamycin S |
| 66 | I | (ethyl) | 11-deoxy-11-imino-4-deoxy-3,4[2-spiro-[1-(ethyl)-piperidin-4-yl]]-(1H)-imidazo-(2,5-dihydro)rifamycin S |
| 67 | I | (benzoyl) | 11-deoxy-11-imino-4-deoxy-3,4[2-spiro-[1-(beRTIoyl)-piperidin-4-yl]]-(1H)-imidazo-(2,5-dihydro)rifamycin S |
| 68 | I | (benzyloxycarbonyl) | 11-deoxy-11-imino-4-deoxy-3,4[2-spiro-[1-(benzyloxycarbonyl)-piperidin-4-yl]]-(1H)-imidazo-(2,5-dihydro)rifamycin S |
| 69 | I | —CH$_3$ | 11-deoxy-11-imino-4-deoxy-3,4[2-spiro-[1-(methyl)-piperidin-4-yl]]-(1H)-imidazo-(2,5-dihydro)rifamycin S |
| 70 | I | (2-methylpropyl) | 11-deoxy-11-imino-4-deoxy-3,4[2-spiro-[1-(2-methylpropyl)-piperidin-4-yl]]-(1H)-imidazo-(2,5-dihydro)rifamycin S |

TABLE 1-continued

Rifamycin Derivatives

| RTI-x | General structure | R | Name |
|---|---|---|---|
| 74 | I | | 11-deoxy-11-imino-4-deoxy-3,4[2-spiro-[1-(phenylaminocarbonyl)-piperidin-4-yl]]-(1H)-imidazo-(2,5-dihydro)rifamycin S |
| 75 | II | | 4-deoxy-3,4[2-spiro-[1-(t-butoxycarbonyl)-piperidin-4-yl]]-(1H)-imidazo-(2,5-dihydro)rifamycin S |
| 76 | II | | 4-deoxy-3,4[2-spiro-[1-(ethyloxycarbonyl)-piperidin-4-yl]]-(1H)-imidazo-(2,5-dihydro)rifamycin S |
| 77 | I | | 11-deoxy-11-imino-4-deoxy-3,4[2-spiro-[1-(ethyloxycarbonyl)-piperidin-4-yl]]-(1H)-imidazo-(2,5-dihydro)rifamycin S |
| 78 | II | | 4-deoxy-3,4[2-spiro-[1-(n-propyloxycarbonyl)-piperidin-4-yl]]-(1H)-imidazo-(2,5-dihydro)rifamycin S |
| 79 | II | | 4-deoxy-3,4[2-spiro-[1-(isobutyloxycarbonyl)-piperidin-4-yl]]-(1H)-imidazo-(2,5-dihydro)rifamycin S |
| 80 | II | | 4-deoxy-3,4[2-spiro-[1-(benzyloxycarbonyl)-piperidin-4-yl]]-(1H)-imidazo-(2,5-dihydro)rifamycin S |
| 81 | I | | 11-deoxy-11-imino-4-deoxy-3,4[2-spiro-[1-(isobutyloxycarbonyl)-piperidin-4-yl]]-(1H)-imidazo-(2,5-dihydro)rifamycin S |
| 82 | I | | 11-deoxy-11-imino-4-deoxy-3,4[2-spiro-[1-(ethylaminocarbonyl)-piperidin-4-yl]]-(1H)-imidazo-(2,5-dihydro)rifamycin S |
| 83 | II | | 4-deoxy-3,4[2-spiro-[1-(ethylaminocarbonyl)-piperidin-4-yl]]-(1H)-imidazo-(2,5-dihydro)rifamycin S |
| 84 | I | | 11-deoxy-11-imino-4-deoxy-3,4[2-spiro-[1-(isopropyloxycarbonyl)-piperidin-4-yl]]-(1H)-imidazo-(2,5-dihydro)rifamycin S |
| 85 | II | | 4-deoxy-3,4[2-spiro-[1-(isopropyloxycarbonyl)-piperidin-4-yl]]-(1H)-imidazo-(2,5-dihydro)rifamycin S |

TABLE 1-continued

Rifamycin Derivatives

| RTI-x | General structure | R | Name |
|---|---|---|---|
| 86 | II | 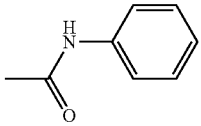 | 4-deoxy-3,4[2-spiro-[1-(phenylaminocarbonyl)-piperidin-4-yl]]-(1H)-imidazo-(2,5-dihydro)rifamycin S |
| 87 | II | 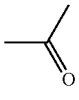 | 4-deoxy-3,4[2-spiro-[1-(acetyl)-piperidin-4-yl]]-(1H)-imidazo-(2,5-dihydro)rifamycin S |
| 88 | II | 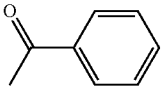 | 4-deoxy-3,4[2-spiro-[1-(beRTIoyl)-piperidin-4-yl]]-(1H)-imidazo-(2,5-dihydro)rifamycin S |
| 89 | II | 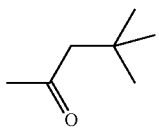 | 4-deoxy-3,4[2-spiro-[1-(3,3-dimethylbutanoyl)-piperidin-4-yl]]-(1H)-imidazo-(2,5-dihydro)rifamycin S |
| 91 | I | 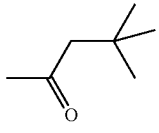 | 11-deoxy-11-imino-4-deoxy-3,4[2-spiro[1-(3,3-dimethylbutanoyl)-piperidin-4-yl]-(1H)-imidazo-(2,5-dihydro)rifamycin S |
| 94 | I | 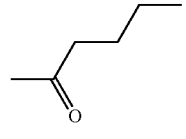 | 11-deoxy-11-imino-4-deoxy-3,4[2-spiro-[1-(n-pentanoyl)-piperidin-4-yl]]-(1H)-imidazo-(2,5-dihydro)rifamycin S |
| 97 | I | 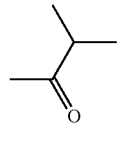 | 11-deoxy-11-imino-4-deoxy-3,4[2-spiro-[1-(2-methylpropanoyl)-piperidin-4-yl]]-(1H)-imidazo-(2,5-dihydro)rifamycin S |
| 98 | I | 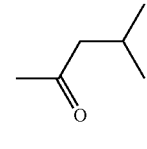 | 11-deoxy-11-imino-4-deoxy-3,4[2-spiro-[1-(3-methylbutanoyl)-piperidin-4-yl]]-(1H)-imidazo-(2,5-dihydro)rifamycin S |
| 101 | II | 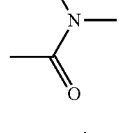 | 4-deoxy-3,4[2-spiro-[1-(dimethylaminocarbonyl)-piperidin-4-yl]]-(1H)-imidazo-(2,5-dihydro)rifamycin S |
| 102 | II | 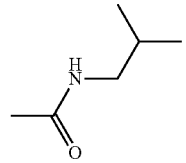 | 4-deoxy-3,4[2-spiro-[1-(isobutylaminocarbonyl)-piperidin-4-yl]]-(1H)-imidazo-(2,5-dihydro)rifamycin S |
| 103 | II | 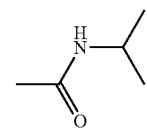 | 4-deoxy-3,4[2-spiro-[1-(isopropylaminocarbonyl)-piperidin-4-yl]]-(1H)-imidazo-(2,5-dihydro)rifamycin S |

TABLE 1-continued

Rifamycin Derivatives

| RTI-x | General structure | R | Name |
|---|---|---|---|
| 104 | II | (isopropylaminocarbonyl group) | 4-deoxy-3,4[2-spiro-[1-((1-methylpropyl)aminocarbonyl)-piperidin-4-yl]]-(1H)-imidazo-(2,5-dihydro)rifamycin S |
| 105 | II | (t-butylaminocarbonyl group) | 4-deoxy-3,4[2-spiro-[1-(t-butylaminocarbonyl)-piperidin-4-yl]]-(1H)-imidazo-(2,5-dihydro)rifamycin S |
| 174 | IV | (isobutyl group) | 11-deoxy-11-hydroxy-4-deoxy-3,4[2-spiro-[1-(2-methylpropyl)-piperidin-4-yl]]-(1H)-imidazo-(2,5-dihydro)rifamycin S |
| 175 | IV | (isobutyloxycarbonyl group) | 11-deoxy-11-hydroxy-4-deoxy-3,4[2-spiro-[1-(isobutyloxycarbonyl)-piperidin-4-yl]]-(1H)-imidazo-(2,5-dihydro)rifamycin S |
| 176 | III | (isobutyloxycarbonyl group) | 11-deoxy-11-amino-4-deoxy-3,4[2-spiro-[1-(isbutyloxycarbonyl)-piperidin-4-yl]]-(1H)-imidazo-(2,5-dihydro)rifamycin S |
| 181 | III | (isobutyl group) | 11-deoxy-11-amino-4-deoxy-3,4-[2-spiro[1-(2-methylpropyl)-piperidin-4-yl]]-(1H)-imidazo-(2,5-dihydro)rifamycin S |
| 182 | I | (isobutylaminocarbonyl group) | 11-deoxy-11-imino-4-deoxy-3,4[2-spiro-[1-(isobutylaminocarbonyl)-piperidin-4-yl]]-(1H)-imidazo-(2,5-dihydro)rifamycin S |
| 183 | III | (isobutylaminocarbonyl group with vinyl) | 11-deoxy-11-amino-4-deoxy-3,4[2-spiro-[1-(isobutylaminocarbonyl)-piperidin-4-yl]]-(1H)-imidazo-(2,5-dihydro)rifamycin S |
| 197 | V | (isobutyloxycarbonyl group) | 11-deoxy-11-hydroxyimino-4-deoxy-3,4[2-spiro-[1-(isobutyloxycarbonyl)-piperidin-4-yl]]-(1H)-imidazo-(2,5-dihydro)rifamycin S |
| 217 | V | (isobutylaminocarbonyl group) | 11-deoxy-11-hydroxyimino-4-deoxy-3,4[2-spiro-[1-(isobutylaminocarbonyl)-piperidin-4-yl]]-(1H)-imidazo-(2,5-dihydro)rifamycin S |

Modification of the rifamycin structure in locations corresponding to the 21-OH, 23-OH or 25-O—Ac sites of the rifabutin structures I, II, III, IV and V do not generally affect drug-sensitization activity and thus variations with modifications at these sites or even elimination of these sites are encompassed herein. Such variations may be used to improve synthesis yields, control costs, increase water solubility, or improve pharmaceutical properties of the composition. Sites 21, 23 and 25 are located as follows:

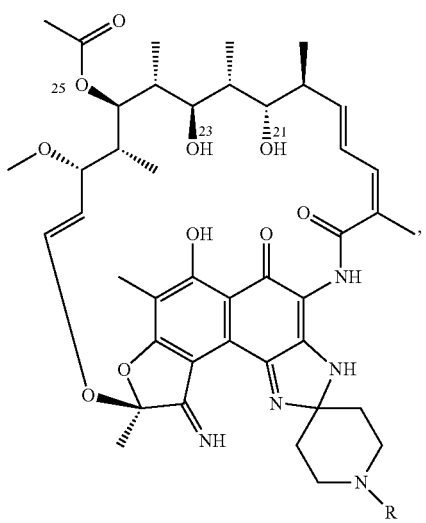

(I)

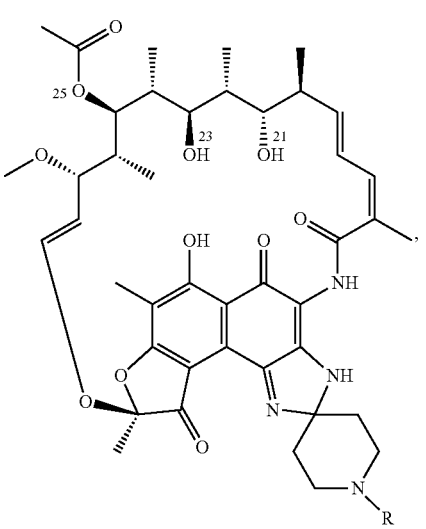

(II)

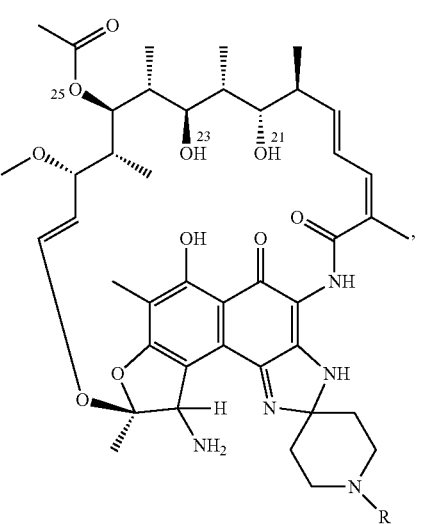

(III)

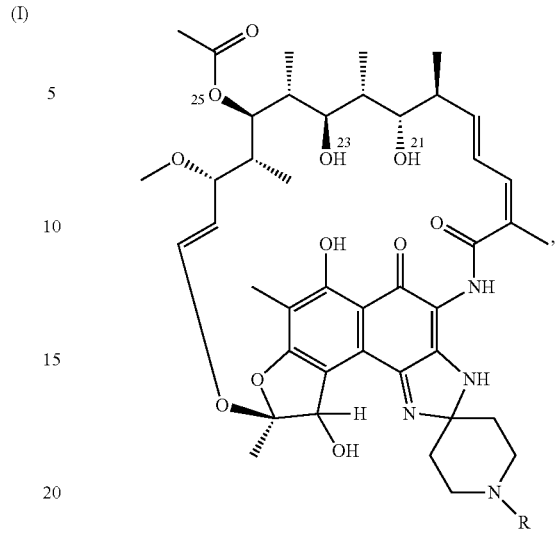

(IV)

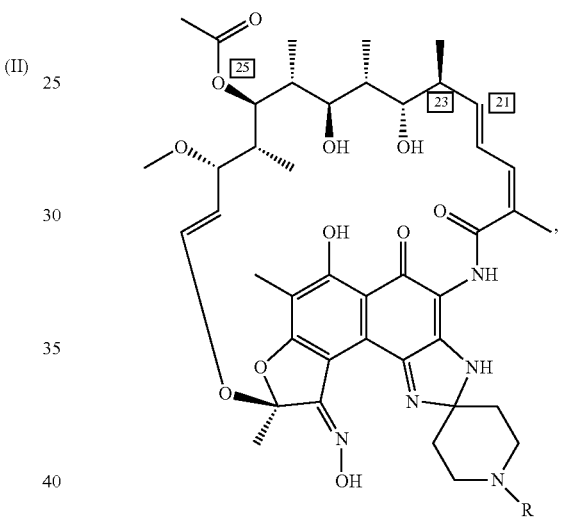

(V)

The present disclosure also includes pharmaceutically acceptable salts, hydrates, prodrugs, and mixtures of any of the above compositions. The term "pharmaceutically acceptable salt" refers to salts whose counter ion derives from pharmaceutically acceptable non-toxic acids and bases.

The 3,4-cyclo-rifamycin derivatives which contain a basic moiety, such as, but not limited to an amine or a pyridine or imidazole ring, may form salts with a variety of organic and inorganic acids. Suitable pharmaceutically acceptable (i.e., non-toxic, physiologically acceptable) base addition salts for the compounds of the present invention include inorganic acids and organic acids. Examples include acetate, adipate, alginates, ascorbates, aspartates, benzenesulfonate (besylate), benzoate, bicarbonate, bisulfate, borates, butyrates, carbonate, camphorsulfonate, citrate, digluconates, dodecyl sulfates, ethanesulfonate, fumarate, gluconate, glutamate, glycerophosphates, hemisulfates, heptanoates, hexanoates, hydrobromides, hydrochloride, hydroiodides, 2-hydroxy-ethanesulfonates, isethionate, lactate, maleate, malate, mandelate, methanesulfonate, 2-naphthalenesulfonates, nicotinates, mucate, nitrate, oxalates, pectinates, persulfates, 3-phenylpropionates, picrates, pivalates, propionates, pamoate, pantothenate, phosphate, salicylates, succinate, sulfate, sulfonates, tartrate, p-toluenesulfonate, and the like.

The 3,4-cyclo-rifamycin derivatives which contain an acidic moiety, such as, but not limited to a carboxylic acid, may form salts with variety of organic and inorganic bases. Suitable pharmaceutically acceptable base addition salts for the compounds of the present invention include, but are not limited to, ammonium salts, metallic salts made from calcium, lithium, magnesium, potassium, sodium and zinc or organic salts made from lysine, N,N-dialkyl amino acid derivatives (e.g. N,N-dimethylglycine, piperidine-1-acetic acid and morpholine-4-acetic acid), N,N'-dibenzylethylenediamine, chloroprocaine, choline, diethanolamine, ethylenediamine, meglumine (N-methylglucamine), t-butylamine, dicyclohexylamine, hydrabamine, and procaine.

The 3,4-cyclo-rifamycin derivatives, and salts thereof, may exist in their tautomeric form (for example, as an amide or imino ether). All such tautomeric forms are contemplated herein as part of the present invention.

The compounds described herein may contain asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as, their racemic and optically pure forms. Optically active (R)- and (S)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

The configuration of any carbon-carbon double bond appearing herein is selected for convenience only and unless explicitly stated, is not intended to designate a particular configuration. Thus the carbon-carbon double bond depicted arbitrarily above as E may be Z, E, or a mixture of the two in any proportion.

Abbreviations as used herein have the meanings known by one skilled in the art. Specifically, Ac represent acetyl group, Boc represents t-butoxycarbonyl group, Bn represents benzyl group, DCM represents dichloromethane, DMF represents N,N-dimethylformamide, DMSO represents dimethyl sulfoxide, Et represents ethyl group, EtOAc represents ethylacetate, Me represents methyl group, Ph represents phenyl group, TEA represents triethylamine, TFA represents trifluoroacetic acid, THF represents tetrahydrofuran, and TMS is trimethylsilane group.

Compositions of the present disclosure may also include a pharmaceutically acceptable carrier, in particular a carrier suitable for the intended mode of administration, or salts, buffers, or preservatives. Rifamycin and many of its derivatives, such as rifabutin and rifabutin derivatives are poorly soluble in water. Accordingly, aqueous compositions of the present disclosure may include solubility enhancers. Compositions for oral use may include components to enhance intestinal absorption. The overall formulation of the compositions may be based on the intended mode of administration. For instance, the composition may be formulated as a pill or capsule for oral ingestion. In other examples, the composition may be encapsulated, such as in a liposome or nanoparticle. In particular, it may be encapsulated with the drug to sensitize the cancer cell, such as encapsulated in a liposome with doxorubicin. It may also be administered with a liposomal or nanoparticle drug, such as DOXIL® (doxorubicin HCl liposome injection)(Centocor Ortho Biotech Products, LP, Raritan, N.J.), whether encapsulated with the drug or not. It may also be separately encapulsated.

Compositions of the present disclosure may contain a sufficient amount of rifamycin or rifamycin derivative to cause drug-sensitization or other inhibition of a cancer cell to occur when the composition is administered to a cancer cell. The amount of rifamycin or rifamycin derivative, such as rifabutin or rifabutin derivative may vary depending on other components of the composition and their effects on drug availability in a patient, the type of drug or drugs to which the cancer cell is sensitized, the amount of drug otherwise required to inhibit the cancer cell, the intended mode of administration, the intended schedule for administration, any drug toxicity concerns, drug-drug interactions, such as interactions with other medications used by the patient, or the individual response of a patient. Many compositions may contain an amount of rifamycin or rifamycin derivative, such as rifabutin or rifabutin derivative, well below levels at which toxicity to normal cells or to the patient overall becomes a concern.

Compositions of the present disclosure may also contain one or more drugs for which the rifamycin or rifamycin derivative, such as rifabutin or rifabutin derivative, causes drug-sensitization. Example drugs are described in the current specification. In another embodiment, compositions of the present disclosure may contain one or more other drugs commonly used in combination with the drug for which sensitization occurs. For example, a composition may include rifabutin or a rifabutin derivative with any CHOP drug, regardless of whether rifabutin causes drug-sensitization for that drug. In still another embodiment, the composition may contain another drug that also causes drug sensitization, such as a drug that affects the amount or ROS, particularly superoxide, in a cell. For example it may contain superoxide dismutase inhibitors. In still another embodiment, the composition may contain another drug that affects drug resistance or a property causing drug resistance in cancer cells. For example, it may contain drugs affecting the apoptotic pathway, such as the apoptotic pathway inhibitors for Bcl-XL or mimetics for BH3 proteins.

Compositions of the present disclosure may further include other therapeutic agents. For example, they may include any one or more of the chemotherapeutic agents listed herein, particularly those described below in connection with Drug Sensitization Methods. The amounts of those chemotherapeutic agents in compositions of the present disclosure may be reduced as compared to normal doses of such agents administered in a similar fashion.

The amount of rifamycin or rifamycin derivative, such as rifabutin or a rifabutin derivative, present in a composition may be measured in any of a number of ways. The amount may, for example, express concentration or total amount. Concentration may be for example, weight/weight, weight/volume, moles/weight, or moles/volume. Total amount may be total weight, total volume, or total moles. Typically, the amount of rifamycin or rifamycin derivative may be expressed in a manner standard for the type of formulation or dosing regimen used.

The present disclosure further includes methods of identifying whether a rifamycin derivative, such as a rifabutin derivative is able to sensitize a cancer cell or inhibit a cancer cell. Such methods include preparing or obtaining such a derivative, applying it to a cancer cell, and identifying that the derivative renders the cancer cell more susceptible to a chemotherapeutic in any manner described herein.

Drug-Sensitization Methods

The present disclosure also includes drug-sensitization methods in which a rifamycin or rifamycin derivative, such as rifabutin or rifabutin derivative, composition is administered to a cancer cell in order to sensitize the cancer cell to another drug. The composition may be any composition described above. In a specific embodiment, the composition may be administered with any other drug which may alternatively be present in a pharmaceutical composition as described herein. For example the other drug may include DOXIL®.

The drug may be any drug for which rifamycin or a rifamycin derivative, such as rifabutin or a rifabutin derivative, increases drug-sensitization. In a specific embodiment, the drug may be a chemotherapeutic. Example types of chemotherapeutics include alkylating agents, antimetabolites, anti-tumor antibiotics, hormonal agents, targeted therapies, differentiating agents and other drugs.

Example alkylating agents include nitrogen mustards such as mechlorethamine (nitrogen mustard), chlorambucil, cyclophosphamide, ifosfamide, and melphalen. Example alkylating agents further include nitrosoureas, such as streptozocin, carmustine (BCNU), and lomustine. Example alkylating agents further include alkyl sulfonates such as busulfan, triazines, such as procarbazine and dacarbazine (DTIC) and temozolomide, and ethylenimines, such as thiotepa and altretamine (hexamethylmelamine). Example alkylating agents further include platinum drugs, such as cisplatin, carboplatin, and oxalaplatin.

Example antimetabolites include purine antagonists such as mercaptopurine (6-MP), thioguanine (6-TG), fludarabine phosphate, clofarabine, cladribine, and pentostatin. Example antimetabolites also include pyrimidine antagonists such as fluorouracil (5-FU), floxuridine, capecitabine, cytarabine, gemcitabine and azacitidine. Example antimetabolites further include plant alkaloids. Some plant alkaloids include topoisomerase inhibitors such as topoisomerase I inhibitors such as camptothecin, topotecan and irinotecan, or topoisomerase II inhibitors such as amsacrine, etoposide, and teniposide. Other plant alkyloids include mitotic inhibitors such as taxanes, including paclitaxel and docetaxel, epothilones, including ixabepilone, vinca alkaloids, including vinblastine, vincristine, and vinorelbine, as well as estramustine. Example antimetabolites further include folate antimetabolites such as methotrexate and pemetrexed. Other antimetabolites include hydroxyurea.

Example anti-tumor antibiotics include anthracyclines or anthracycline analogs such as daunorubicin, doxorubicin, epirubicin, mitoxantrone, and idarubicin. Other anti-tumor antibiotics include dactinomycin, plicamycin, mitomycin, bleomycin, apicidin, and actinomycin.

Example hormonal agents include gonadotropin-releasing hormone agonists such as leuprolide and goserelin. Other example hormonal agents include aromatase inhibitors such as aminoglutethimide, exemestane, letrozole and anastrozole. Other hormonal agents include tamoxifen and flutamide. Still other example hormonal agents include antiestrogens such as fulvestrant, tamoxifen, and toremifene or anti-androgens such as bicalutamide, flutamide, and nilutamide. Example hormonal agents further include progestins such as megestrol acetate, and estrogens.

Example targeted therapies include antibodies or other therapeutics that act on a molecular level such as imatinib, gefitinib, sunitinib, and bortezomib.

Example differentiating agents include retinoids such as tretinoin, bexarotene, and arsenic trioxide.

Other chemotherapeutics include L-asparaginase, phenoxodiol, rapamycin, and menadione.

In methods of the current disclosure, the cancer cell may be sensitized to a drug already known to inhibit the cancer cell, or it may be sensitized to a drug not previously used with that type of cancer cell. If the cancer cell is a drug-resistant cancer cell that has acquired resistance, it may be sensitized to a drug that previously exhibited a decreased ability to inhibit the cancer cell or cancer cells of the same type.

In another embodiment, the composition may directly inhibit the cancer cell instead of or in addition to causing drug-sensitization.

The cancer cell that undergoes drug-sensitization or inhibition may be any type of cancer cell. It may, for instance, be a carcinoma, a sarcoma, a leukemia, a lymphoma, or a glioma. It may also be a soft cancer or a hard cancer. It may also be a cancer affecting a particular organ or tissue, such as: an immunological-related cancer such as leukemia, lymphoma, including Non-Hodgkin's lymphoma, or Hodgkin's disease, myeloma, including multiple myeloma, sarcoma, lung cancer, breast cancer, ovarian cancer, uterine cancer, including endometrial cancer, testicular cancer, intestinal cancer, including colon cancer, rectal cancer, and small intestinal cancers, stomach cancer, esophageal cancer, oral cancer, pancreatic cancer, liver cancer, prostate cancer, glandular cancers such as adrenal gland cancer and pituitary tumor, bone cancer, bladder cancer, brain and other nervous tissue cancers, including glioma, eye cancer, including retinoblastoma, skin cancer, including basal cell carcinoma and melanoma, and kidney cancer.

The composition may be delivered to the cancer cell in a patient by delivering the composition to the patient. The mode of delivery may be selected based on a number of factors, including metabolism of the rifamycin or rifamycin derivative, such as the rifabutin or rifabutin derivative, or another drug in the composition, mode of administration of other drugs to the patient, such as the drug to which the cancer cell is sensitized, the location and type of cancer cell to be drug-sensitized, health of the patient, ability or inability to use particular dosing forms or schedules with the patient, preferred dosing schedule, including any adjustment to dosing schedules due to side effects of chemotherapeutics, and ease of administration. In specific embodiments, the mode of administration may be enteral, such as orally or by introduction into a feeding tube. In other specific embodiments, the mode of administration may be parenteral, such as intravenously.

The dosage amounts of the rifamycin or rifamycin derivative, such as rifabutin or rifabutin derivative and administration schedule may vary depending on other components of the composition and their effects on drug availability in a patient, the type of drug or drugs to which the cancer cell is sensitized, the intended mode of administration, the intended schedule for administration, when other drugs are administered, any drug toxicity concerns, and the patient's response to the drug. In a specific embodiment, the amount and frequency of rifamycin or rifamycin derivative such as rifabutin or rifabutin derivative delivered may be such that levels in the patient remain well below levels at which toxicity to normal cells or to the patient becomes a concern. However the amount and frequency may also be such that the rifamycin or rifamycin derivative, such as rifabutin and rifabutin derivative, levels in the cancer cell remain continuously at a level sufficient to induce drug-sensitization or are at a level sufficient to induce-drug sensitization when or shortly after the drug to which the cancer cell is sensitized is delivered to it. Accordingly, the rifabutin or rifabutin derivative composition may be taken on a regular basis during treatment with the drug to which the cancer cell is sensitized or it may be taken only a set time before, at the same time, or a set time after the drug to which the cancer cell is sensitized.

Cancer Inhibition Methods

In some specific embodiments, the disclosure provides methods of inhibiting a cancer cell using a drug to which the cancer cell is resistant by administering rifamycin or a rifamycin derivative, such as rifabutin or a rifabutin derivative, to the cancer cell.

In other specific embodiments, the disclosure provides methods of reducing the amount of a drug administered to a patient by also administering rifamycin or a rifamycin derivative, such as rifabutin or a rifabutin derivative. Such methods may, in particular, be employed with drugs that have other harmful effects. For example, use of certain alkylating agents, such as topoisomerase inhibitors, increases the later chances of leukemia in the patient. The chance of this adverse effect may be lessened if lower doses of the alkylating agent may be administered with the same therapeutic effect. Similarly, methods of the present disclosure may be used to reduce the amount of mitotic inhibitors administered, reducing the chance or amount of resulting peripheral nerve damage, or the methods may be used to reduce the amount of anti-tumor antibiotics administered, reducing the chance or amount of resulting hearing damage. In the case of anti-tumor antibiotics for which there is a total lifetime dosage limit, methods of the present disclosure may allow a patient to be treated with the drug for a longer time, increasing life expectancy or improving quality of life. Methods of the present disclosure may also allow amounts of some chemotherapeutics administered to remain sufficiently low as to allow the patient to have children after cancer treatment. Methods of the present disclosure may further allow amounts of the chemotherapeutics administered to be lowered into a range where a drug approved for use in adults might also be used in children.

In an alternative embodiment in which the rifamycin or rifamycin derivative, such as rifabutin or rifabutin derivative directly inhibits a cancer cell alone or in addition to causing drug-sensitization, the dosage and administration may be adequate to allow this inhibition. In an example embodiment, it may consist of regular administration of an amount of the rifamycin or rifamycin derivative, such as rifabutin or rifabutin derivative, to maintain a certain level in the patient, the blood, a tissue, or a tumor. However, dosage amounts and the administration schedule may be adjusted based on other components of the composition and their effects on drug availability in a patient, the intended mode of administration, the intended schedule for administration, when other drugs are administered, any drug toxicity concerns, and the patient's response to the drug.

Without limiting the compositions and methods of administration described herein, in one embodiment, rifamycin or a rifamycin derivative, such as rifabutin or a rifabutin derivative, may exhibit its drug-sensitization effect on a cancer cell by directly or indirectly inhibiting an efflux pump, such as the ATP-binding cassette sub-family B member 1 (ABCB1) pump. This glycoprotein is found in the cell membrane and actively transports certain chemotherapeutics, such as doxorubicin, out of cancer cells, reducing efficacy of the drug. By inhibiting this pump, the amount of chemotherapeutic present in a cancer cell can be increased and thus the killing effect on the cancer cell may be increased.

According to one embodiment of the present disclosure, rifabutin and rifabutin derivatives suppress ABCB1 activity, increasing the effective amount of a chemotherapeutic within a cancer cell.

Also, without limiting the compositions and methods of administration described herein, in one embodiment, rifamycin or a rifamycin derivative, such as rifabutin or a rifabutin derivative, may exhibit its drug-sensitization effect on a cancer cell by acting on the Akt (protein kinase B)/14-3-3ζ/mitochondrial electron transport chain (ETC)/reactive oxygen species (ROS) signaling network within a cell. An example of how the rifamycin or rifamycin derivative can effect this pathway in a drug-resistant cancer cell is shown in FIG. 1. In this example, a CHOP-resistant cancer cell, such as a CHOP-resistant diffuse large B-cell lymphoma (DLBCL) cell, undergoes cellular changes such that Akt is constitutively activated. This constitutively activated Akt phosphorylates mitochondrial GSK-3β. This phosphorylated GSK-3β then binds the 14-3-3ζ protein, rendering the GSK-3β unavailable to bind to mitochondrial ETC Complex 1. GSK-3β binding to ETC Complex 1 inhibits the complex activity, so the overall result of constitutive Akt activation is that ETC Complex 1 is not inhibited when it otherwise should be. Downregulation of Complex I activity by GSK-3β can lead to increased electron leakage from the ETC, resulting in increases in ROS.

ETC Complex 1 acts to reduce the amount of electron spillage from the ETC during mitochondrial activity. Electrons spilled in such a manner react with oxygen to produce reactive oxygen species (ROS). Thus, increased ETC Complex 1 activity and the resultant reduction in electron leakage decrease the amount of ROS in the cell. Low levels of ROS may lead to an intracellular environment that inhibits the ability of chemotherapeutics such as CHOP to induce cancer cell death by apoptosis. Thus, one effect of constitutive Akt activation is a decrease in ROS, making the cancer cell harder to kill.

According to one embodiment of the present disclosure, rifamycin or a rifamycin derivative, such as rifabutin and rifabutin derivative suppress ETC Complex 1 activity, restoring it to a more normal level. As a result, more ROS are present in the cell and the cellular environment is restored to one in which CHOP may once again induce cell death via apoptosis.

A similar effect may be seen with other chemotherapeutics or other drugs whose efficacy relies on a cellular environment with minimum amount of ROS or other factors (such as other intracellular chemicals, proteins, or conditions) resulting from a minimum amount of ROS in the cell.

As a result of this effect on the Akt/14-3-3ζ/ETC/ROS network, the present disclosure also includes methods of inducing drug-sensitization in a cancer cell by administering an amount of rifabutin or rifabutin derivative sufficient to decrease activity of ETC Complex 1 or increase cellular levels of ROS. In particular, the disclosure includes methods of administering an amount of rifabutin or rifabutin derivative sufficient to increase cellular levels of ROS to an amount sufficient to allow a drug to which a cancer cell is sensitized to kill, reduce the growth of, or negatively affect the cancer cell.

Although the above example relates to cancer cells that have become resistant to a drug due to abnormal Akt activity, the same methods are applicable to cancer cells that exhibit low ROS levels for other reasons. Furthermore, the same methods may be used for drug-sensitization in cancer cells that have no ROS abnormality by increasing ROS to an abnormal level if the cancer cells then become sensitive to the drug at the abnormal ROS level.

Effects mediated by ROS described above may, in particular, be mediated by superoxide species and superoxide species may be the particular form of ROS affected.

Although some drug-sensitization or cancer cell inhibition effects may be mediated by the ROS pathway, compositions and methods of the present disclosure may act via other cellular pathways alternatively to or in addition to the Akt/14-3-3ζ/ETC/ROS network. This may be particularly true with respect to drug-sensitization to chemotherapeutics that operate in a different manner than CHOP. For example, ROS may affect the mitochondrial-directed Bcl-2 apoptosis pathway as well. Furthermore, the effect of rifabutin on ROS induction has been shown to be very rapid, whereas the effect on Akt has been shown to take at least 18 hours. Accordingly, it appears likely that an initial ROS induction event may occur, followed by a secondary downstream effect downregulating Akt. In CHOP-resistant cells, Akt is constitutively active thereby increasing Complex I activity resulting in decreases in ROS. Induction of ROS by compositions and methods of the present disclosure will further promote drug sensitivity in the resistant cancer cell by downregulating the Akt pathway.

Again without limiting the compositions and methods of administration described herein, in one embodiment, rifamycin or a rifamycin derivative, such as rifabutin or a rifabutin derivative, may exhibit its drug-sensitization effect on a cancer cell by mobilizing calcium within the cell. Increased calcium mobilization correlates with increased ROS amounts. Drug-sensitive cells often exhibit both increased levels of calcium and increased ROS levels as compared to drug-resistant cells. Typically, ROS levels rise first in such cells, followed by calcium mobilization. Accordingly, rifamycin or a rifamycin derivative, such as rifabutin or a rifabutin derivative, may directly inhibit efflux pump activity, which then causes a burst of ROS followed by calcium mobilization.

According to one embodiment of the present disclosure, rifamycin or a rifamycin derivative, such as rifabutin or a rifabutin derivative, may inhibit a cancer cell through more than one activity. For instance, it may both decrease efflux pump activity and increase ROS. In certain embodiments, these multiple activities may have synergistic effects.

Further without limiting the compositions and methods of administration described herein, the compositions and methods may prevent or reduce metastasis. Metastasis from solid tumors is a complex, multistep process whereby cancer cells must breach the basement membrane and migrate away from the primary tumor environment to invade the surrounding stroma and enter the vasculature directly or via the lymphatics. The cancer cells must then also invade another area of the body. Rifabutin or a rifamycin derivative, such as rifabutin or a rifabutin derivative, may prevent or reduce metastasis by preventing or reducing any of these movements or activities of the cancer cells. Rifamycin or a rifamycin derivative, such as rifabutin or a rifabutin derivative, may also decrease the levels of metastasis-associated cellular factors in or around cancer cells. Such factors include matrix metalloproteinase (MMP) 2 or other MMP family members and vascular endothelial growth factor (VEGF). MMP family members are involved in the breakdown of extracellular matrix in disease processes such as metastasis. VEGF is an important signaling protein involved in both vasculogenesis (the formation of the circulatory system) and angiogenesis (the growth of blood vessels from pre-existing vasculature).

Determining Appropriate Cancer Targets

The present disclosure also provides a method of determining whether a cancer cell is likely to be resistant to chemotherapeutics or experience an increase in ROS or drug-sensitization in response to rifamycin or a rifamycin derivative, such as rifabutin or a rifabutin derivative, or if treatment with such a composition is having an effect on a cancer cell. In such a method, ROS, such as superoxide species, may be measured in cancer cells of the same type. If ROS is abnormally low compared to ROS levels previously measured in cancer cells of the same type (e.g. 3-10 fold lower), then the cancer cell may be more likely to not respond to a chemotherapeutic than cancer cells with higher ROS levels. The cancer cell may also exhibit an increase in ROS or be sensitized to a drug in response to rifamycin or a rifamycin derivative, such as rifabutin or a rifabutin derivative, so such a composition may be administered to the cancer cell along with a drug to which a cancer cell is sensitized to inhibit the cancer cell. If the patient has been treated with rifamycin or a rifamycin derivative, such as rifabutin or a rifabutin derivative, and ROS levels are normal for that type of cancer cell, higher than in previous measurements from that patient, or higher than normal for the type of cell from which the cancer is derived, then the treatment is likely successful and should be continued.

Alternatively, rather than measure ROS directly, an indicator of ROS levels may be measured. In a specific embodiment, ROS may be measured using ROS stains.

In another embodiment, the amount of ROS (or indicator of ROS levels) in cancer cells of a certain type may be measured and, if below a certain threshold, rifamycin or a rifamycin derivative, such as rifabutin or a rifabutin derivative, may be administered to a cancer cell of the same type along with a drug to which a cancer cell is sensitized to inhibit the cancer cell.

In specific embodiments, ROS-related measurements may be made by any conventional methods. For example, ROS-related measurements may be made on a biopsy, resection or aspirant of a tumor or cancer-bearing tissue, a blood sample, or cancer cells isolated by other means. Measurements are compatible with presently known methods of obtaining cancer cells from patients and are expected to be similarly compatible with additional methods developed in the future.

EXAMPLES

The following examples are provided to further illustrate specific embodiments of the disclosure. They are not intended to disclose or describe each and every aspect of the disclosure in complete detail and should be not be so interpreted. Unless otherwise specified, designations of cells lines and compositions are used consistently throughout these examples.

Example 1—Drug-Sensitization of CHOP-Resistant NHL Cell Lines

Several human cell lines were utilized as in vitro models of NHL, including the CRL2631 line obtained from the American Type Culture Collection (ATCC). CRL2631 was established from peripheral blood leukocytes (PBL) of a patient with DLBCL. CHOP-resistant NHL cell lines (designated G3) were generated by repeated cycles of on-off treatments with CHOP, a treatment protocol that is similar to clinical regimens.

Figure 2A:
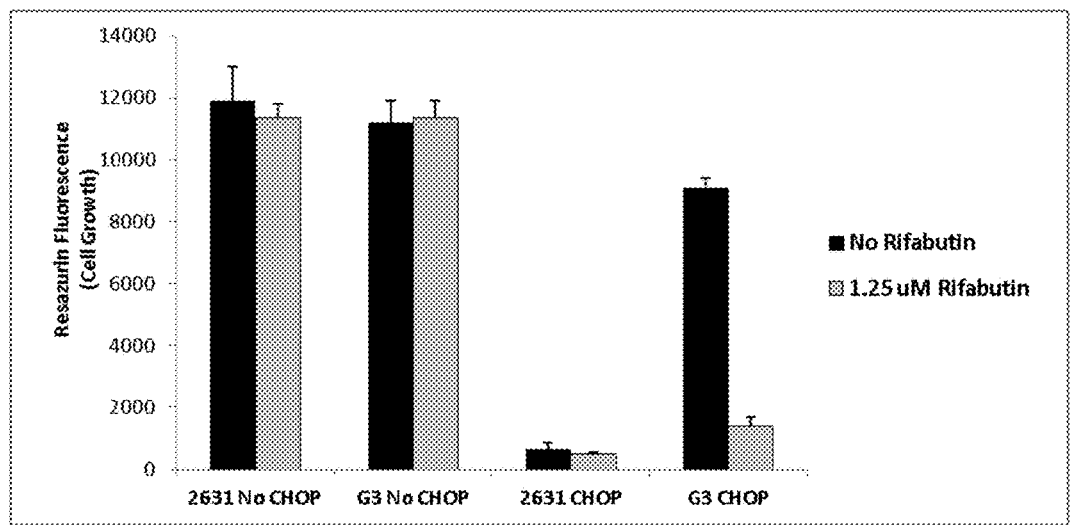
FIG. 2A illustrates the effects of rifabutin on growth of CHOP-sensitive (CRL2631) NHL cells and CHOP-resistant (G3) NHL cells in the presence or absence of CHOP as demonstrated by resazurin fluorescence.

The effects of rifabutin on cell growth of both CHOP-sensitive (CRL2631) and CHOP-resistant (G3) cells in the presence or absence of CHOP are shown in FIG. 2A. A reduction in cell growth is demonstrated by a reduction in fluorescence emitted by the cell growth indicator dye, resazurin.

Figure 2B:
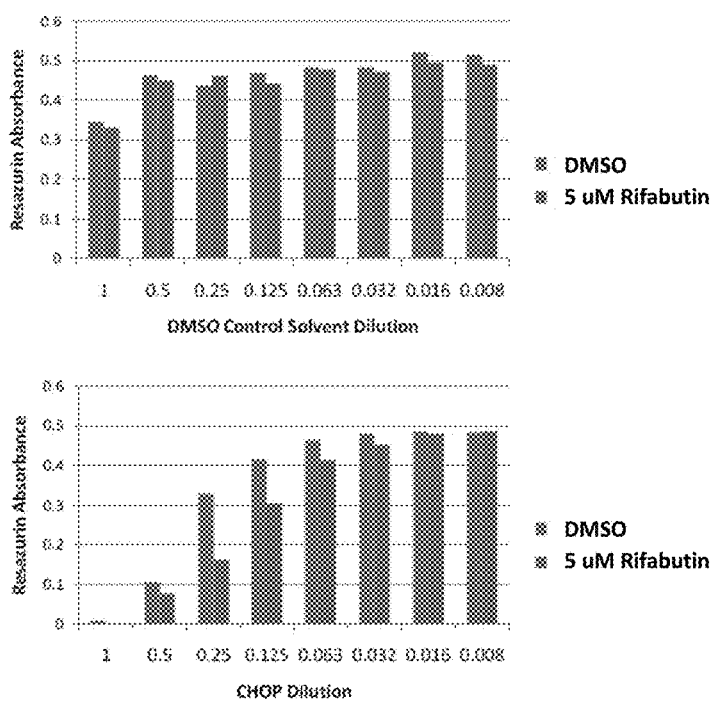
FIG. 2B illustrates the effects of rifabutin on growth of CHOP-resistant (G3) NHL cells in the absence of CHOP (top panel) as compared to a control drug as demonstrated by resazurin fluorescence and in the presence of varying dilutions of CHOP for 24 hrs (bottom panel)
Figure 2C:
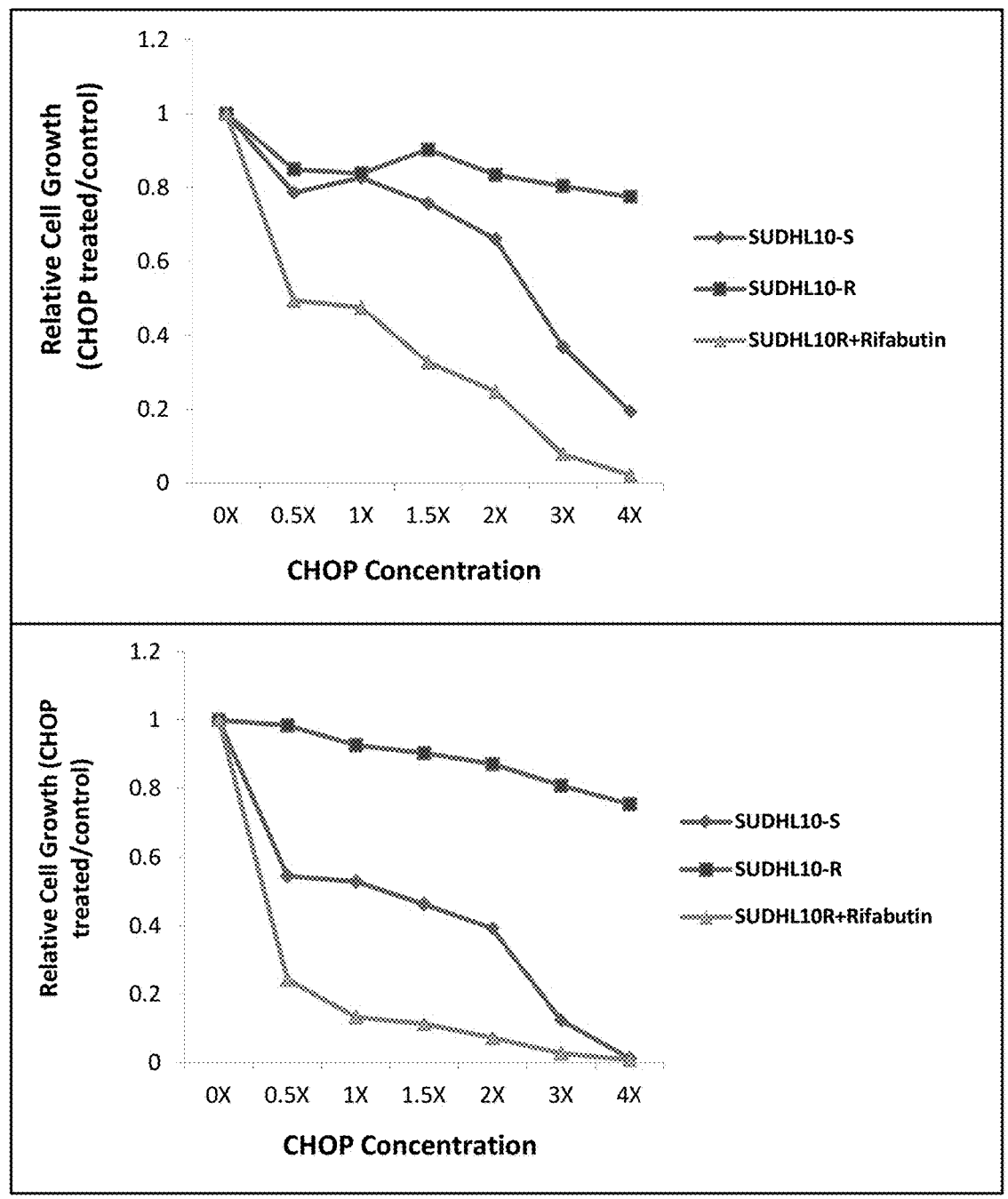
FIG. 2C illustrates the effects of rifabutin on growth of another CHOP-resistant NHL cell line (SUDHL10-R) and the parental CHOP-sensitive NHL cell line (SUDHL10-S) after 24 hrs (top panel) and 48 hrs (bottom panel) of treatment as demonstrated by resazurin fluorescence.

Rifabutin was confirmed to have drug-sensitization activity in clinically derived CHOP resistant cell lines. As shown in FIG. 2A, CHOP inhibited growth of CHOP-sensitive (CRL2631) cells but had little effect on G3 cells. Rifabutin did not affect the growth of cells in the absence of CHOP, indicating low toxicities (FIG. 2A). Rifabutin enhanced the sensitivity of CHOP-sensitive cells to CHOP as shown in FIG. 2B, relative to a control drug. FIG. 2C shows similar effects in another CHOP-resistant NHL line.

Example 2—Toxicity

Figure 3A:
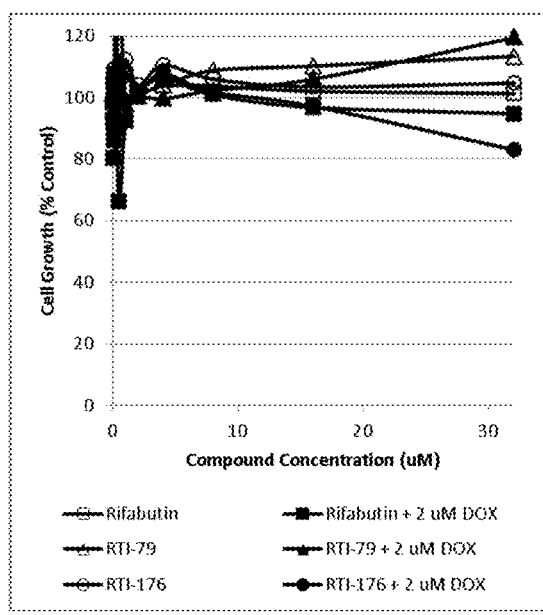
FIG. 3A illustrates the effects of rifabutin or rifabutin derivatives RTI-79 and RTI-176 on cell growth of primary human dermal fibroblasts both with and without 2 uM Dox.
Figure 3B:
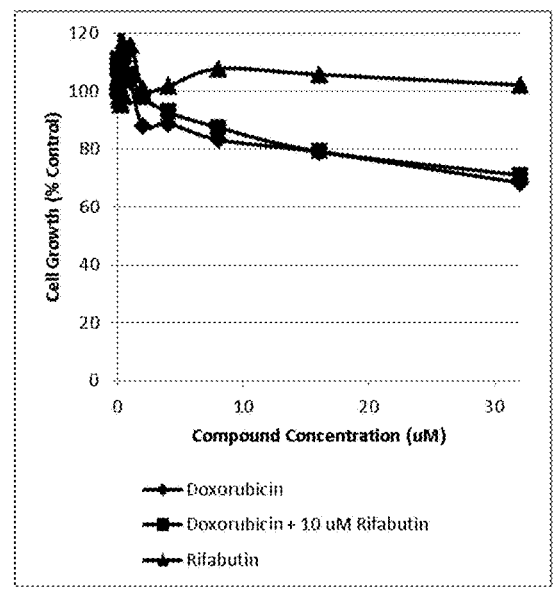
FIG. 3B illustrates the effects of doxorubicin and rifabutin on cell growth of primary human dermal fibroblasts.

Doxorubicin and rifabutin or its derivatives RTI-79 and RTI-176 were applied to primary human fibroblasts to determine comparative cytotoxicity. Results are presented in FIG. 3A and FIG. 3B and demonstrate that rifabutin and the analogs are not toxic to normal cells.

To further test safety of rifabutin and its derivatives, rifabutin and rifabutin derivates RTI-79 and RTI-81 were administered as an adjunct therapy to doxorubicin (DOX). Swiss mice were dosed with levels equal to and exceeding that of intended doses. Swiss mice were given repeated weekly oral doses of rifabutin at 180 mg/kg, RTI-79 at 250 mg/kg or RTI-81 at 30 mg/kg in conjunction with intravenous 3.3 mg/kg DOX. No overt toxicity or weight loss was seen over several weeks time. Further, no significant differences between mice treated with RTI-79 with or without DOX were observed after both histological analysis of heart tissue by hematoxylin and eocin (H&E) and analysis of blood and serum for complete blood count and manual differential. Intravenous rifabutin or RTI-81 were also given repeatedly both at 75 mg/kg in conjunction with intravenously administered 3.3 mg/kg DOX and no overt toxicity or weight loss was seen over several weeks time. Further data in Example 4 below shows treatment efficacy using less than one-fifth the above oral dose of 33 mg/kg rifabutin with intravenous 3.3 mg/kg doxorubicin.

Example 3—Drug-Sensitization of CHOP-Resistant Lymphoma Cells from Dog Model

Figure 4:
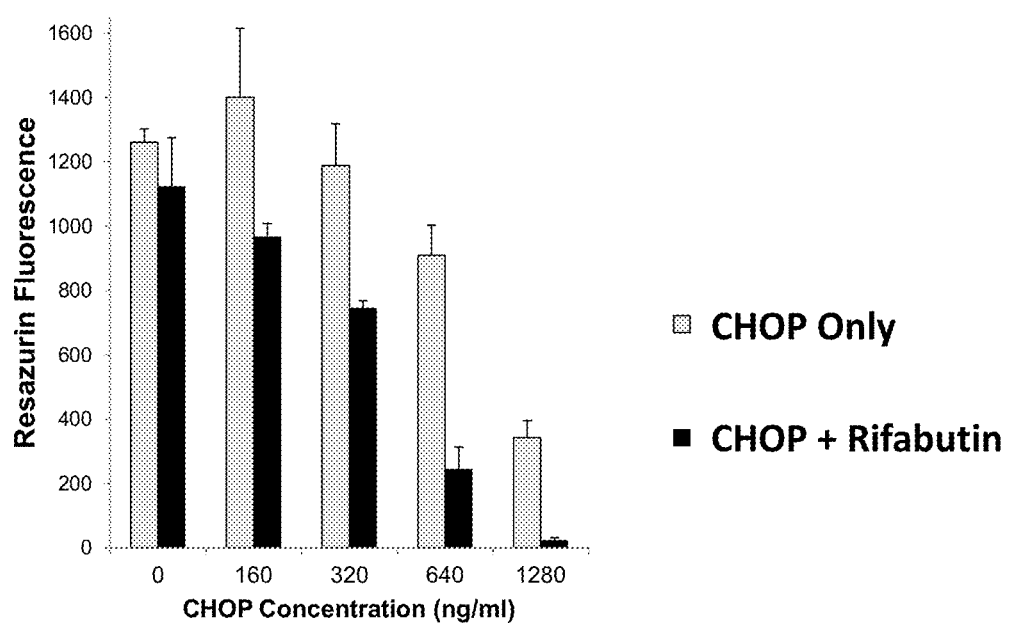
FIG. 4 illustrates the effects of rifabutin on growth of CHOP-resistant lymphoma cells obtained by aspiration from a dog as demonstrated by resazurin fluorescence.

A single lymphoma aspirate from a dog with CHOP-resistant lymphoma was tested for responsiveness to CHOP in the presence or absence of rifabutin. CHOP-responsiveness was measured by a decrease in fluorescence signal generated by resazurin. FIG. 4 shows that growth of aspirated lymphoma cells was resistant to CHOP at doses up to 640 ng/ml, but significant growth inhibition was observed at a dose of 1280 ng/ml CHOP. The inclusion of 5 µM rifabutin significantly enhanced the sensitivity of the aspirated lymphoma cells to CHOP such that significant growth inhibition was observed at 320 and 640 ng/ml CHOP. Rifabutin had no effect on cell viability in the absence of CHOP.

Example 4—Drug-Sensitization In Vivo

In a first efficacy study, 6-8 week old female SCID mice (7 mice per treatment arm) were injected subcutaneously on both flanks with $1\times10^7$ G3 CHOP-resistant NHL cells. Once palpable tumors (about 50-100 cc size) appeared, therapies (CHOP or CHOP+rifabutin) were started. CHOP was administered at the maximum tolerated dose (cyclophosphamide, 40 mg/kg i.v.; doxorubicin, 3.3 mg/kg i.v.; vincristine, 0.5 mg/kg i.v.; and prednisone, 0.2 mg/kg orally daily for 5 d) weekly for 3 weeks. Rifabutin in an amount of 100 mg/kg was administered on the day of each CHOP treatment and 24-hours later by gavage. Mouse body weight and tumor size were monitored every two days and tumor size measured by caliper. The tumor volume formula (L*W*W)/2 was used to calculate tumor mass.

Figure 5:
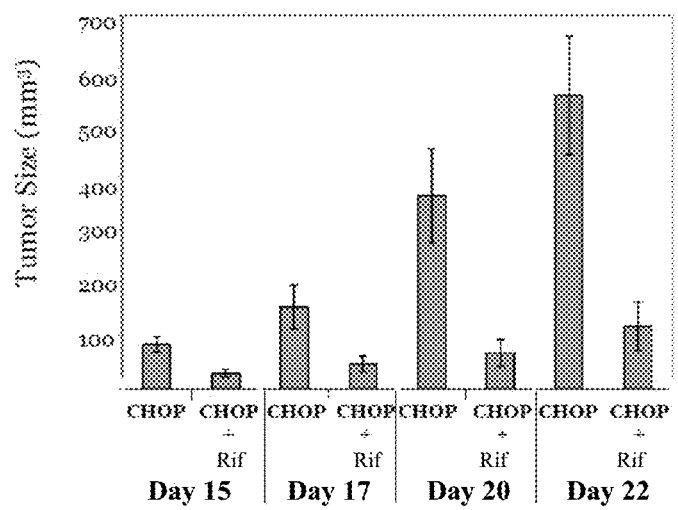
FIG. 5 illustrates the effects of rifabutin in combination with CHOP or CHOP alone on tumor burden in mm³ over time in SCID mice injected with CHOP-resistant (G3) NHL cells.
Figure 6:
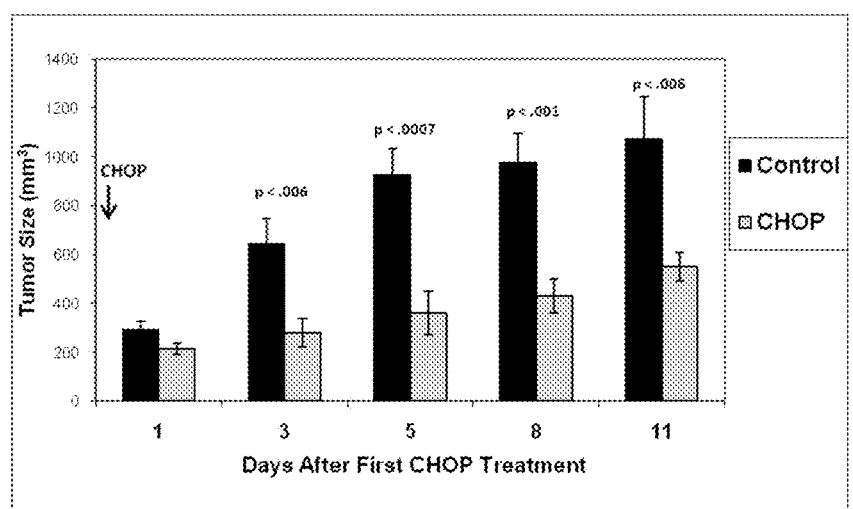
FIG. 6 illustrates the effects of CHOP or control solution with no CHOP on tumor burden in mm³ over time in SCID mice injected with CHOP-sensitive (CRL2631) NHL cells.

The overall tumor burden per mouse was much lower in mice that received CHOP+rifabutin than for those receiving CHOP only treatments. CHOP treatment alone of the SCID mice harboring subcutaneous G3 lymphomas resulted in relatively fast tumor growth, as compared to tumors in CHOP+rifabutin treated mice (FIG. 5). The dosage of rifabutin administered had little or not toxicity in the mice. Control mice injected with CRL2631 cells, in contrast, exhibited a marked decrease in tumor growth in response to CHOP alone (FIG. 6).

A second efficacy study was conducted where mice were treated before the appearance of palpable tumors. In that experiment, one week after transplantation of CHOP-resistant G3 cells, one group (7 mice) was treated with CHOP-only and a second group (8 mice) was treated with CHOP+rifabutin. One week later, mice received a second treatment and tumors began to appear in the CHOP-only group. The two treatment groups differed not only in the tumor size but also in the number of tumors developed. More tumors appeared and grew at a significantly higher rate in CHOP-only mice compared to CHOP+rifabutin mice. The CHOP only treatment group developed tumors at 12 of 14 (85.7%) injection sites. The CHOP+rifabutin treatment group developed fewer tumors at only 6 of 16 (37.5%) injection sites. In a separate experiment, SCID mice developed G3 tumors at 35 of 42 (83.3%) injection sites when receiving no treatment; this is similar to the CHOP only treatment group. Significance was analyzed by the T test yielding a highly significant difference between the means of the tumor burdens of the two groups (p<0.01) at Day 7. Thus, rifabutin actually reduces the tumor take rate which could translate into more complete responses when humans are treated early with this combination.

Figure 7:
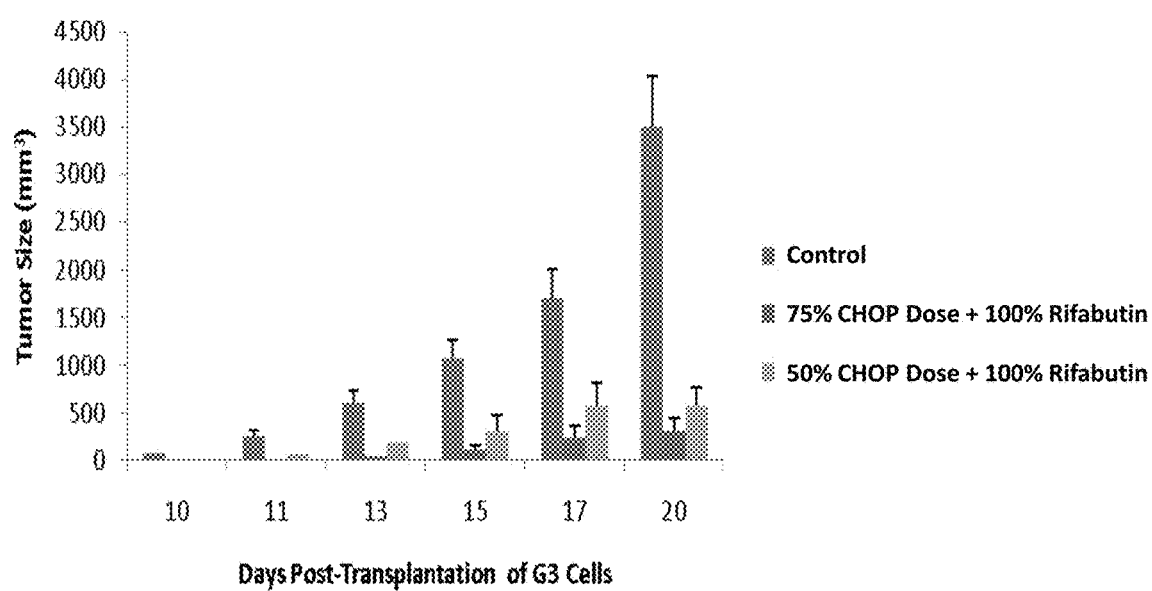
FIG. 7 illustrates the effects of reduced dosages of CHOP+rifabutin or control solution with no CHOP or rifabutin on tumor burden in mm³ over time in SCID mice injected with CHOP-resistant (G3) NHL cells.

A third study was conducted in which mice injected with CHOP-resistant G3 cells received reduced dosages of CHOP in combination with 33 mg/kg rifabutin. CHOP+rifabutin was administered weekly beginning one week post-inoculation. Control mice were given no CHOP or rifabutin. Tumor load was significantly less in mice that received even reduced CHOP dosages as compared to untreated mice, demonstrating that rifabutin may allow the use of lower dosages of CHOP without a significant decrease in therapeutic effect (FIG. 7).

Figure 8:
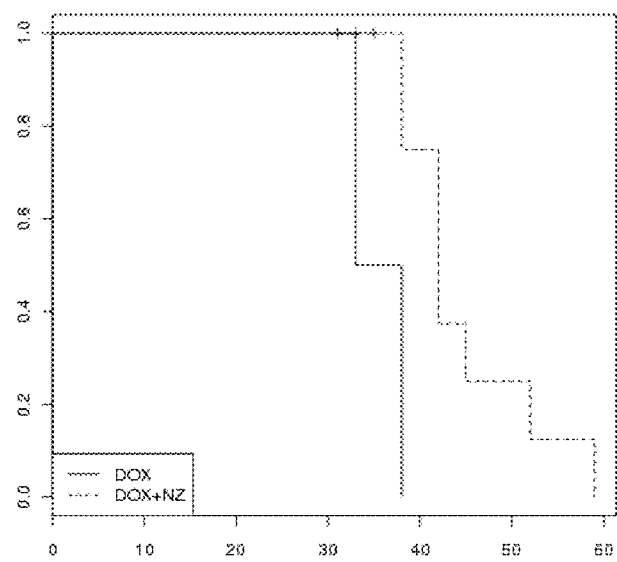
FIG. 8 illustrates a Kaplan-Meier curve showing average life span for SCID mice injected with CHOP-resistant (G3) cells when treated with either doxorubicin alone (DOX) or doxorubicin+rifabutin derivative RTI-81 (DOX+NZ)

A fourth efficacy study was conducted using DOX in combination with the rifabutin derivative RTI-81. SCID mice were injected with CHOP-resistant G3 cells in the same manner as the first efficacy study above. Treatments began 2 weeks post-inoculation and were administered twice weekly. DOX was given at 3.3 mg/kg iv and RTI-81 was given at 10 mg/kg by gavage. A statistically significant difference in average life-span is seen when mice were treated with doxorubicin and RTI-81 as compared to DOX alone. Mice receiving doxorubicin+RTI-81 lived 27% longer than those receiving doxorubicin only ($X^2=8.6$ p=0.00336 (dof=1)) (FIG. 8). Respective mean and median lifespans for each group were: 42.6, 42 and 34.6, 33. Mice treated with doxorubicin only were 10.37 times as likely to die before those treated with doxorubicin+RTI-81. Cox proportional hazard ratio was 0.0964 with a likelihood ratio of 7.24 (p=0.00714 (dof=1, n=15)).

Figure 9:
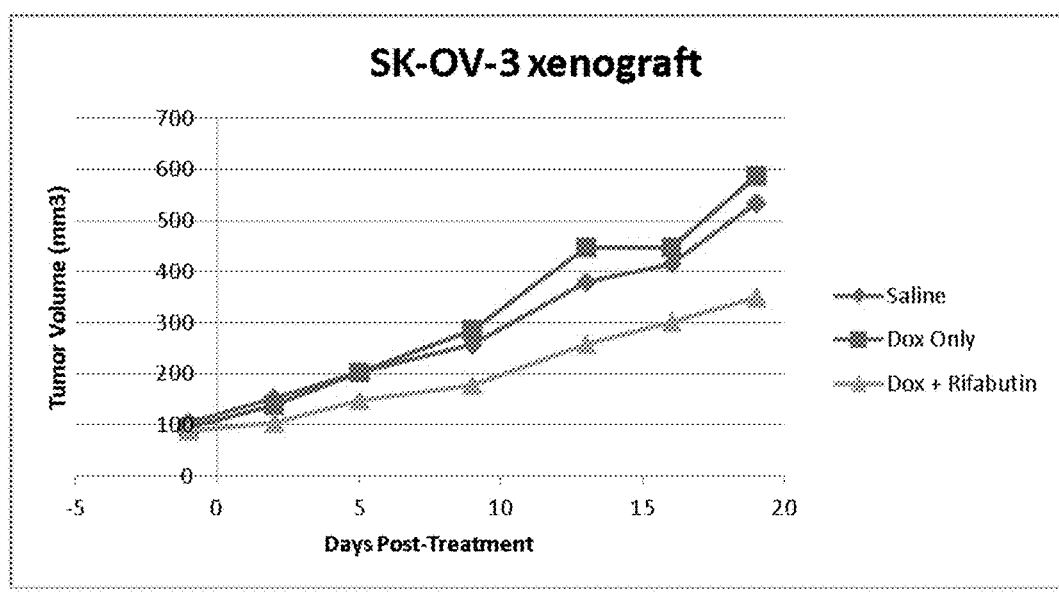
FIG. 9 illustrates the average tumor volume of chemo-resistant SK-OV-3 xenografts in mice after control treatment with saline, treatment with 3.3 mg/kg DOX, and treatment with 3.3 mg/kg DOX+25 mg/kg rifabutin over time.

In a fifth efficacy study, we generated xenografts of the human ovarian cancer cell line SK-OV-3, a cell line considered doxorubicin-resistant, by bilateral subcutaneous (s.c.) injection of $1\times10^7$ tumor cells to establish localized tumors in 6-8 week old female SCID mice. Using rifabutin co-administered with DOX, in vivo efficacy was assessed. Once tumor volumes were at least 75 mm³ and showed consistent growth rates, therapies (DOX only 3.3 mg/kg i.v. or DOX 3.3 mg/kg i.v.+rifabutin 25 mg/kg oral) were started. Cycles of Dox or Dox+rifabutin were given once a week for 4 cycles. This cyclical dosing scheme of mouse models has precedent in the literature and is intended to mimic the cycles of DOXIL® (Centocor Ortho Biotech Products, LP, Raritan, N.J.) given in the clinic. Rifabutin was administered on the day of each DOX treatment and by gavage. Mouse body weight and tumor size were monitored. As shown in FIG. 9, after 19 days treatment, average tumor volumes were 587 mm³ for the DOX-only treatment group, and 348 mm³ for the DOX+rifabutin group. This is a 40% reduction in tumor size for the DOX+rifabutin group.

Figure 10:
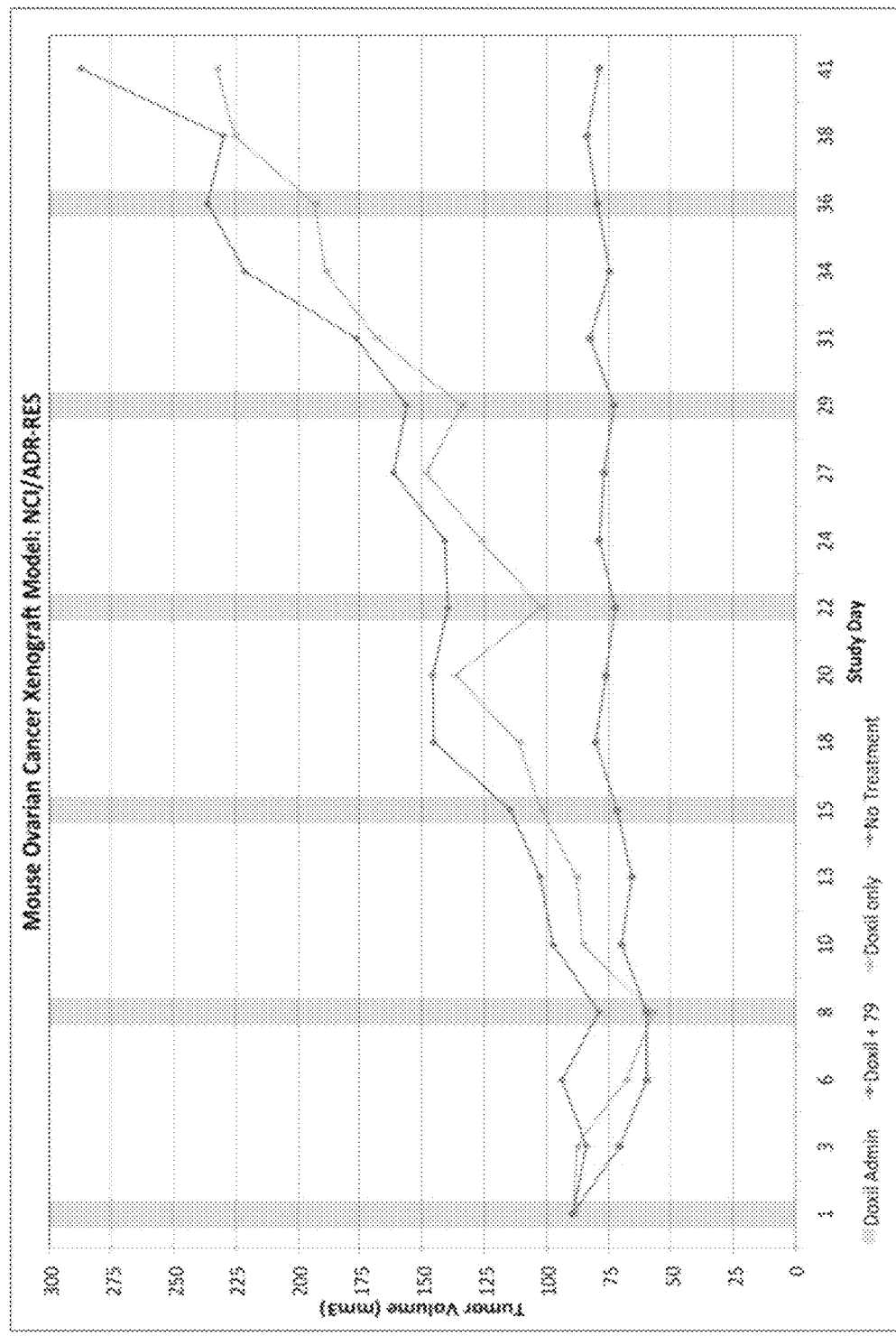
FIG. 10 illustrates the average tumor volume of multi-drug resistant cancer cell line (NCI/ADR-RES) xenografts in mice after control treatment with saline, treatment with 7 mg/kg DOXIL® and treatment with 7 mg/kg DOXIL®+25 mg/kg RTI-79 over time.

In a sixth efficacy study, we generated xenografts of multi-drug resistant ovarian cancer cell line (NCI/ADR-RES) by implantation of NCI/ADR-RES cell xenografts in the left and right flanks of nude mice, resulting in two tumors per mice. In vivo efficacy of RTI-79 was assessed by co-administration with DOXIL®. Once tumor volumes were at least 90 mm³ and showed consistent growth rate, therapies (DOXIL® only 7 mg/kg i.v. or DOXIL®7 mg/kg i.v.+RTI-79 25 mg/kg oral) were started. Cycles of DOXIL® or DOXIL®+RTI-79 were given every week for six cycles. RTI-79 was administered by oral gavage 24 and 48 hours after each DOXIL® administration. Tumor size was monitored. As shown in FIG. 10, after 41 days the tumor volume in the RTI-79-treated mice was 66% lower than in mice receiving only DOXIL®.

Figure 11:
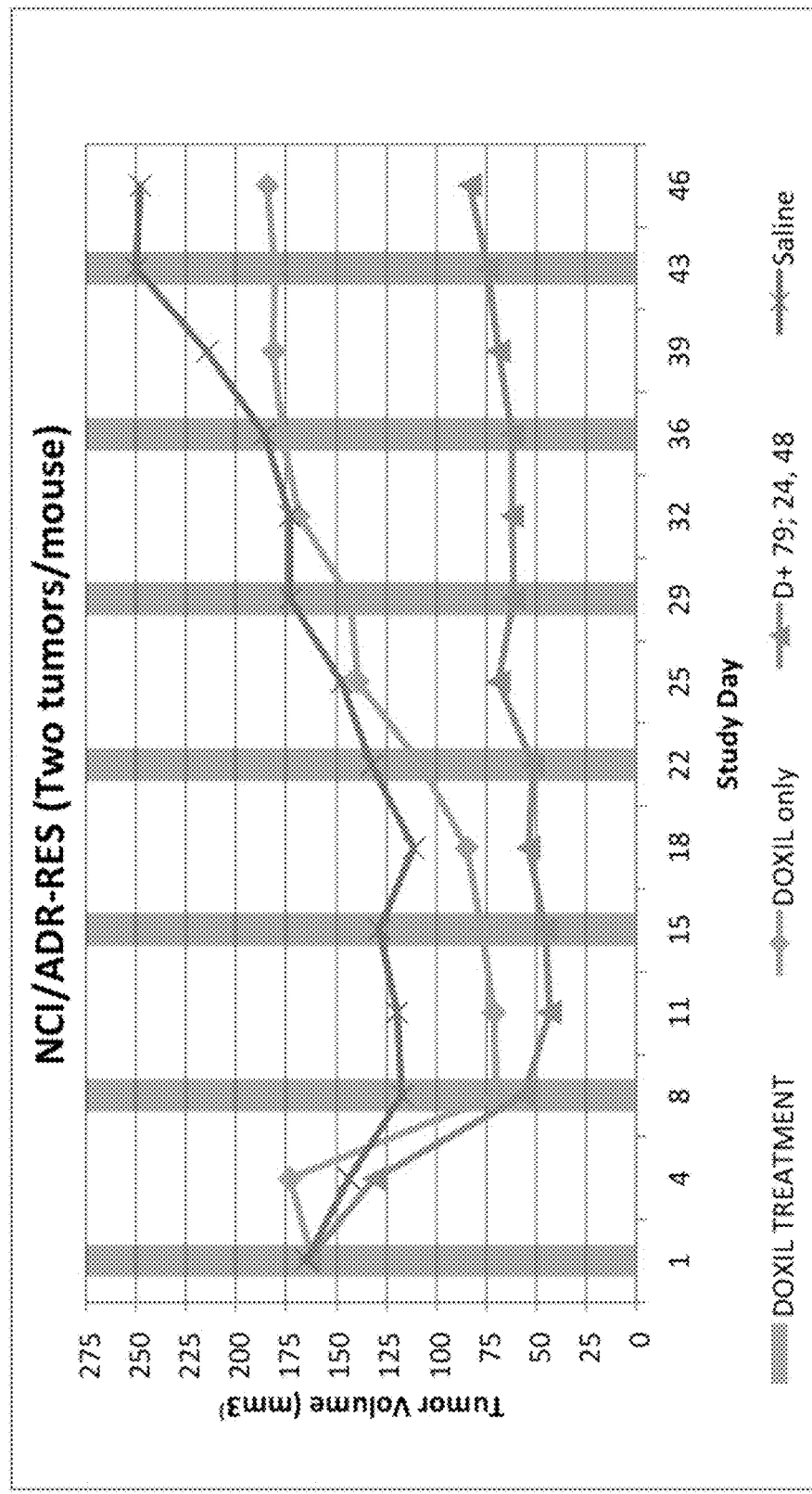
FIG. 11 illustrates the average tumor volume of multi-drug resistant cancer cell line (NCI/ADR-RES) xenografts in mice with multiple, large tumors after control treatment with saline, treatment with 7 mg/kg DOXIL®, and treatment with 7 mg/kg DOXIL®+25 mg/kg RTI-79 over time.

In a seventh efficacy study, we generated xenografts of multi-drug resistant ovarian cancer cell line (NCI/ADR-RES) by implantation of NCI/ADR-RES cells xenografts in the left and right flanks of nude mice, resulting in two tumors per mouse. In vivo efficacy of RTI-79 was assessed by co-administration with DOXIL®. Therapies were DOXIL® only 7 mg/kg i.v. or DOXIL® 7 mg/kg i.v.+RTI-79 25 mg/kg oral. Cycles of DOXIL® or DOXIL®+RTI-79 were given every week for six cycles. RTI-79 was administered by oral gavage 24 and 48 hours after each DOXIL® administration. Tumor size was monitored. As shown in FIG. 11, after 46 days the tumor volume in the RTI-79-treated mice was 55% lower than in mice receiving only DOXIL®. Furthermore, tumor volume in RTI-79-treated mice was reduced by 50% during the course of the study.

Example 5—Sensitization to CHOP Using Other Rifabutin Derivatives

Several compositions of the present disclosure were tested and their effects on cell growth were measured. A reduction in cell growth is demonstrated by a reduction in fluorescence emitted by the cell growth indicator dye, resazurin. Compositions were tested on CHOP-resistant G3 NHL cells that had been cultivated in RPMI medium for five days. Prior to assay, the cells were counted by haemocytometer and cell concentration standardized to 625,000 cells/ml. Test drugs were solubilized in 100% DMSO and then diluted to final assay concentration with 0.1M phosphate buffered saline (PBS) and a final DMSO concentration of 0.5%. Cells were added to assay plates containing the test drugs (rifabutin+ 148 ng/ml, 74 ng/ml, 37 ng/ml, or 0 ng/ml doxorubicin) and allowed to incubate for 96 hours at 37° C. and 5% $CO_2$. The metabolic dye rezasurin was added to the wells of the assay plate at a final concentration of 20 µg/ml and the plates were incubated for an additional 24 hours. The plates were then read in a BMG Polarstar plate reader at wavelength (573-605) and the data plotted as OD versus increasing dilutions (i.e. decreasing total amounts) of rifabutin derivative concentration.

Results of tests were performed on G3 cells to compare the effects of rifabutin and certain rifabutin derivatives on cell growth in the presence or absence of 1 µM doxorubicin (DOX) are presented in Table 2, which indicates the $IC_{50}$s for selected rifamycin analogs on lymphoma cell line G3.

TABLE 2

| $IC_{50}$s for selected rifamycin analogs on lymphoma cell line G3. | | | |
|---|---|---|---|
| Analog | $IC_{50}$ (µM) | $IC_{50}$ (µM) with doxorubicin (1 µM) | Fold increase in potency over DOX alone |
| Doxorubicin | 2.36 | NA | NA |
| Rifabutin | >64 | .25 | 9.4 |
| RTI-51 | >64 | 3.3 | 0.7 |
| RTI-53 | >64 | 11.8 | 0.2 |
| RTI-78 | 58 | 0.08 | 29.5 |
| RTI-79 | 43 | 1.14 | 2.1 |
| RTI-81 | >64 | 0.3 | 7.9 |
| RTI-82 | >64 | 3.5 | 0.7 |
| RTI-102 | >64 | 0.95 | 2.5 |
| RTI-174 | 51 | 0.64 | 3.7 |
| RTI-175 | >64 | 1.06 | 2.2 |
| RTI-176 | >64 | 0.45 | 5.2 |
| RTI-181 | 52 | 0.43 | 5.5 |
| RTI-182 | 62 | 1.2 | 2.0 |
| RTI-183 | >64 | 5.19 | 0.5 |

Figure 12:
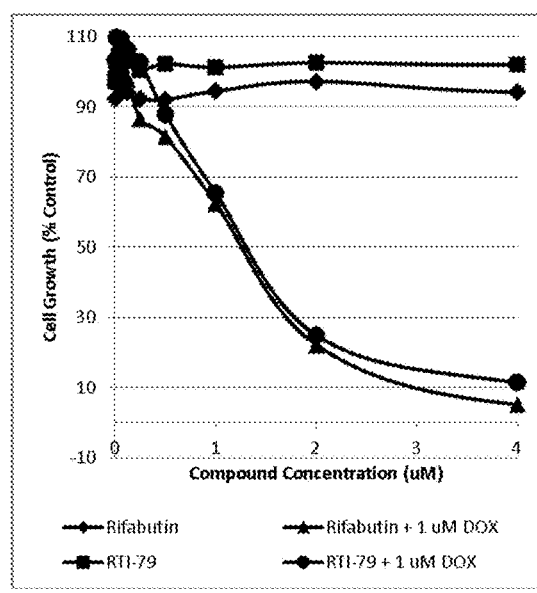
FIG. 12 illustrates the effects of rifabutin or RTI-79 on growth of CHOP-resistant (G3) NHL cells.
Figure 13:
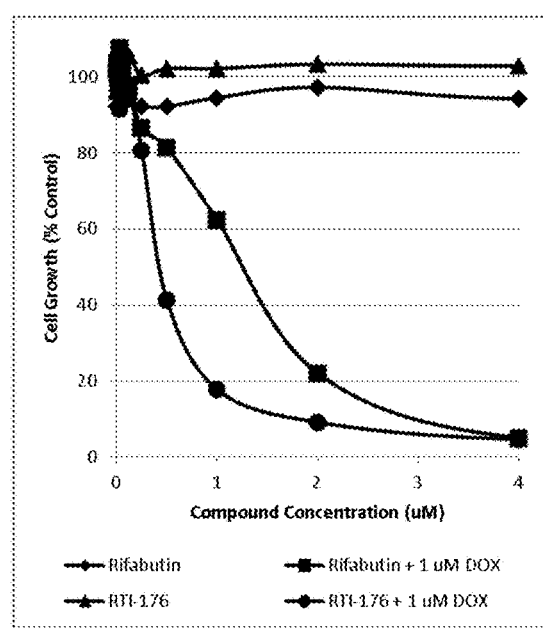
FIG. 13 illustrates the effects of rifabutin or RTI-176 on growth of CHOP-resistant (G3) NHL cells.
Figure 14:
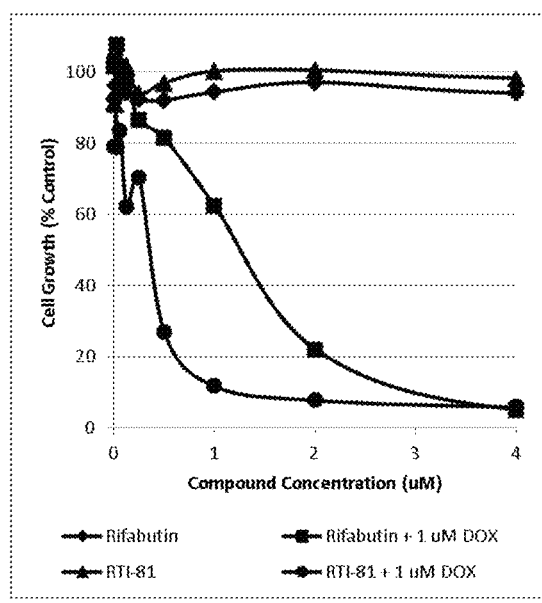
FIG. 14 illustrates the effects of rifabutin or RTI-81 on growth of CHOP-resistant (G3) NHL cells.
Figure 15:
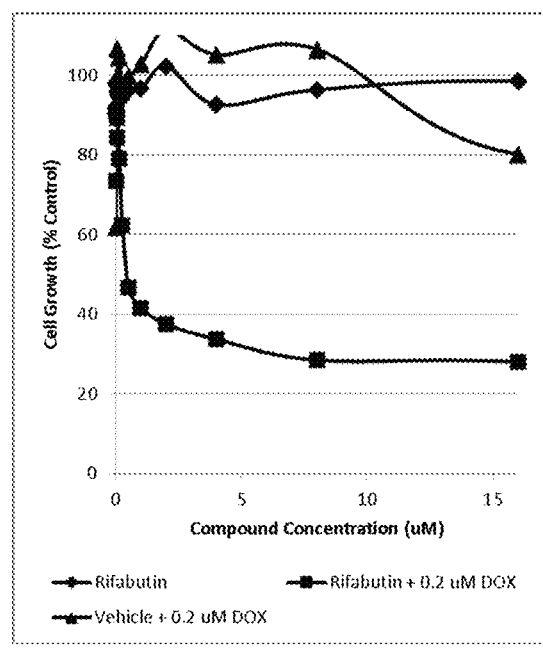
FIG. 15 illustrates the interaction of rifabutin and doxorubicin on CHOP-sensitive (CRL2631) NHL cells.
Figure 16:
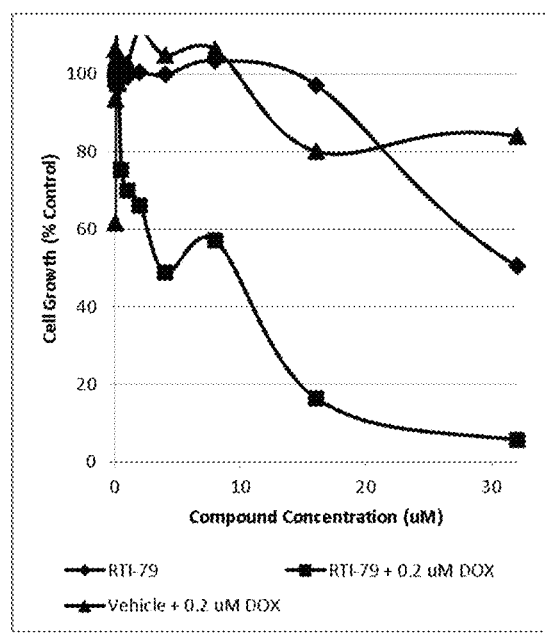
FIG. 16 illustrates the interaction of RTI-79 and doxorubicin on CHOP-sensitive (CRL2631) NHL cells.

Example data for RTI-79 and rifabutin is shown in FIG. 12. Example data for RTI-176 and rifabutin is shown in FIG. 13. Example data for RTI-81 and rifabutin is shown in FIG. 14. Example data for interaction of rifabutin and doxorubicin on CRL2631 cells is shown in FIG. 15. Example data for interaction of RTI-79 and doxorubicin on CRL2631 cells is shown in FIG. 16. These results establish that a variety of rifabutin derivatives are similarly effective at restoring doxorubicin sensitivity to CHOP-resistant cells.

Example 6—Drug-Sensitization of Multiple Cell Lines

The ability of rifabutin and rifabutin derivatives to cause drug-sensitization to doxorubicin in multiple types of cancer cells was investigated by performing experiments similar to those described above. In these experiments, the following cell lines were used: CHOP-resistant NHL cell line G3, CHOP-sensitive NHL cell line CRL2631, the multi-drug resistant sarcoma cell line MES-SA-Dx5; multi-drug-resistant breast cancer cell line MDA-MB-231, multi-drug resistant ovarian carcinoma cell line SK-OV3, multi-drug resistant ovarian cancer cell line NCI/ADR-RES, drug-sensitive ovarian cancer cell line OVCAR-5, and multi-drug resistant ovarian cancer cell line OVCAR-3. Results are presented in Table 3.

TABLE 3

Magnitude of potentiation observed with rifamycin analogs in combination with doxorubicin

| Cancer Type | Tissue | Cell Line | RBT | RTI-51 | RTI-53 | RTI-79 | RTI-81 |
|---|---|---|---|---|---|---|---|
| Lymphoma | B cells | G3 | +++ | | | ++ | +++ |
| Lymphoma | B cells | CRL CRL2631 | | | | | |
| Sarcoma | Uterus | MES-SA-Dx5 | ++ | | | ++ | ++ |
| Carcinoma | Breast | MDA-MB-231 | +++ | | | + | |
| Carcinoma | Ovarian | SK-OV3 | + | + | + | +++ | +++ |
| Carcinoma | Ovarian | OVCAR-3 | | | + | + | + |
| Carcinoma | Ovarian | OVCAR-5 | | | | + | |
| Carcinoma | Ovarian | NCI/ADR-RES | | | | ++ | + |

| Cancer Type | Tissue | Cell Line | RBT | RTI-82 | RTI-102 | RTI-174 | RTI-175 |
|---|---|---|---|---|---|---|---|
| Lymphoma | B cells | G3 | +++ | | ++ | ++ | ++ |
| Lymphoma | B cells | CRL CRL2631 | | | | | |
| Sarcoma | Uterus | MES-SA-Dx5 | ++ | | | | + |
| Carcinoma | Breast | MDA-MB-231 | +++ | +++ | | | |
| Carcinoma | Ovarian | SK-OV3 | + | | +++ | + | +++ |
| Carcinoma | Ovarian | OVCAR-3 | | | | + | + |
| Carcinoma | Ovarian | OVCAR-5 | | | | | ++ |
| Carcinoma | Ovarian | NCI/ADR-RES | | | | + | ++ |

| Cancer Type | Tissue | Cell Line | RBT | RTI-176 | RTI-181 | RTI-182 | RTI-183 |
|---|---|---|---|---|---|---|---|
| Lymphoma | B cells | G3 | +++ | +++ | +++ | + | |
| Lymphoma | B cells | CRL CRL2631 | | | | | |
| Sarcoma | Uterus | MES-SA-Dx5 | ++ | | | | |
| Carcinoma | Breast | MDA-MB-231 | +++ | | | ++ | |
| Carcinoma | Ovarian | SK-OV3 | + | +++ | +++ | ++ | |
| Carcinoma | Ovarian | OVCAR-3 | | | + | + | + |
| Carcinoma | Ovarian | OVCAR-5 | | + | | | |
| Carcinoma | Ovarian | NCI/ADR-RES | | | | | |

Figure 17:
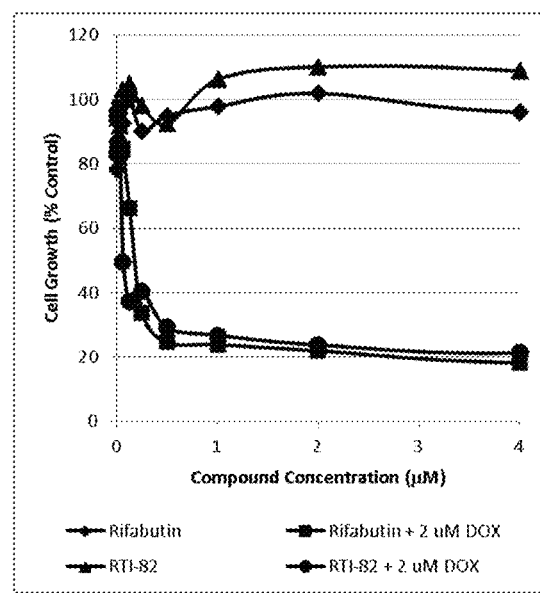
FIG. 17 illustrates the effects of rifabutin or RTI-82 on multidrug-resistant breast cancer (MDA-MB-231) cells.
Figure 18:
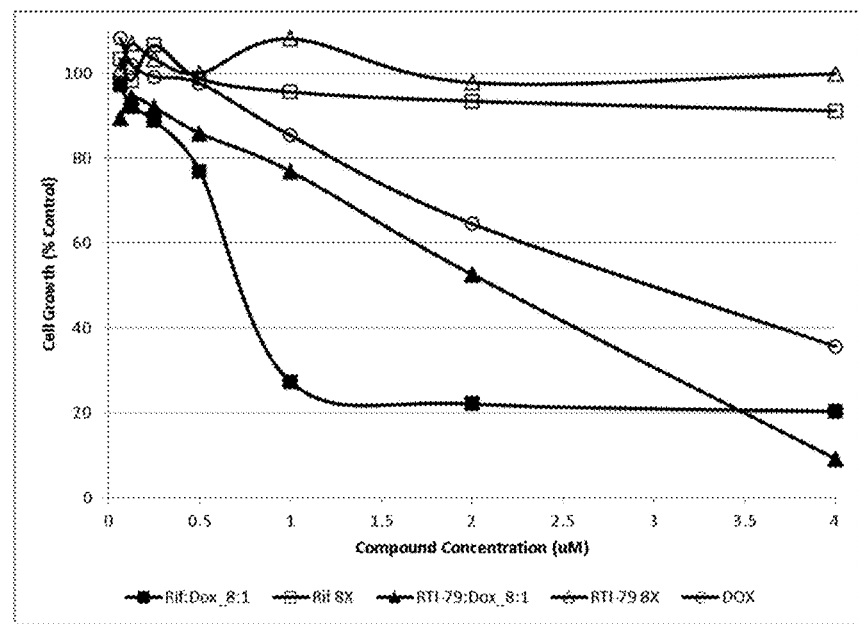
FIG. 18 illustrates the interaction of rifabutin with actinomycin D on multi-drug resistant sarcoma (MES-SA-Dx5) cells.
Figure 19:
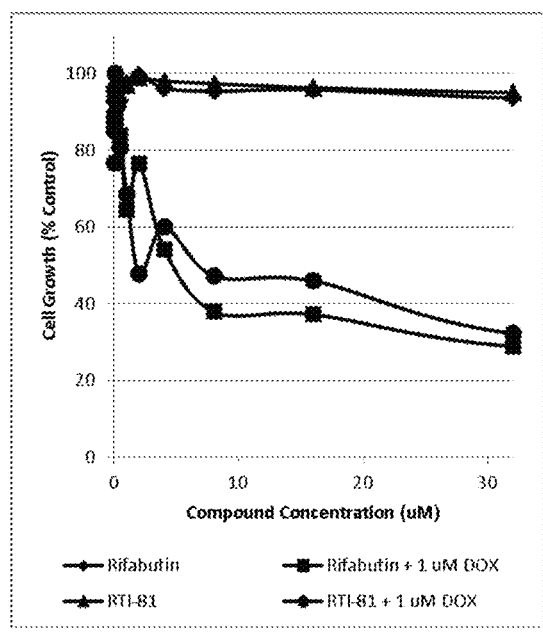
FIG. 19 illustrates the interaction of rifabutin with menadione on dexamethasone resistant multiple myeloma (MM.1R) cells.
Figure 20:
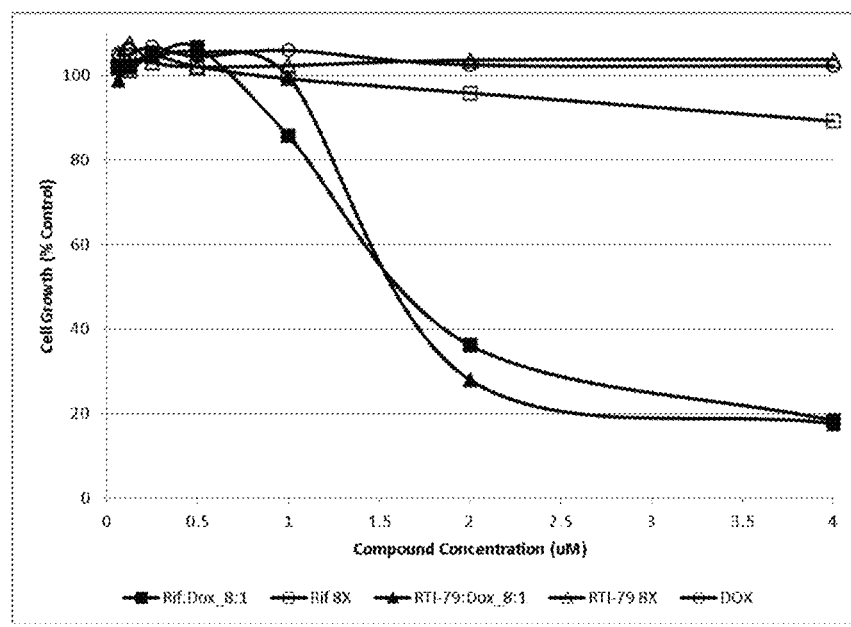
FIG. 20 illustrates the interaction of rifabutin and RTI-79 with and without doxorubicin at an 8:1 rifabutin or RTI-79:doxorubicin molar ratio on multi-drug resistant cancer cell line (NCI/ADR-RES) cells.
Figure 21:
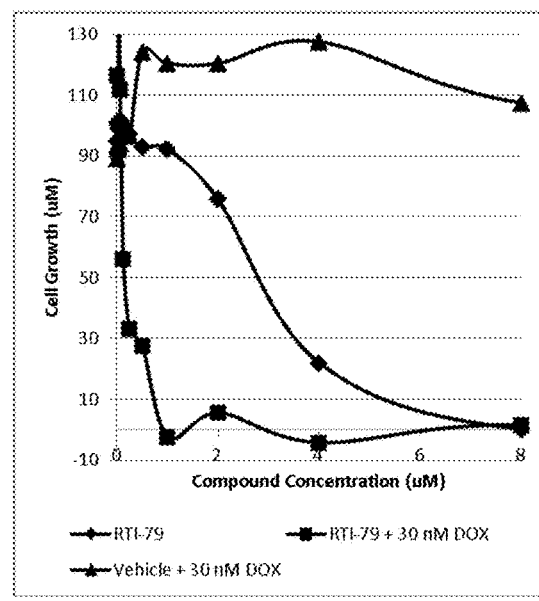
FIG. 21 illustrates the interaction of RTI-79 and doxorubicin on multi-drug resistant T lymphoblastoid leukemia (MOLT-4) cells.
Figure 22:
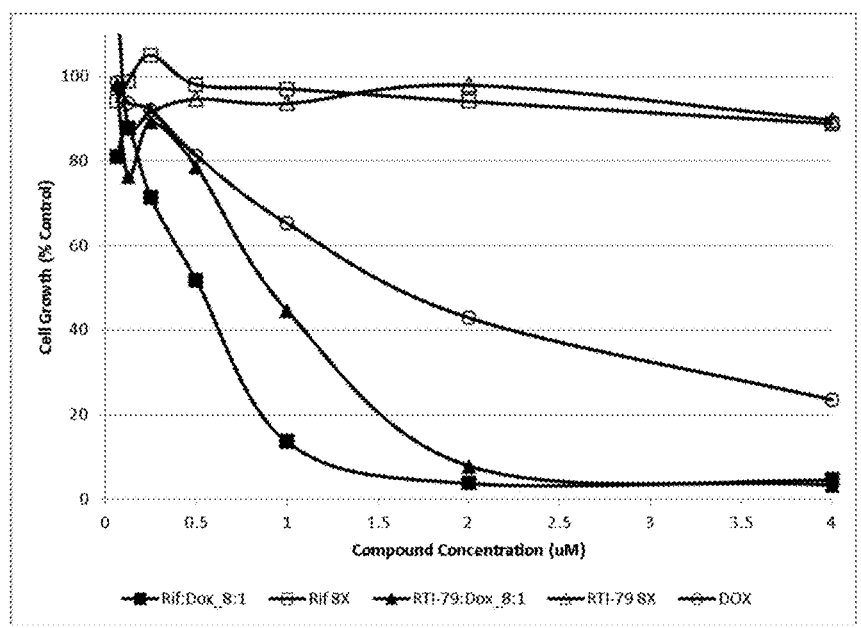
FIG. 22 illustrates the interaction of rifabutin and RTI-79 with and without doxorubicin at an 8:1 rifabutin or RTI-79:doxorubicin molar ratio on ovarian carcinoma (OVCAR8) cells.

RBT = rifabutin;
+ potentiation between 1.2 to 2.0 fold increase;
++ potentiation between 2.1 to 5 fold increase;
+++ potentiation greater than 5 fold increase Example data for rifabutin or RTI-82 on MDA-MB-231 cells is presented in FIG. 17. Example data for rifabutin or RTI-79 with or without doxorubicin on SK-OV3 cells is presented in FIG. 18. Example data for rifabutin or RTI-81 on MES-SA-Dx5 cells is presented in FIG. 19. Example data for interaction of rifabutin or RTI-79 and doxorubicin on ADR-RES cells is shown in FIG. 20. Example data for interaction of RTI-79 and doxorubicin on MOLT-4 cells is shown in FIG. 21. Example data for the interaction of rifabutin or RTI-79 and doxorubicin on ovarian carcinoma OVCAR-8 cells is shown in FIG. 22. These results establish that rifabutin and rifabutin analogs are able to induce drug-sensitization for a variety of types of cancer.

Example 7—Sensitization to Various Chemotherapeutics Using Rifabutin and Rifabutin Derivatives Similar tests were performed to compare the effects of rifabutin and certain rifabutin derivatives on cell growth in the presence or absence of various chemotherapeutics on various cell lines. Chemotherapeutics include: the targeted therapy bortezomib (Velcade®), the pyrimidine antagonist gemcitabine, the platinum drug cis-platin, the anti-tumor antibiotic actinomycin D, the anti-tumor antibiotic apicidin, the topoisomerase I inhibitor camptothecin, the anti-tumor antibiotic doxorubicin, the mitotic inhibitor vinblastine, the nitrogen mustard alkylating agent melphalen, the hormonal agent tamoxifen, the folate antimetabolite methotrexate, the toposimerase II inhibitor etoposide, phenoxodiol, the antibiotic rapamycin, and menadione. Additional cell lines used include: ovarian cancer OVCAR-8, T lymphoblastoid leukemia MOLT-4, dexamethasone-resistant multiple myeloma MM.1R, myeloid leukemia cells HL-60, osteosarcoma cells U-2 OS, and myeloma RPMI 8226. Results are shown in Table 4.

TABLE 4

$IC_{50}$s for selected cancer cell lines and clinically relevant cancer therapeutics in interaction with Rifabutin

| Cancer type | Cell line | Therapeutic drug | $IC_{50}$ (µM) | $IC_{50}$ (µM) with Rifabutin | Fold increase in potency |
|---|---|---|---|---|---|
| Diffuse large B cell lymphoma | G3 | Doxorubicin | 2.36 | 0.25 | 9.4 |

TABLE 4-continued

IC$_{50}$s for selected cancer cell lines and clinically relevant cancer therapeutics in interaction with Rifabutin

| Cancer type | Cell line | Therapeutic drug | IC$_{50}$ (μM) | IC$_{50}$ (μM) with Rifabutin | Fold increase in potency |
|---|---|---|---|---|---|
| Diffuse large B cell lymphoma | G3 | Vinblastine | 8.00 | 1.00 | 8.0 |
| Diffuse large B cell lymphoma | G3 | Mitoxantrone | 0.46 | 0.04 | 11.5 |
| Diffuse large B cell lymphoma | CRL2631 | Doxorubicin | 0.35 | 0.12 | 2.9 |
| Ovarian carcinoma | OVCAR-3 | Menadione | >32 | 10.88 | >2.9 |
| Ovarian carcinoma | OVCAR-5 | Velcade | 0.17 | 0.08 | 2.1 |
| Ovarian carcinoma | OVCAR-8 | Mitoxantrone | 14.0 | 3.0 | 4.7 |
| Ovarian carcinoma | SK-OV3 | Mitoxantrone | >32 | 12.28 | >2.6 |
| Ovarian carcinoma | ADR-RES | Doxorubicin | >32 | 6.59 | >4.9 |
| Leukemia | MOLT-4 | Doxorubicin | 0.03 | 0.01 | 3 |
| Leukemia | MOLT-4 | Actinomycin D | 0.04 | <0.008 | >5 |
| Breast Cancer | MDA-MB-231 | Gemcitabine | >32 | 4.83 | >6.6 |
| Multiple myeloma | MM.1R | Camptothecin | 1.13 | 0.3 | 3.8 |
| Multiple myeloma | MM.1R | Menadione | 4 | 2 | 2 |
| Myeloid leukemia | HL-60 | Paclitaxel | 0.4 | 0.2 | 2 |
| Uterine Sarcoma | MES-SA-Dx5 | Actinomycin D | 0.03 | 0.01 | 3 |
| Osteosarcoma | U-2OS | Mitoxantrone | 0.14 | 0.06 | 2.3 |
| Myeloma | RPMI 8226 | Paclitaxel | 1.0 | 0.89 | 1.1 |

Figure 23:
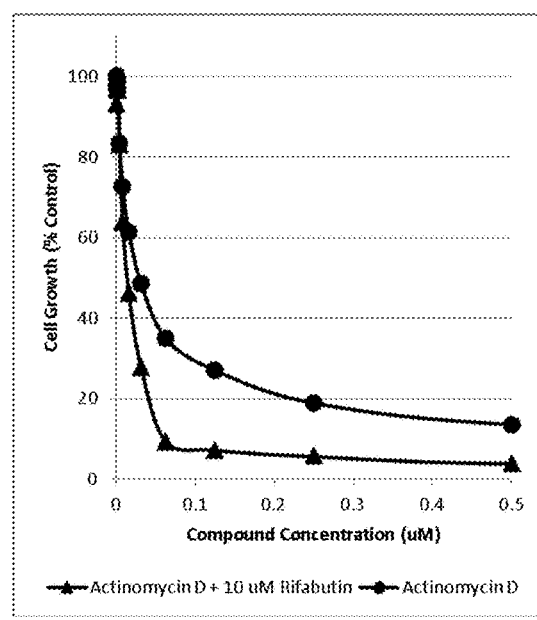
FIG. 23 illustrates the effects of rifabutin and actinomycin D on multi-drug resistant sarcoma (MES-SA-Dx5) cells.
Figure 24:
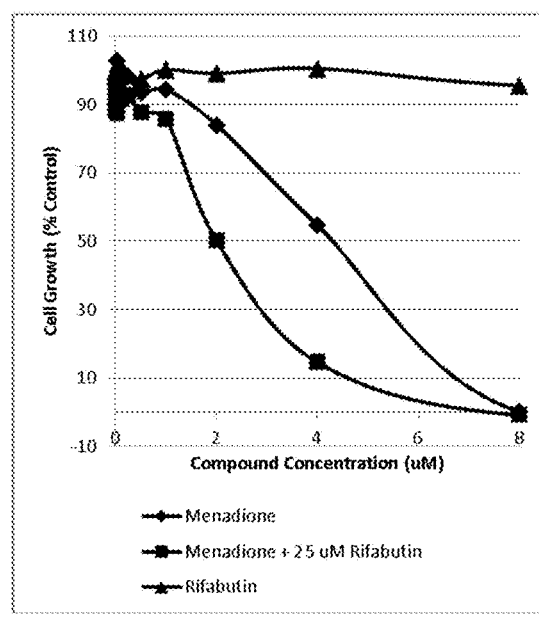
FIG. 24 illustrates the effects of rifabutin and menadione on dexamethasone resistant multiple myeloma (MM.1R) cells.
Figure 25:
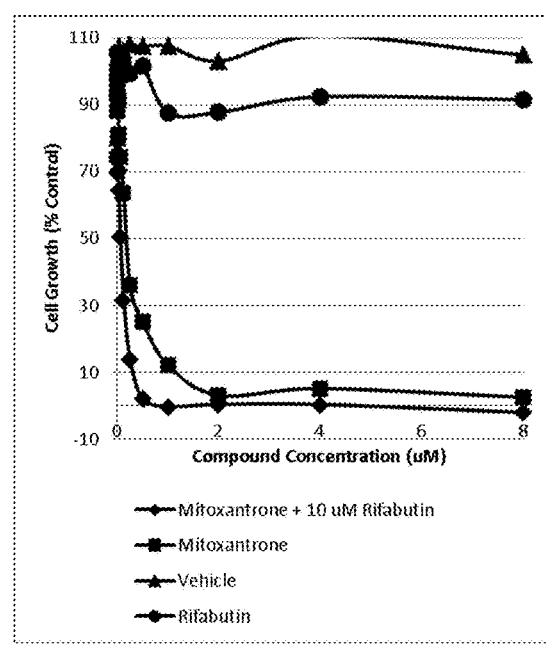
FIG. 25 illustrates the interaction of rifabutin and mitoxantrone on osteosarcoma (U-2 OS) cells.
Figure 26:
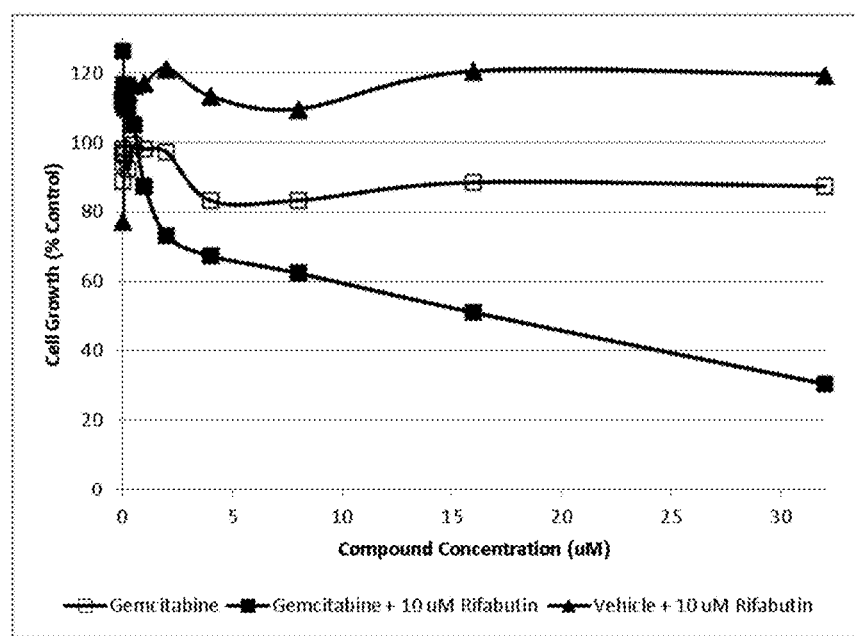
FIG. 26 illustrates the interaction of rifabutin with gemcitabine on multi-drug resistant breast cancer (MDA-MB-231) cells.
Figure 27:
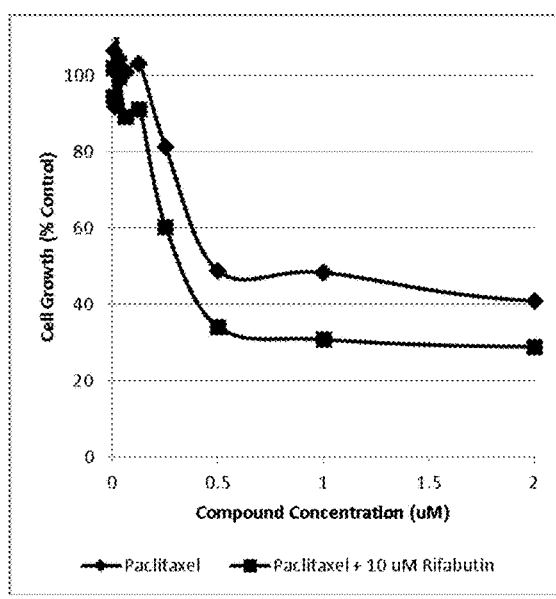
FIG. 27 illustrates the interaction of rifabutin with paclitaxel on myeloid leukemia cells (HL-60) cells.
Figure 28:
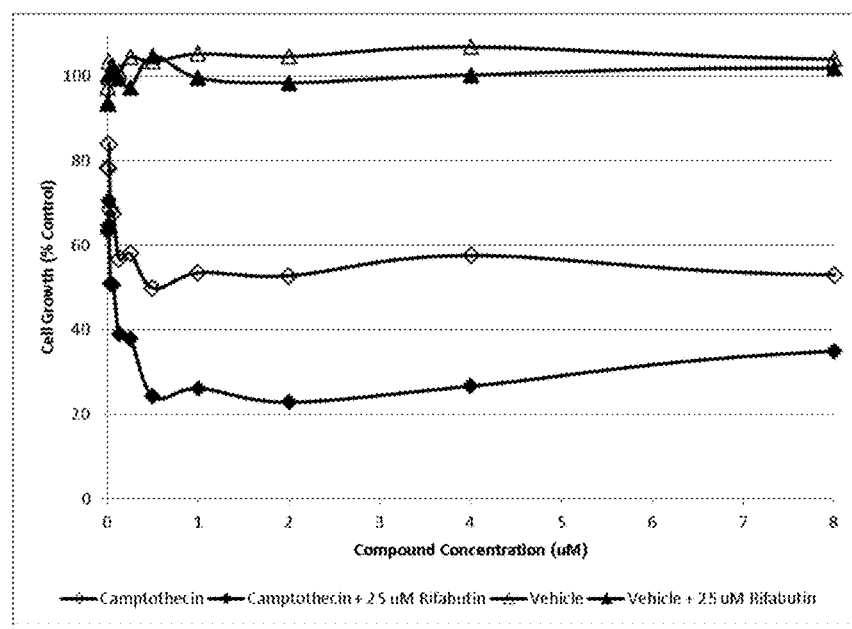
FIG. 28 illustrates the interaction of rifabutin and camptothecin on ovarian cancer (OVCAR-8) cells.

Example data for interaction of rifabutin with actinomycin D on MES-SA-Dx5 cells is shown in FIG. 23. Example data for interaction of rifabutin with menadione on MM.1R cells is shown in FIG. 24. Example data for interaction of rifabutin and mitoxantrone on U-2 OS cells is shown in FIG. 25. Example data for interaction of rifabutin andgemcitabine on MDA-MB-231 cells is shown in FIG. 26. Example data for interaction of rifabutin with paclitaxel on HL-60 cells is shown in FIG. 27. Example data for interaction of rifabutin and camptothecin on OVCAR-8 cells is shown in FIG. 28. These results demonstrate the ability of rifabutin and rifabutin derivatives to induce drug-sensitivity for a wide variety of chemotherapeutics in a wide variety of cancers.

Example 8—Prevention of the Emergence of CHOP Resistance

Figure 29:
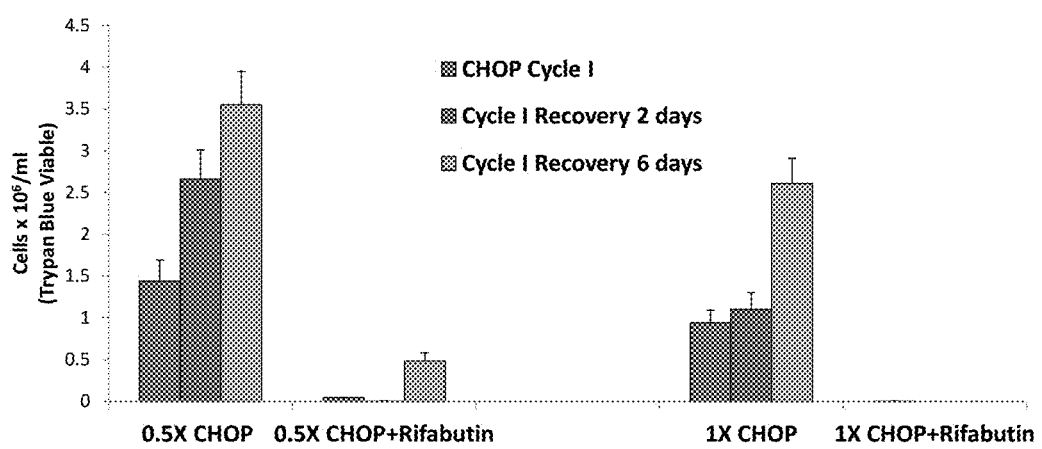
FIG. 29 illustrates the number of viable cells present after re-exposure to CHOP of CHOP-sensitive (CRL2631) cells to a full or half dose of CHOP in the presence or absence of rifabutin.

The ability of rifabutin to prevent the emergence of CHOP-resistance was determined by treating CHOP-sensitive CRL2631 cells with either CHOP alone or CHOP+ rifabutin for one week. Following treatment, the cells were grown in the absence of CHOP, then their sensitivity to CHOP was assayed by retreatment with CHOP, followed by counting of viable cells. Results are shown in FIG. 29. Rifabutin was able to significantly repress the emergence of CHOP-resistant cells at both half (0.5×) and full (1×) doses of CHOP. A 1× CHOP dose in this experiment corresponds to final concentrations of the following components: 0.83 μM 4-hydroxycyclophosphamide [4 HC, a pre-activated form of cyclophosphamide], 0.057 μM doxorubicin, 0.01 μM vincristine, and 0.186 μM prednisone.

Example 9—Effects of Rifabutin and Rifabutin Derivatives on ROS

Figure 30A:
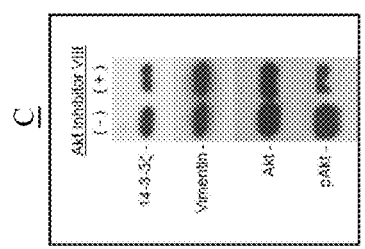
FIG. 30A illustrates a Western blot for phosphorylated Akt (pAkt) Akt, 14-3-3ζ and an actin control in CHOP-sensitive (CRL2631) and CHOP-resistant (G3) cells.
Figure 30C:
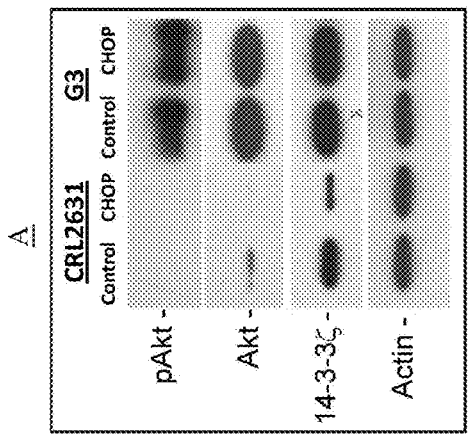
FIG. 30C illustrates a Western blot for phosphorylated Akt (pAkt) Akt, 14-3-3ζ and a Vimentin control in G3 cells exposed or not exposed to Akt Inhibitor VIII.
Figure 30B:
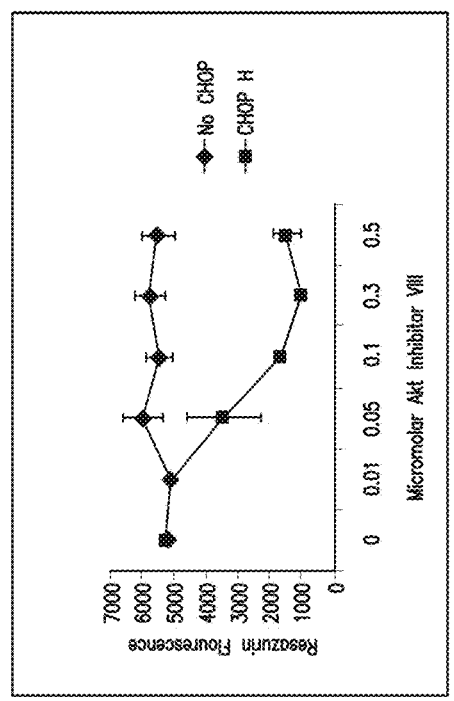
FIG. 30B illustrates the effect of varying amounts of Akt Inhibitor VIII on growth of G3 cells as demonstrated by resazurin fluorescence.

A Western blot of CHOP-sensitive (CRL2631) or CHOP-resistant (G3) lymphoma cells revealed that Akt, phosphorylated Akt, and 14-3-3ζ levels were consistent with the model proposed in FIG. 1 (FIG. 30A) in that Akt was markedly more active in CHOP-resistant G3 cells than in CRL2631. The model was further confirmed by treatment of CHOP-resistant (G3) cells with Akt Inhibitor VIII, which caused a dose-dependent reversal of CHOP resistance (FIG. 30B). The inhibitory effect of Akt inhibitor VIII on the expression of phosphorylated Akt and total 14-3-3ζ protein was confirmed by Western blot (FIG. 30C).

Figure 31:
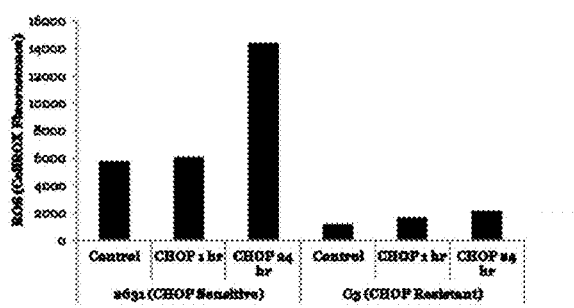
FIG. 31 illustrates the amount of ROS in CHOP-sensitive (CRL2631) or CHOP-resistant (G3) cells before or after 101 ng/ml CHOP treatment (cyclophosphamide=240 ng/ml [0.83 uM]; Doxorubicin=33 ng/ml [0.057 uM]; Vincristine=0.93 ng/ml [0.0045 uM]; Prednisone=67 ng/ml [0.828 uM].

Additional studies further confirmed the model of FIG. 1 by demonstrating that CHOP-sensitive (CRL2631) cells make more ROS than do CHOP-resistant (G3 cells) (FIG. 31). Furthermore, CHOP increased ROS in CHOP-sensitive (CRL2631) cells, but not in CHOP-resistant (G3) cells (FIG. 31).

Figure 32:
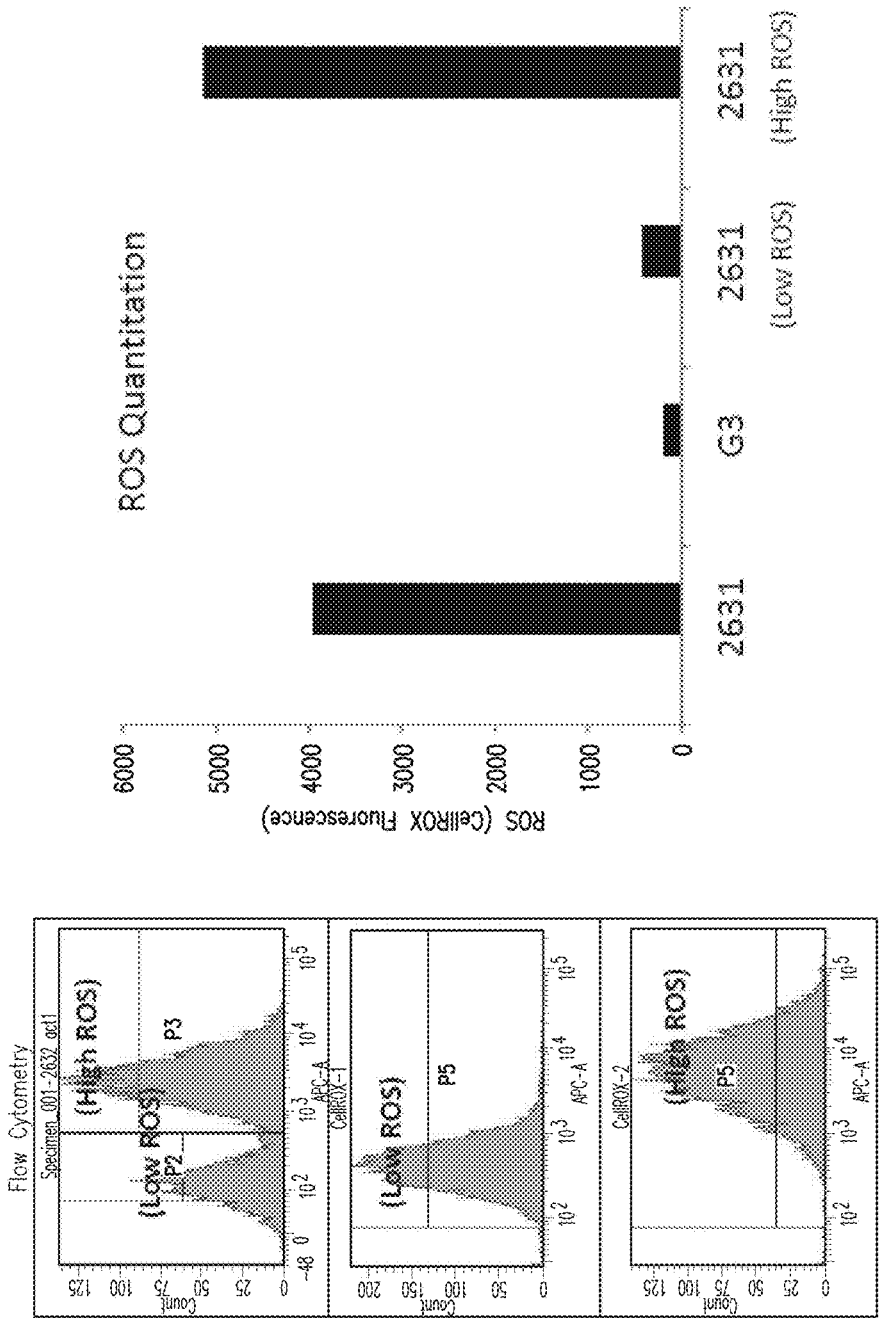
FIG. 32 illustrates the ROS levels in distinct populations of cells in CHOP-sensitive (CRL2631) cells purified by flow cytometry.
Figure 33:
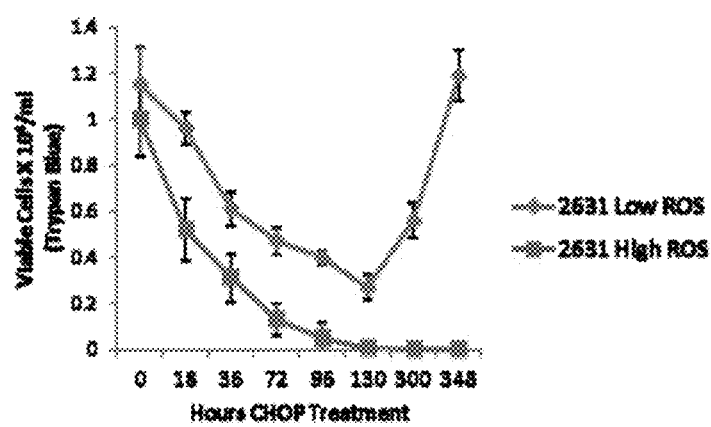
FIG. 33 illustrates the number of viable cells present after treatment of low-ROS CRL2631 cells and high-ROS CRL2631 cells with 101 ng/ml CHOP treatment (cyclophosphamide=240 ng/ml [0.83 uM]; Doxorubicin=33 ng/ml [0.057 uM]; Vincristine=0.93 ng/ml [0.0045 uM]; Prednisone=67 ng/ml [0.828 uM]
Figure 34:
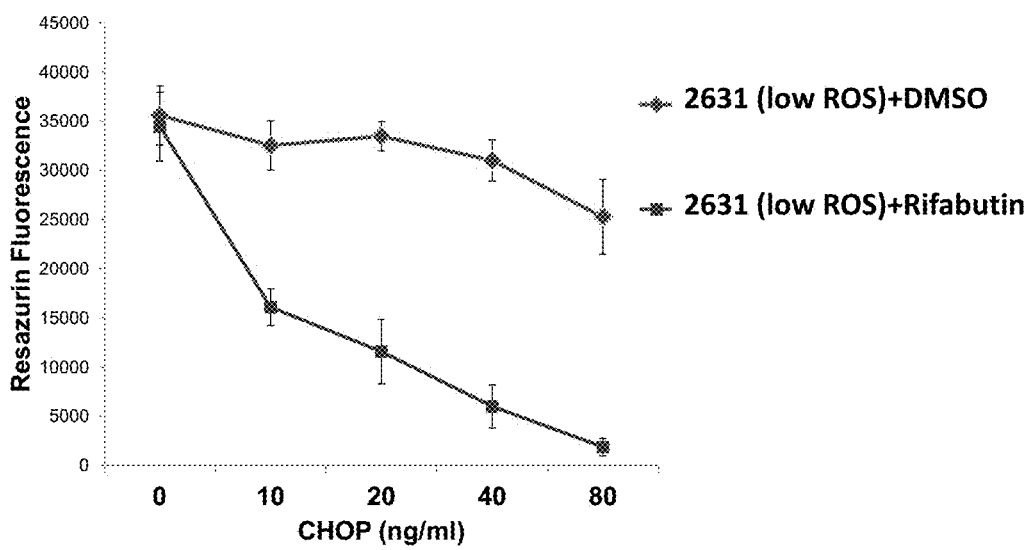
FIG. 34 illustrates the effect on cell growth of varying amounts of CHOP in the presence or absence of 10 uM rifabutin on low-ROS CRL2631 cells as demonstrated by resazurin fluorescence.
Figure 35:
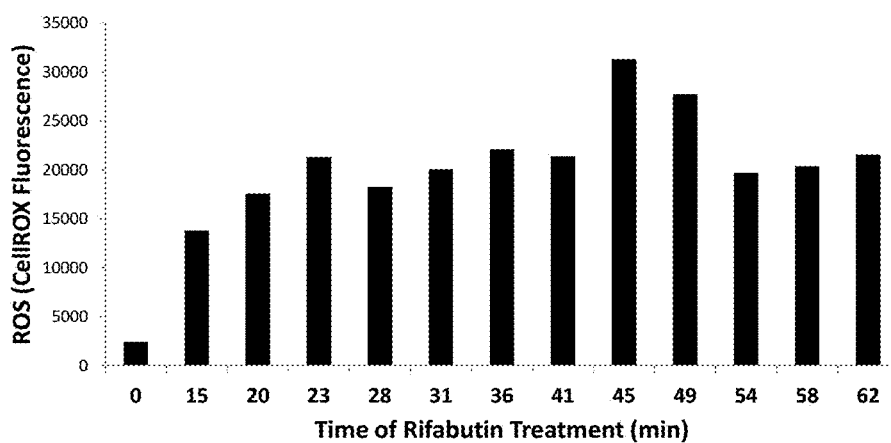
FIG. 35 illustrates the effect of 10 uM rifabutin on ROS in CHOP-resistant (G3) cells over time.

Examination of CHOP-sensitive CRL2631 cells revealed that these cells include two distinct populations, a low-ROS population and high-ROS population (FIG. 32). When these populations were separated, the low-ROS population proved more resistant to CHOP than high-ROS population (FIG. 33). However, this low-ROS cell population was sensitized to CHOP by rifabutin (FIG. 34). Rifabutin also rapidly induces ROS in CHOP-resistant (G3) cells (FIG. 35).

Overall, these results demonstrate that, at least in the CRL2631 lymphoma cell line and cell lines derived therefrom, CHOP-resistance is mediated by ROS levels and that rifabutin and rifabutin derivatives decrease CHOP-resistance by increasing ROS.

Example 10—Rifabutin and RTI-79 Decrease Drug Efflux and Mobilize Calcium

Figure 36A:
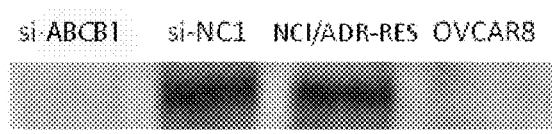
FIG. 36A provides a western-blot showing different ABCB1 protein levels in si-ABCB1 and si-NC1 (control si-RNA) treated ADR-RES cells, as well as the untreated ADR-RES cells and its parental drug-sensitive strain OVCAR8.
Figure 36B:
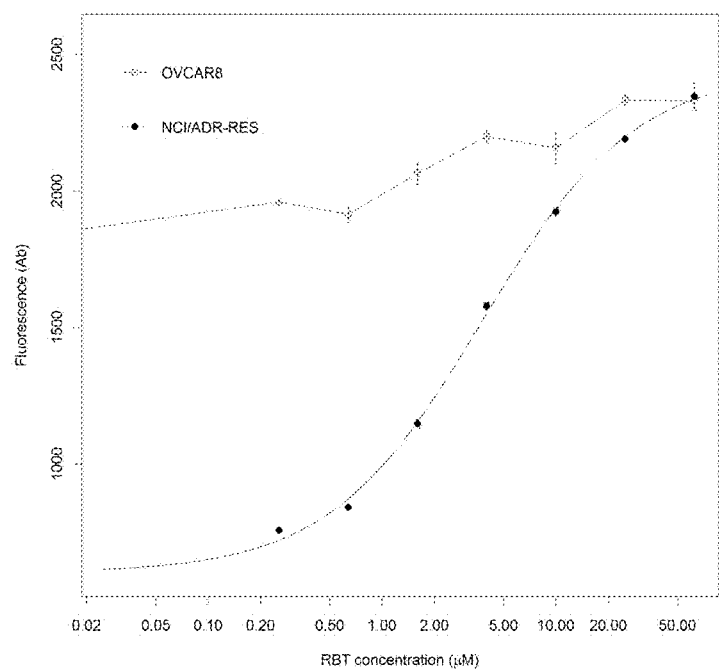
FIG. 36B shows the effects of rifabutin (RBT) on calcein-AM efflux in OVCAR8 than in ADR-RES cells.
Figure 36C:
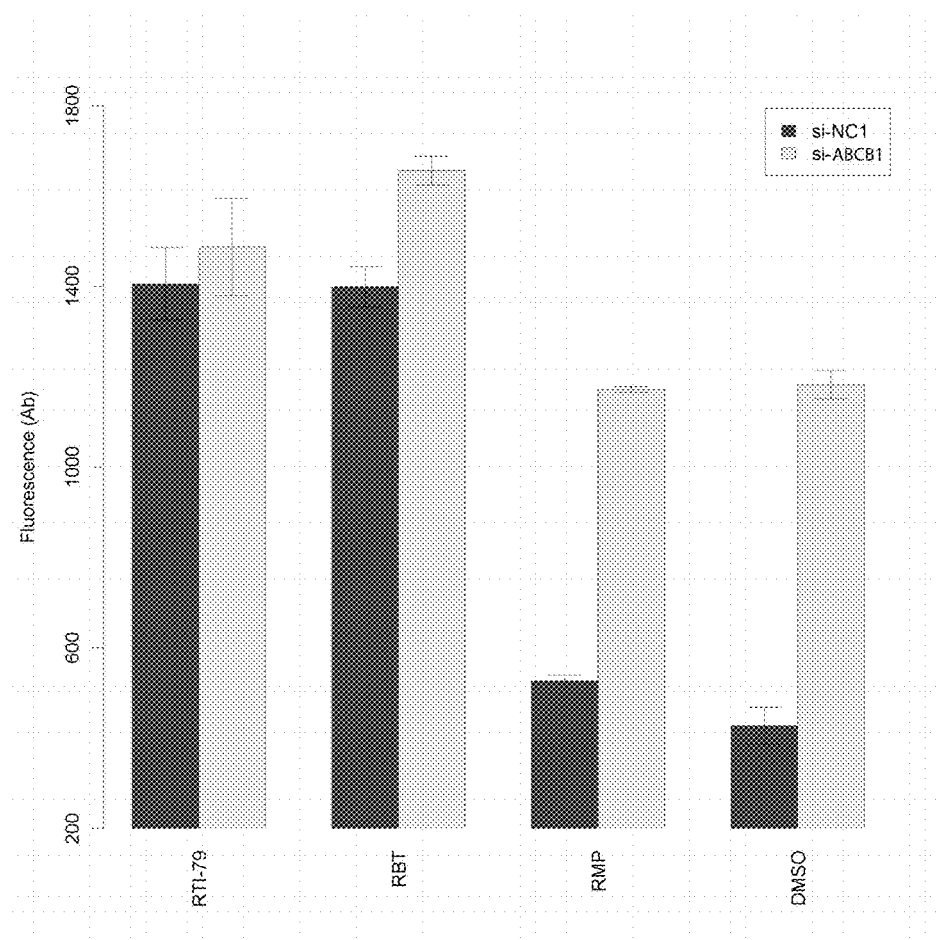
FIG. 36C shows the effects of 5 μM rifabutin (RBT), RTI-79, and rifampin (RMP) on calcein-AM efflux and the further effects of ABCB1 RNA-silencing.
Figure 37A:
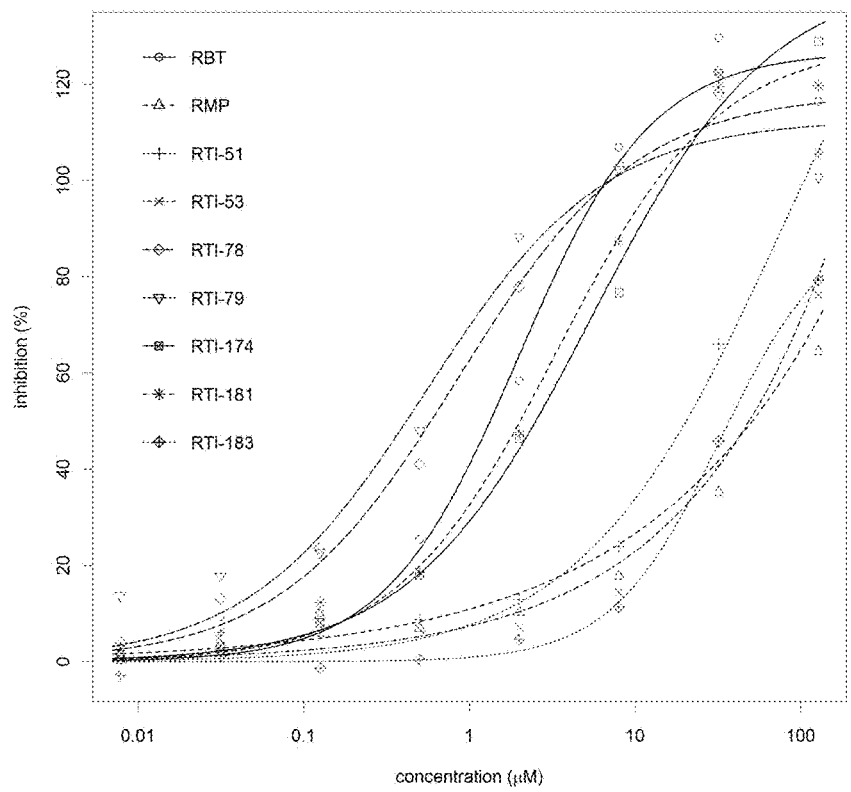
FIG. 37A shows dose-response curves of various RTIs on calcein-AM efflux.
Figure 37B:
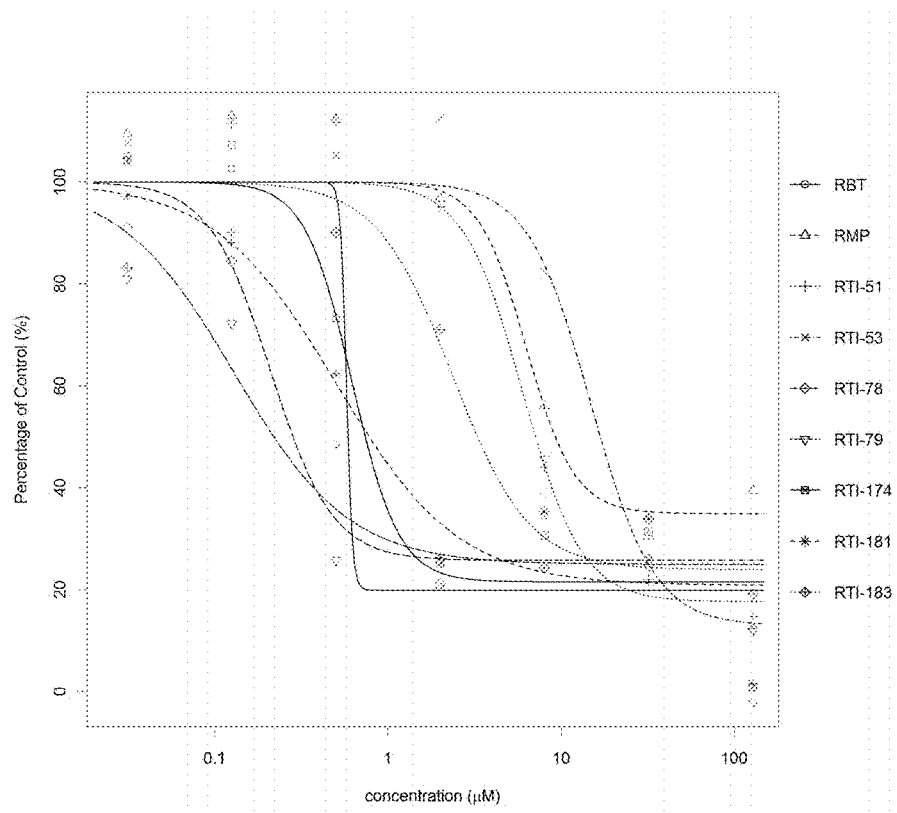
FIG. 37B shows the effects of various RTIs on 1 uM doxorubicin's toxicity in G3 cells.
Figure 37C:
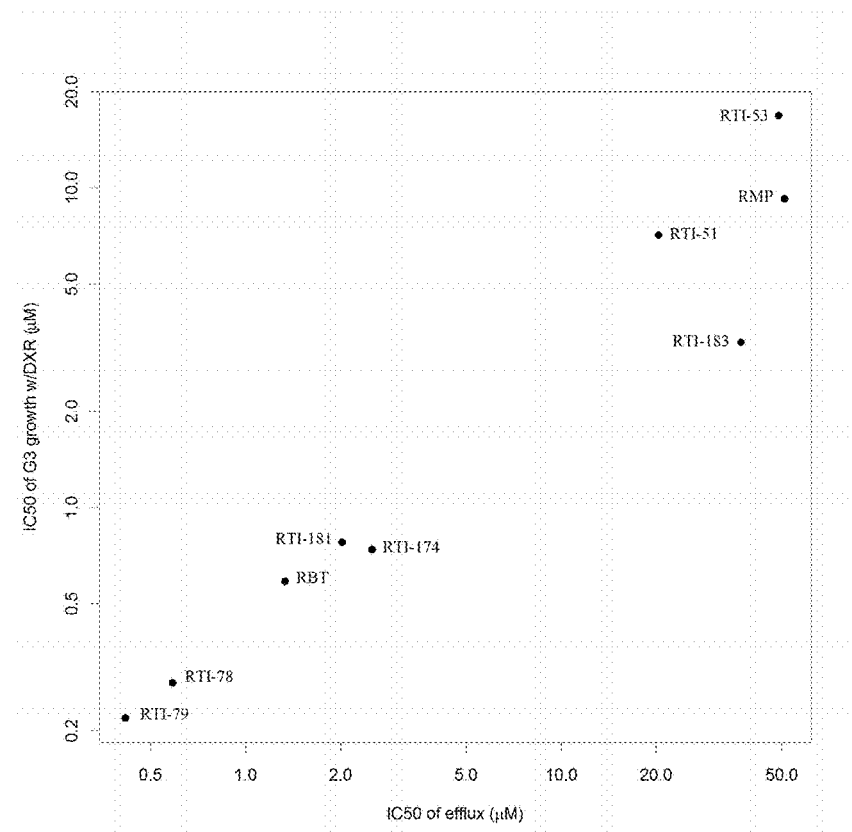
FIG. 37C shows the correlation between efflux inhibition effect and drug sensitizing ability for various RTI-x rifamycin derivatives.
Figure 37D:
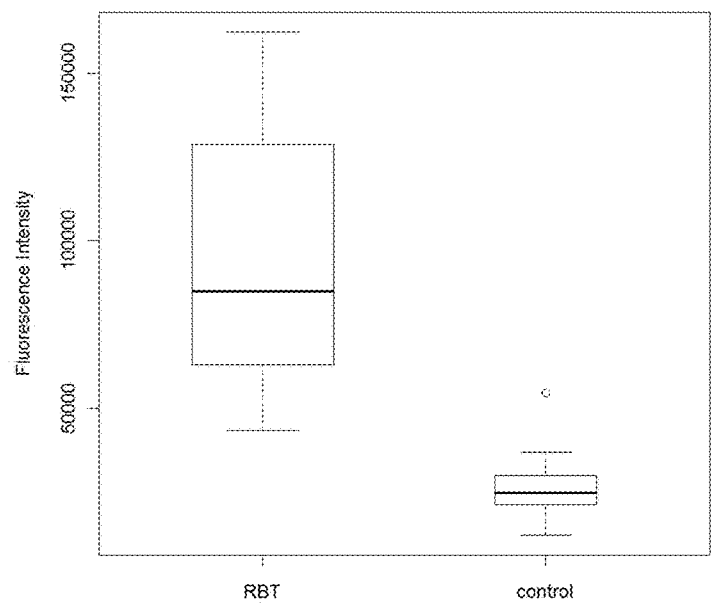
FIG. 37D shows the comparison of doxorubicin fluorescence intensity in the NCI/ADR-RES cells with rifabutin treatment or dimethyl sulfoxide (DMSO) control.

Rifabutin and its derivatives, such as RTI-79, showed clear inhibition of efflux pumps in NCI/ADR-RES and G3 cells when tested in calcein-AM assays. This inhibitory effect was unambiguously due to inhibition of ABCB1 pumps. The difference in pump activity between ADR-RES cells and its drug-sensitive parental strain, OVCAR-8, may be seen in FIGS. 34A and 34B It is known that mitigation of ABCB1 activity will lead to more effective accumulation of doxorubicin in cells (Shen, F., Chu, S., Bence, A. K., Bailey, B., Xue, X., Erickson, P. A., Montrose, M. H., Beck, W. T., and Erickson, L. C. (2008). Quantitation of doxorubicin uptake, efflux, and modulation of multidrug resistance (MDR) in MDR human cancer cells. J Pharmacol Exp Ther 324, 95-102.). Thus the inhibition on ABCB1 by RTI-79 directly contributes to its potentiating doxorubicin toxicity on these drug-resistant cells. This was confirmed by testing with additional rifabutin derivatives. As shown in FIG. 36, the stronger inhibitors of ABCB1, also better re-sensitized drug-resistant cells. RTI-79 was the strongest inhibitor as well as best re-sensitizer.

Figure 38A:
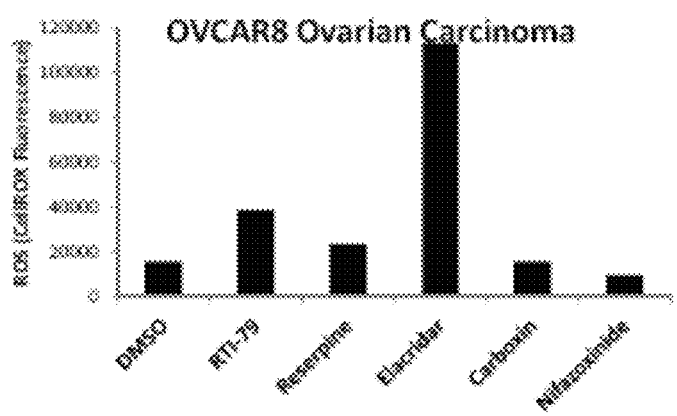
FIG. 38A shows the effects of MDR/P-gp inhibitors and two control drugs (carboxin, nifazoxinide) on ROS in doxorubicin-sensitive OVCAR8 cells.
Figure 38B:
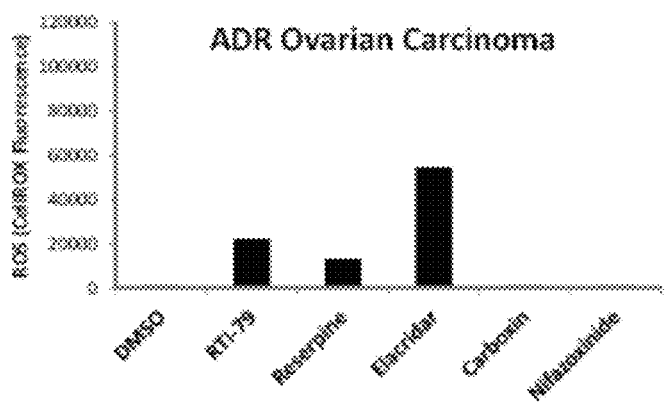
FIG. 38B shows the effects of MDR/P-gp inhibitors and two control drugs (carboxin, nifazoxinide) on ROS in doxorubicin-resistant ADR-RES cells.
Figure 38C:
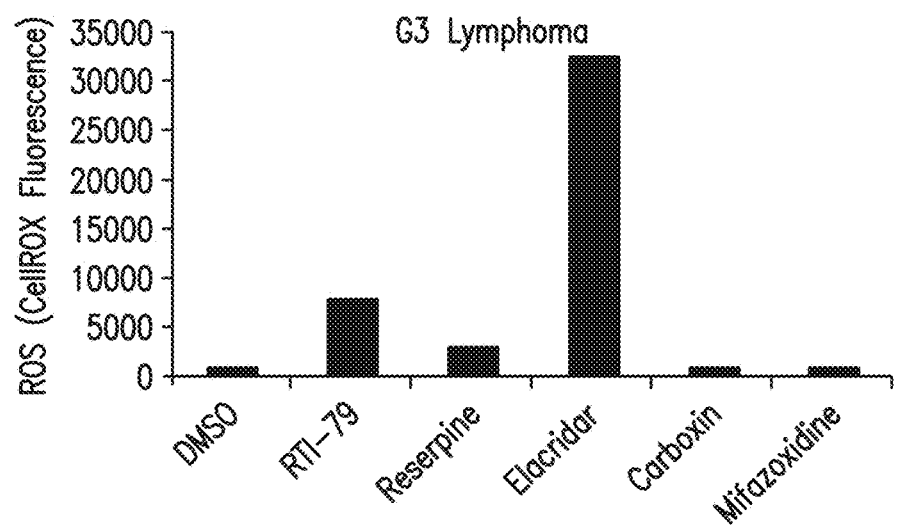
FIG. 38C shows the effects of MDR/P-gp inhibitors and two control drugs (carboxin, nifazoxinide) on ROS in doxorubicin-resistant G3 cells.

Doxorubicin-sensitive (OVCAR8 ovarian) and Doxorubicin-resistant (G3 lymphoma; ADR-RES ovarian) cells were treated for 2 hrs with 10 uM RTI-79, p-glycoprotein (P-gp) inhibitors (reserpine, elacridar), or control drugs (DMSO, carboxin, nifazoxidine). Cells were then stained with the fluorescent ROS indicator, CellROX, and subjected to flow cytometry to quantitate total intracellular ROS. As FIG. 38 shows, RTI-79 induced ROS in ovarian carcinoma and lymphoma cell lines, as did the MDR/P-gp inhibitors, reserpine, elacridar. This suggests that RTI's ability to induce ROS was the result of inhibition of efflux pumps. The degree of ROS induced by RTI-79 and P-gp inhibitors was much greater in the doxorubicin-resistant ADR-RES and G3 cell lines than in the doxorubicin-sensitive OVCAR8 cell line. Control drugs established that this effect is specific to MDR/P-gp inhibitors and RTI-79.

Figure 39:
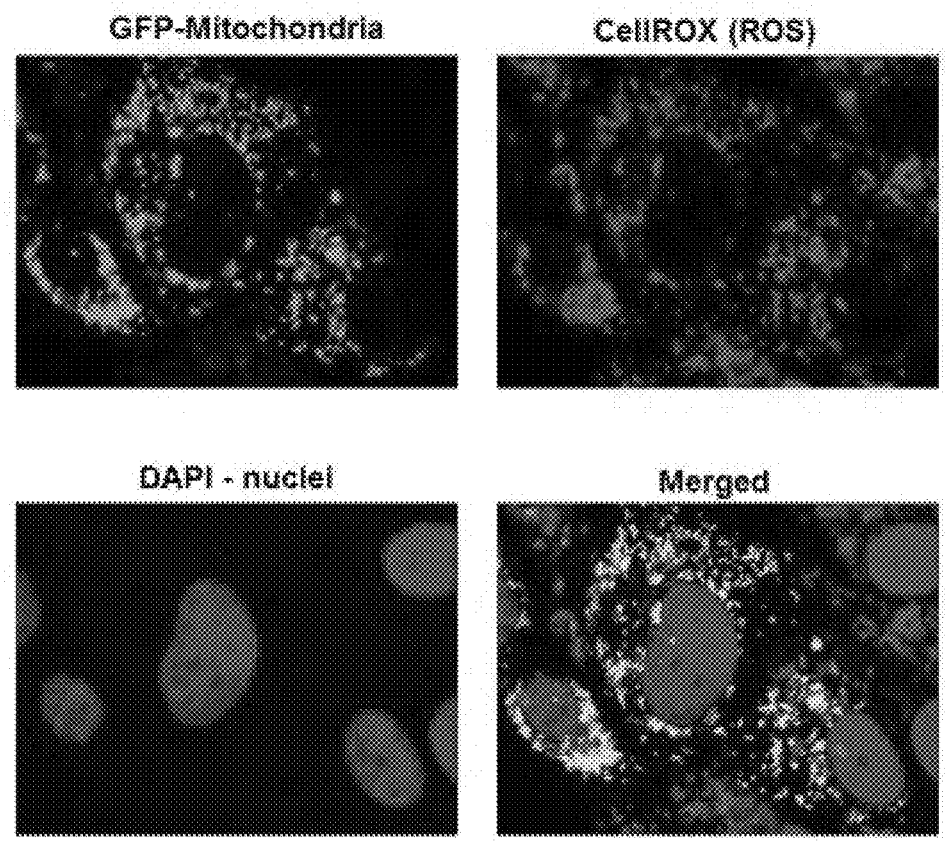
FIG. 39 shows staining of ADR-RES cells treated with RTI-79; ADR-RES cells were infected 24 hrs with a baculovirus expressing a recombinant GFP protein fused with a mitochondrial localization signal (green); cells were stained with CellROX to detect ROS (red) or DAPI to detect nuclei (blue)

The intracellular origin of RTI-induced ROS was determined by staining ADR-RES cells with the red fluorescent ROS indicator, CellROX (Invitrogen), and visualizing where the ROS was concentrated by confocal microscopy. Results are presented in FIG. 39. Mitochondria were localized by infecting cells for 24 hrs with the BacMAM mitotracker baculovirus, which expresses a GFP fused to a mitochondria localization signal. Nuclei were stained with the blue DAPI stain. There was a good co-localization of red CellROX staining with the green GFP mitotracker, indicating that the ROS were originating from the mitochondria.

Figure 40:
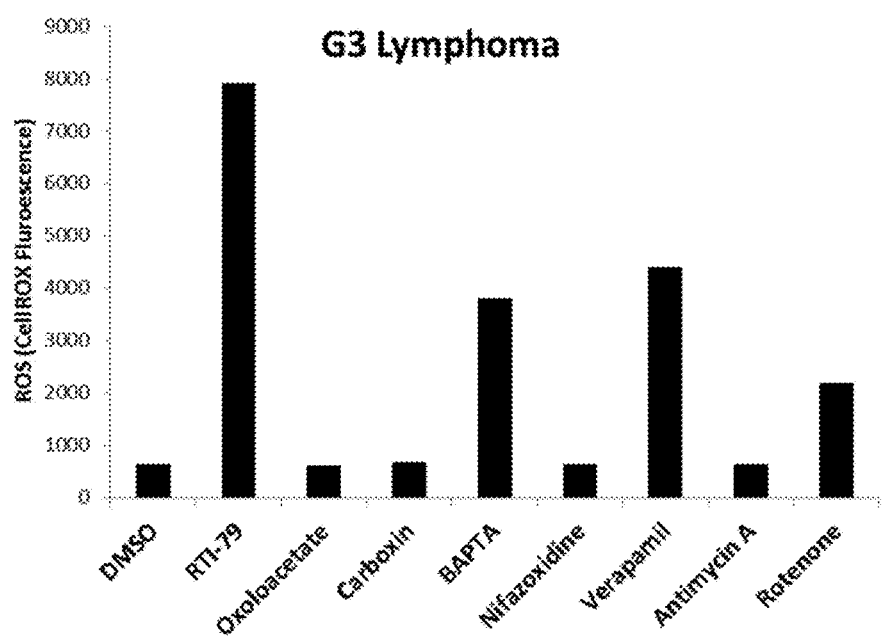
FIG. 40 shows the effects of cell-permeable calcium modulators (BAPTA, Verapamil) and a Complex I inhibitor (Rotenone) on ROS in G3 cells.

The electron transport chain (ETC) is known to be a primary generator of ROS in the cell. Most of the ROS is generated by Complexes I and III of the ETC. Inhibition of Complex I results in electrons piling up and leaking to react with oxygen to produce ROS. The effects of a Complex I inhibitor (rotenone) and a Complex III inhibitor (antimycin A) on ROS levels in the cell were tested and results are shown in FIG. 40. Specifically, Dox-resistant G3 lymphoma cells were treated 10 uM RTI-79, BAPTA-AM (cell permeable calcium chelator), verapamil (a calcium channel blocker and P-gp inhibitor), a Complex I inhibitor (Rotenone), a Complex III inhibitor (antimycin A), or control drugs (oxaloacetate, carboxin, nifazoxinide). Rotenone, but not antimycin A, induced ROS, suggesting that RTI-79-induced and efflux pump inhibitor-induced ROS originate at Complex I of the ETC.

Figure 41A:
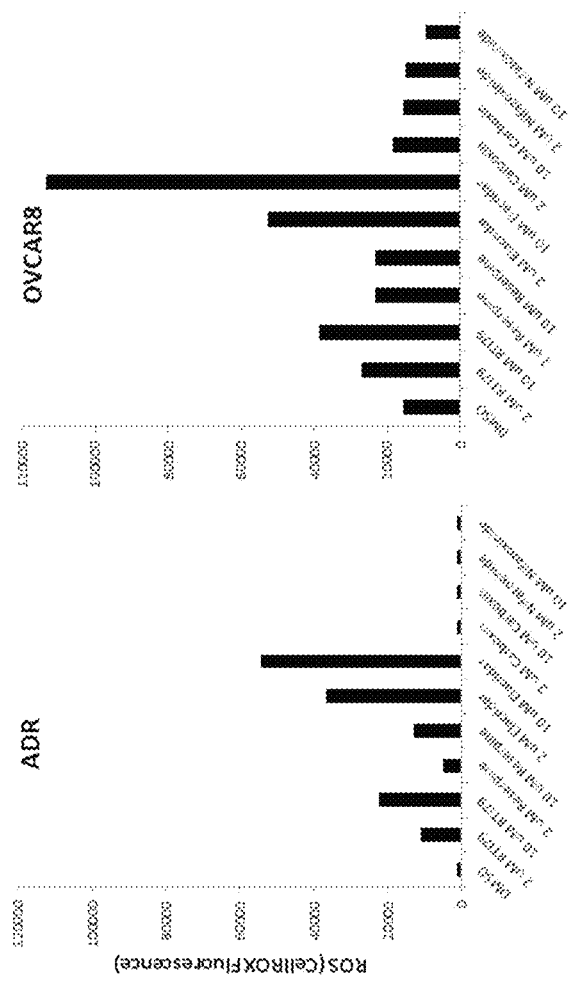
FIG. 41A shows the effects of P-gp inhibitors (Reserpine, Elacridar) on ROS levels in ADR and OVCAR8 cells
Figure 41B:
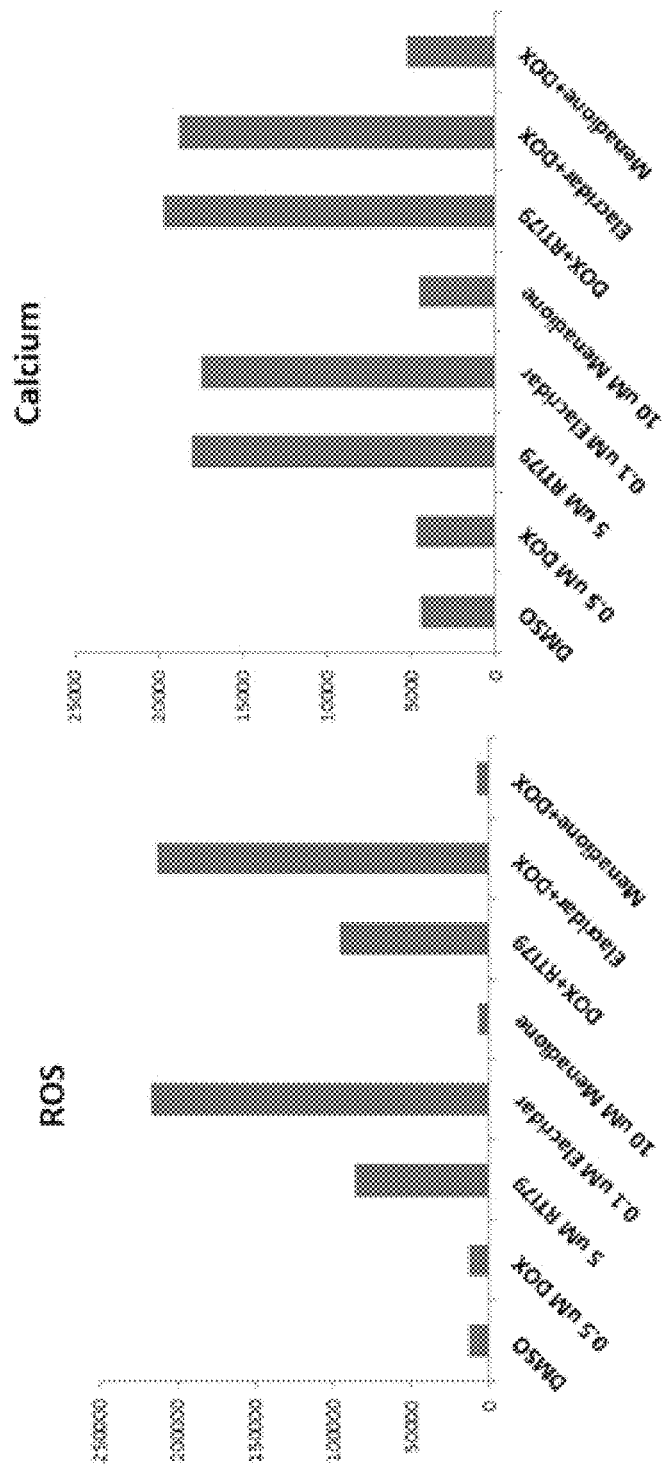
FIG. 41B shows the effects of RTI-79 on ROS and calcium mobilization in doxorubicin-sensitive lymphoma (CRL2631, 10S, WSU) and ovarian carcinoma (OVCAR8) cells and doxorubicin-resistant lymphoma (G3R, 10R, WSUR) cells.
Figure 41C:
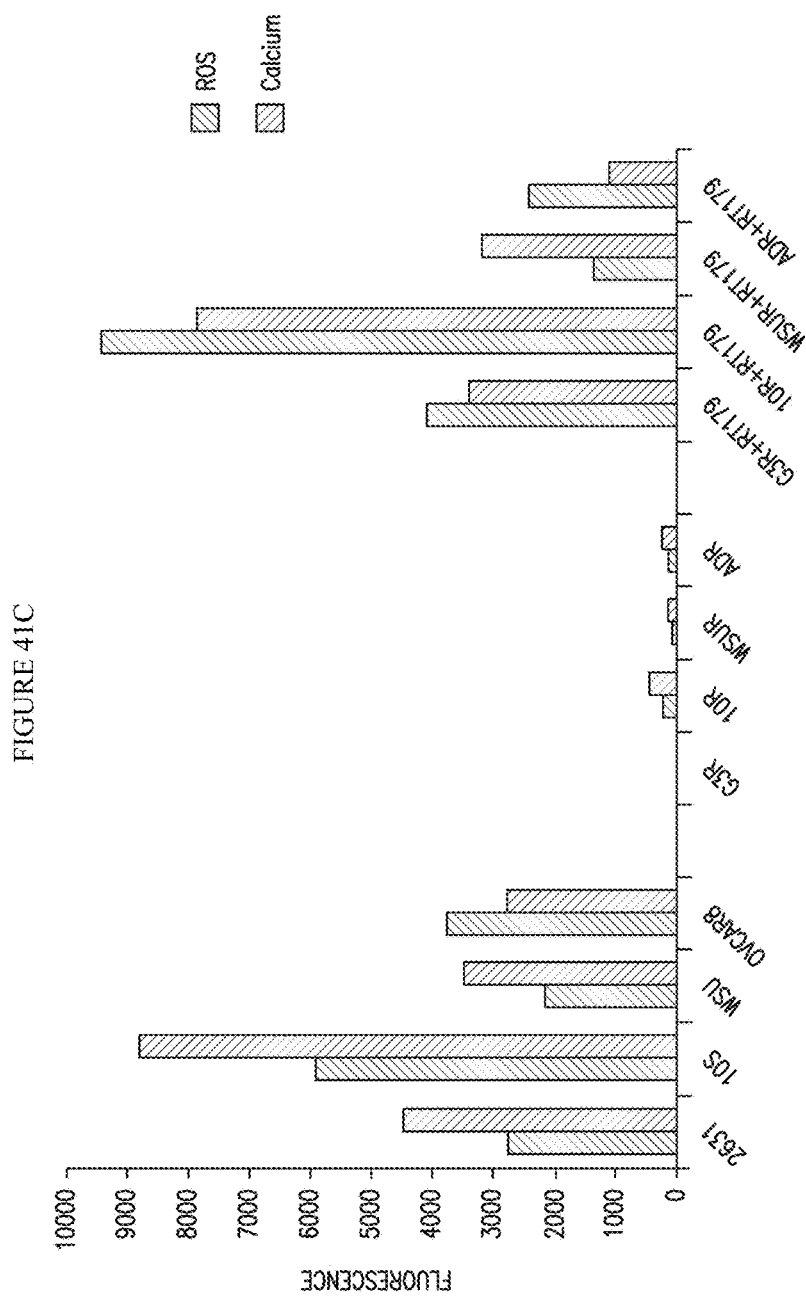
FIG. 41C shows the levels of ROS and calcium mobilization in more CHOP-sensitive lymphoma (CRL2631, 10S, WSU) compared to the more resistant derivative cell lines (G3, 10R, WSU-R), and in the more doxorubicin-sensitive OVCAR8 versus the more resistant derivative cell line ADR.

MDR/P-gp activity is closely associated with calcium status in the cell, so calcium modulators were tested for effects on ROS. As shown in FIG. 40, both a cell-permeable calcium chelator (BAPTA-AM) and a calcium channel blocker (and efflux pump inhibitor) induced ROS in G3 cells. As shown in FIGS. 41A and 39B, P-gp inhibitors (Reserpine, Elacridar) induced ROS relative to control drugs (Carboxin, Nifazoxinide). As shown in FIG. 41B, a P-gp inhibitor (Elacridar) induced calcium in a similar manner as RTI-79. indicating connections between calcium, ROS, and efflux pump activity in the mechanism of action of RTIs. Because calcium modulators induced ROS, testing was performed to investigate whether RTI-induced ROS was associated with calcium mobilization in doxorubicin-sensitive and doxorubicin-resistant cells and in resistant cells treated with RTI-79. Relatively Dox-sensitive lymphoma (CRL2631, 10S, WSU) and ovarian carcinoma (OVCAR8) and more Dox-resistant lymphoma (G3R, 10R, WSUR) and ovarian carcinoma (ADR) were treated with 10 uM DMSO for 2 hrs. Dox-resistant cells were also treated with 10 uM RTI-79 for 2 hrs (G3R+RTI-79; 10R+RTI-79, WSUR+RTI-79). Cells were co-stained with the cell-permeable red fluorescent ROS indicator, CellROX, and cell-permeable green fluorescent calcium indicator, Fluo-4AM, and then subjected to flow cytometry to quantitate changes in ROS and calcium levels. As shown in FIG. 41C, levels of both ROS and calcium in doxorubicin-sensitive cells were much higher than in the resistant lines, and RTI-79 induced both ROS and calcium mobilization in resistant cells. Thus, the ability of RTI-79 to sensitize doxorubicin-resistant cells was closely correlated with the inhibition of efflux pumps, induction of ROS, and mobilization of calcium.

Figure 42:
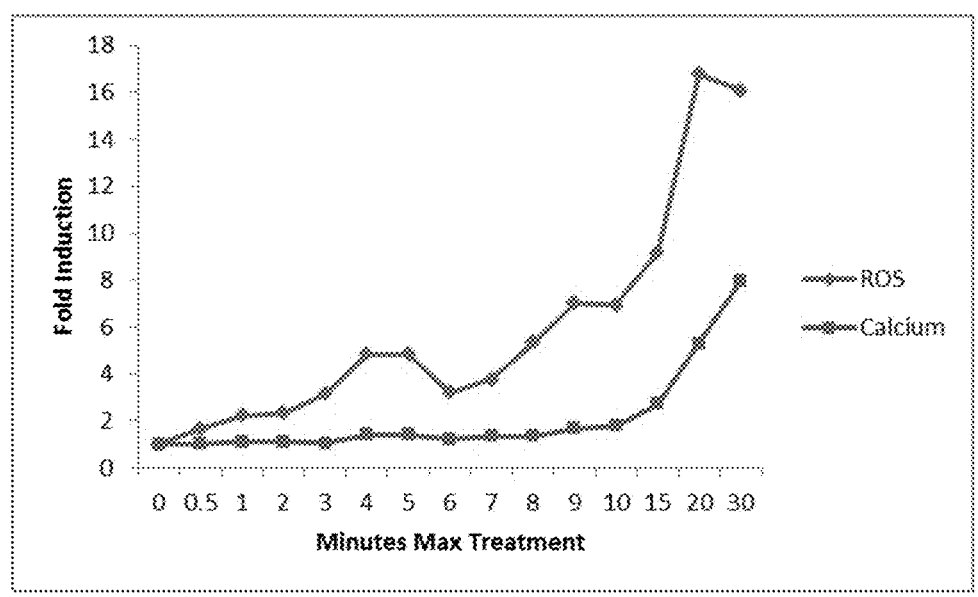
FIG. 42 shows a time course of RTI-79 induction of ROS and calcium mobilization in G3 cells.

To determine whether increases in ROS led to calcium mobilization or calcium mobilization resulted in ROS induction, a time course of RTI-79 treatment of G3 cells monitoring ROS and calcium was conducted. Cells were co-stained with the red fluorescent ROS indicator, CellROX, and the green fluorescent calcium indicator, Fluo-4AM for 30 minutes and treated with 10 uM RTI-79 for 0 to 30 minutes. All samples were analyzed at the same time in flow cytometry. As shown in FIG. 42, increases in ROS were seen as soon as 1 minute after exposure of cells to RTI-79 and gradually increase to 4 minute, level off to 5 minute, and then decrease after 6 minute, followed by increases up to 15 minute. In contrast, calcium mobilization did not occur until after 15 minutes of RTI-79 treatment, thus indicating that ROS levels increased first followed by calcium mobilization.

Figure 43:
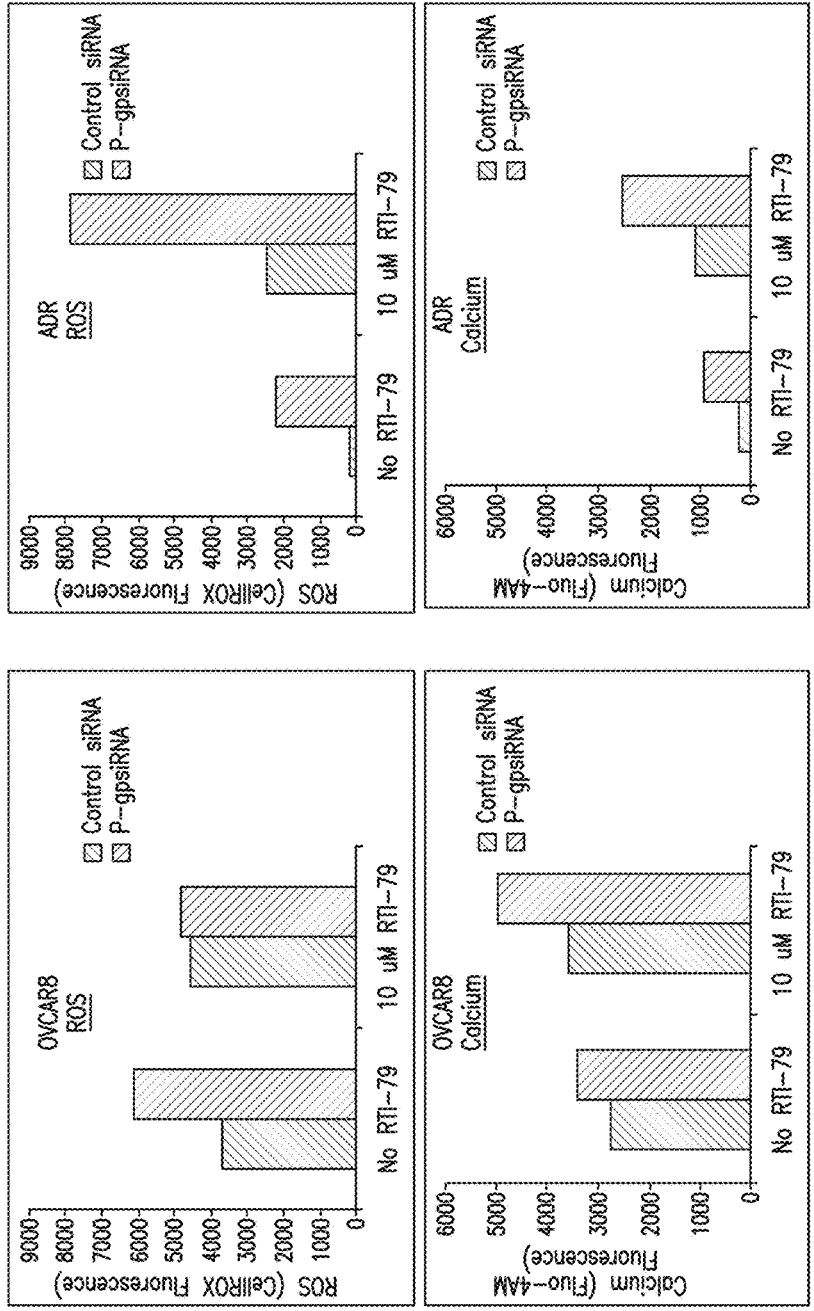
FIG. 43 shows the effects of siRNA knockdown of P-gp on induction of ROS and mobilization of calcium.

RTI-79 might inhibit MDR/P-gp by inducing ROS, which then increase calcium mobilization that then inhibits efflux pump activity. Alternatively, RTI-79 may first directly inhibit efflux pump activity, which then causes a burst of ROS followed by calcium mobilization. To determine which mechanism most likely involved, ADR-RES (Dox-resistant) and OVCAR8 (Dox-sensitive) ovarian carcinoma cells were transfected with siRNA to knockdown efflux pumps to determine the effect on ROS and calcium. Cells were then co-stained with CellROX and Fluo-4AM for 1 hour. Some cells were treated with RTI-79 for 1 hour and controls (no RTI-79) were treated with DMSO. As shown in FIG. 43, knockdown of P-gp in ADR-RES cells led to increases in both ROS and calcium mobilization, and greatly enhanced the ability of RTI-79 to increase ROS and calcium mobilization. As expected, the effect of downregulating efflux pump activity on ROS and calcium in OVCAR8 was much less than in ADR-RES, due to the lower efflux pump activity in OVCAR8 cells. However, the degree of induction of ROS and calcium mobilization by RTI-79 in P-gp knockdown cells (greater than 90% repression of P-gp expression) is much greater than what would be expected if the P-gp was the sole mechanism involved in RTI-79-induced upregulation of ROS. Thus, is it likely that RTI-79 acts not only to induce ROS and calcium mobilization through inhibition of ROS, but also acts at a second target, namely Complex I, to induce ROS.

Example 11—Preventing or Reducing Metastasis

The effects of rifabutin on cell invasion was assessed in a collagen invasion 3D assay. Increased interest in the use of 3D culture systems has been motivated by accumulating evidence that 3D models better reflect the microenvironment of tumors and metastases and more accurately predict therapeutic response in vivo compared with conventional 2D assays. A collagen invasion 3D assay allows the rapid and quantitative assessment of invasiveness and a means to screen for drugs which alter the invasive phenotype of tumor cells. Malignant cell lines with high metastatic potential in vivo show a higher rate of invasion than non-metastatic tumor cells and normal cells showed little or no ability to penetrate the barrier.

The CHOP-resistant G3 cell line is much more invasive in a collage invasion 3D assay than its CHOP-sensitive parent cell line (CRL2631). Collagen matrices (1 mg/ml) were prepared as previously described in Su, S. C., et al., Molecular profile of endothelial invasion of three-dimensional collagen matrices: insights into angiogenic sprout induction in wound healing. *Am. J. Physiol. Cell Physiol.,* 295(5): C1215-29 (2008), incorporated in material part by reference herein, with the inclusion of either DMSO control or 10 uM Rifabutin (Rif). Cells were allowed to invade for 24 hours. Culture medium was removed and collagen gels containing invading cells were fixed in 3% glutaraldehyde in PBS for 30 minutes. Gels were stained with 0.1% toluidine blue in 30% methanol for 10 minutes prior to destaining with water. Cell invasion density was quantified by counting fixed cultures under transmitted light using an Olympus CK2 inverted microscope equipped with eyepieces displaying a 10×10 ocular grid. For each condition, four random fields were selected and the number of invading cells per high power field (HPF) was counted manually at 10× magnification, corresponding to 1 mm$^2$ area.

Figure 44:
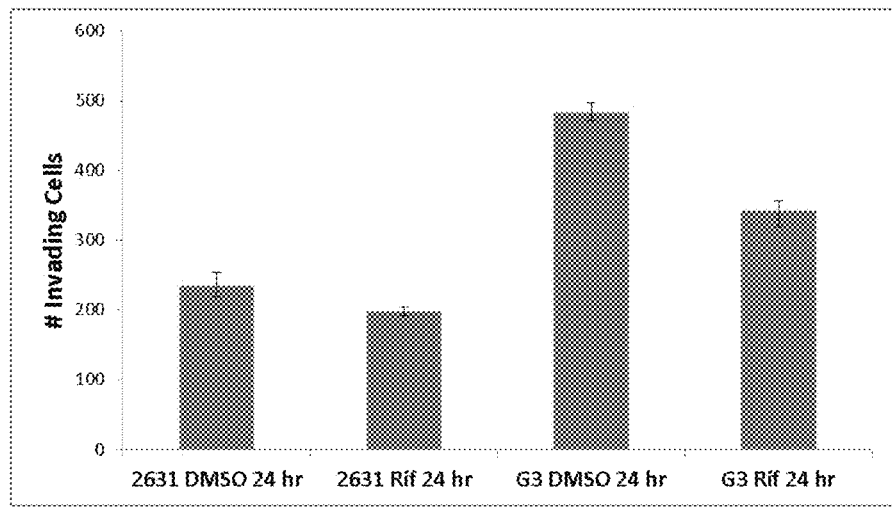
FIG. 44 shows the effects of rifabutin on G3 and CRL2631 cells in a collagen invasion 3D assay.

Data are reported as mean number of invading cells per HPF (±S.D.) in FIG. 44. G3 cells were more invasive than CRL2631 cells. The inclusion of rifabutin in the collagen matrix reduced the amount of G3 invasion by up to 30%. Less of this effect was observed for CRL2631 cells.

Figure 45:
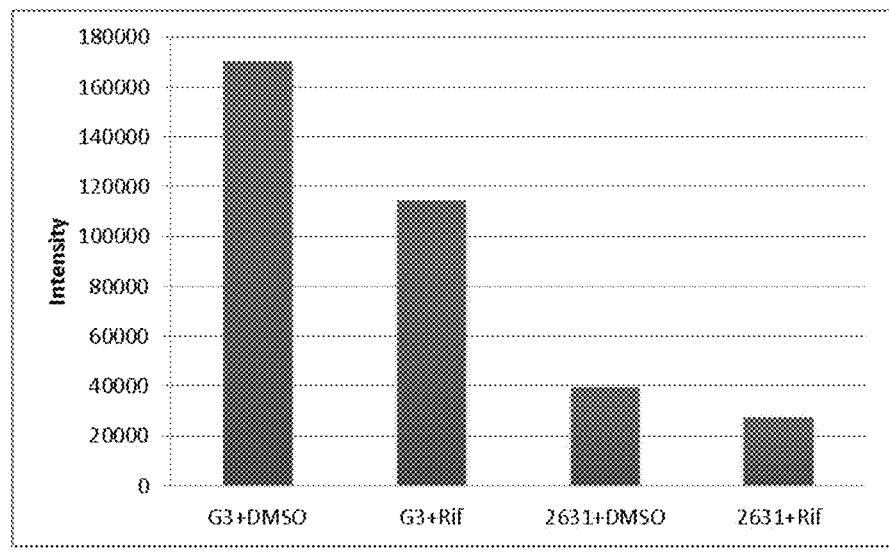
FIG. 45 shows the effects of rifabutin on G3 and CRL2631 cells in a modified Boyden chamber assay.

A modified Boyden chamber assay was used as an independent method to evaluate rifabutin's ability to suppress invasion/metastasis. G3 and CRL2631 cells were grown in the presence of 10 μM rifabutin or dose volume equivalent DMSO for 24 hours at 37° C. Cell invasion was assessed with a Chemicon QCM Collagen Invasion Assay (Millipore). The assay is a 96-well plate assay wherein each well is equipped with a suspended insert. Inserts contain an 8-micron membrane coated with a thin layer of polymerized collagen. Invading cells migrate through the collagen layer and attach to the bottom of the membrane. Cells were detached from the membrane and lysed prior to detection via CyQuant dye. Fluorescence intensity is proportional to number of invading cells. As shown in FIG. 45, the presence of rifabutin resulted in decreased relative fluorescence from 170,374 to 114,395 RLU in G3 cells. In CRL2631 cells RLU decreases from 39,356 to 27,432 RLU in the presence of rifabutin (p<0.05).

The effect of RTI-79 treatment on the secretion of MMP2 and VEGF was also analyzed. Treatment with RTI-79 resulted in statistically significant decreases in both MMP2 and VEGF in U2-OS osteosarcoma cells in commercially available ELISA based assays. In U2-OS cells, MMP2 was reduced from 22.4 ng/million cells to 10.5 ng/million cells (p<0.01) with the addition of 5 uM RTI-79. When evaluating the effects of RTI-79 on VEGF, a decrease from 998 to 436 pg/million cells (p<0.01) was observed.

Example 12—Rifabutin Derivative Synthesis

The 3,4-cyclo-rifamycin (rifabutin) derivatives of the current disclosure made be prepared as shown in the schemes listed below.

Scheme 1 illustrates the general preparation of 11-deoxo-11-imino-3,4-spiro-piperidyl-rifamycins (1c) and 11-deoxo-11-amino-3,4-spiro-piperidyl-rifamycins (1d). The compounds of (1c) are synthesized by condensation of 3-amino-4-deoxy-4-imino-rifamycin S (1a) with a substituted piperidone or hexanon-type of ketone (1b) at a temperature range from 10° C. to 70° C. in organic solvent, such as THF or ethanol, in the presence of an excess of ammonium salt, such as ammonium acetate, in a sealed reaction tube. Reduction of 11-imino-rifamycin (1c) with reducing reagent, such as NaBH$_4$, in organic solvent, such as THF and EtOH at a temperature range from 0° C. to room temperature produces 11-amino-rifamycin (1d). When the compound is RTI-35, the thioether could be oxidized to sulfoxide (—SO—) or sulfone (—SO2-) depending upon the ratio of compound 1c and oxidizing agents. When the compound is RTI-44, product is obtained by de-protection of Boc-protected-piperidine or Fmoc-protected-piperidine.

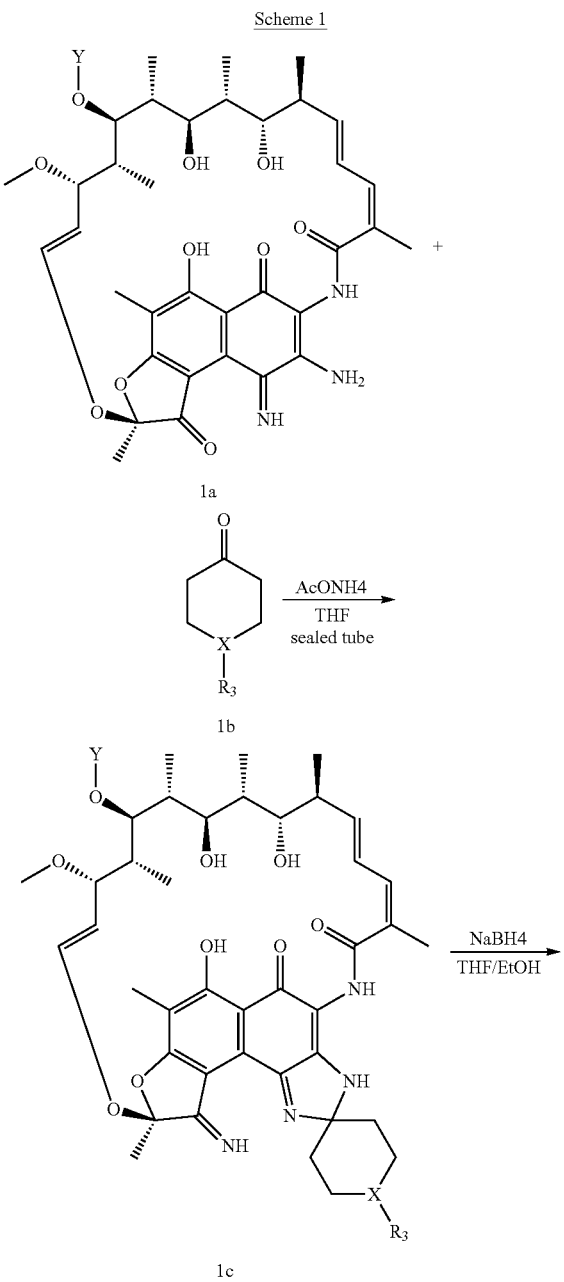

Scheme 1

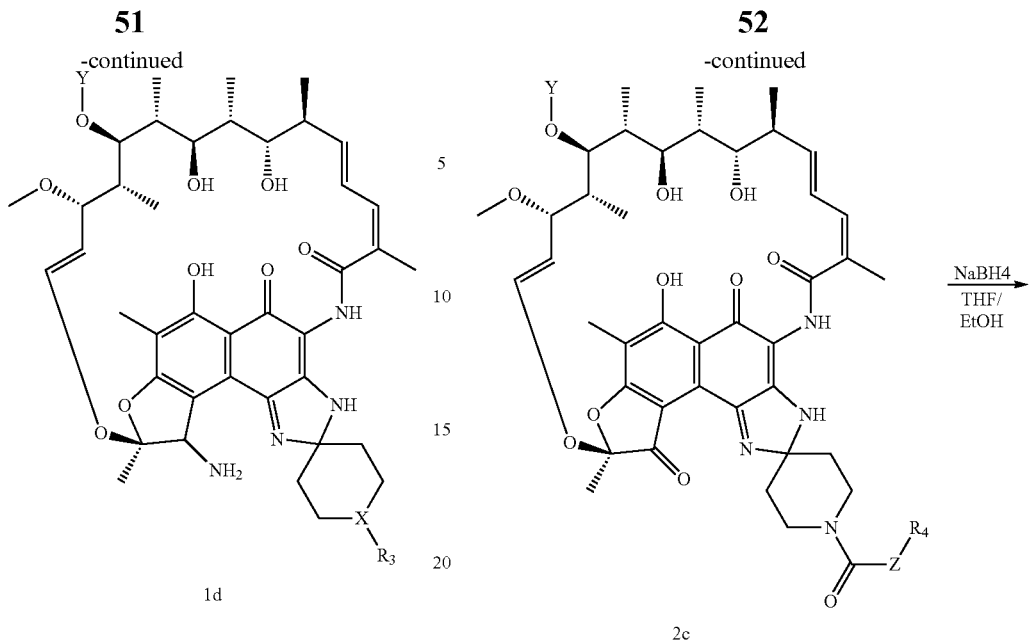

Scheme 2 illustrates the general preparation of 3,4-spiro-piperidyl-rifamycins (2c) and 11-deoxo-11-hydroxy-3,4-spiro-piperidyl-rifamycins (2d). The compounds of (2c) are synthesized by condensation of 3-amino-4-deoxy-4-imino-rifamycin S (1a) with a substituted piperidone or hexanon-type of ketone (1b) at a temperature range from 10° C. to 70° C. in organic solvent, such as THF or ethanol, in the presence or absence of a catalyst, such as Zinc. Reduction of 11-oxo of rifamycin (2c) with reducing reagent, such as NaBH$_4$, in organic solvent, such as THF and EtOH at a temperature range from 0° C. to room temperature produce 11-hydroxy-rifamycin (2d).

Scheme 2

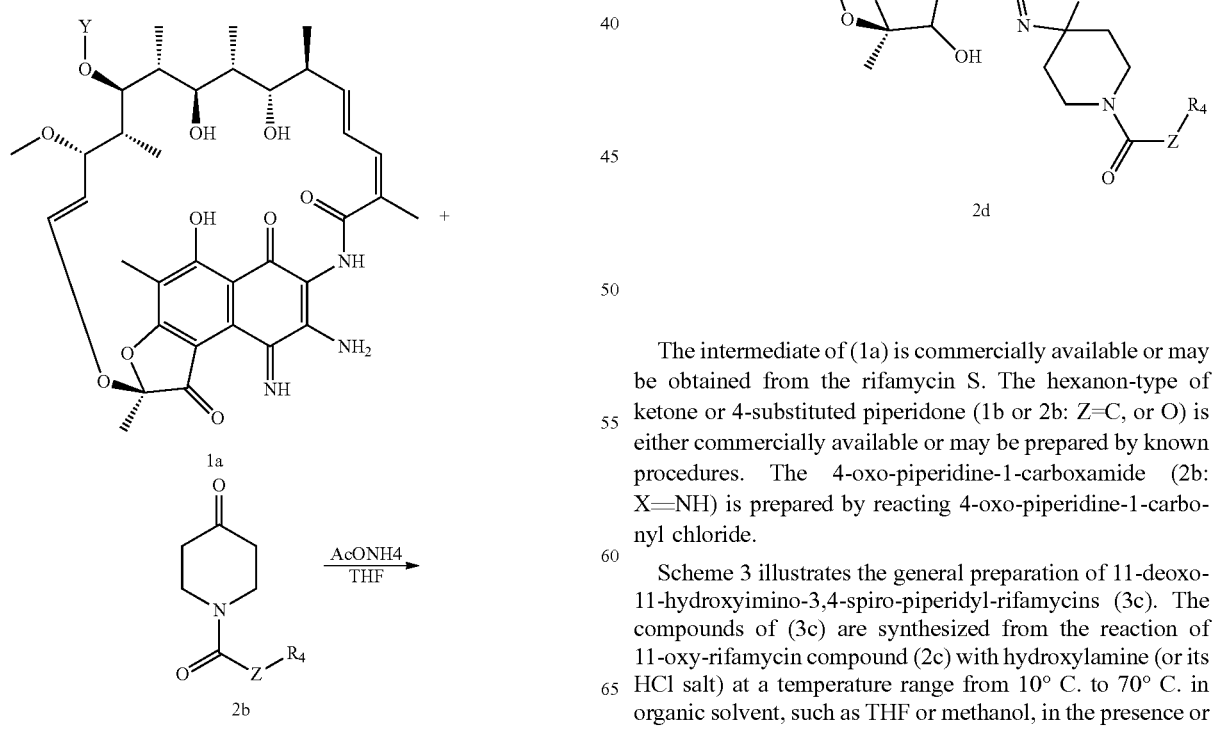

The intermediate of (1a) is commercially available or may be obtained from the rifamycin S. The hexanon-type of ketone or 4-substituted piperidone (1b or 2b: Z=C, or O) is either commercially available or may be prepared by known procedures. The 4-oxo-piperidine-1-carboxamide (2b: X=NH) is prepared by reacting 4-oxo-piperidine-1-carbonyl chloride.

Scheme 3 illustrates the general preparation of 11-deoxo-11-hydroxyimino-3,4-spiro-piperidyl-rifamycins (3c). The compounds of (3c) are synthesized from the reaction of 11-oxy-rifamycin compound (2c) with hydroxylamine (or its HCl salt) at a temperature range from 10° C. to 70° C. in organic solvent, such as THF or methanol, in the presence or absence of base, such as pyridine.

Scheme 3.

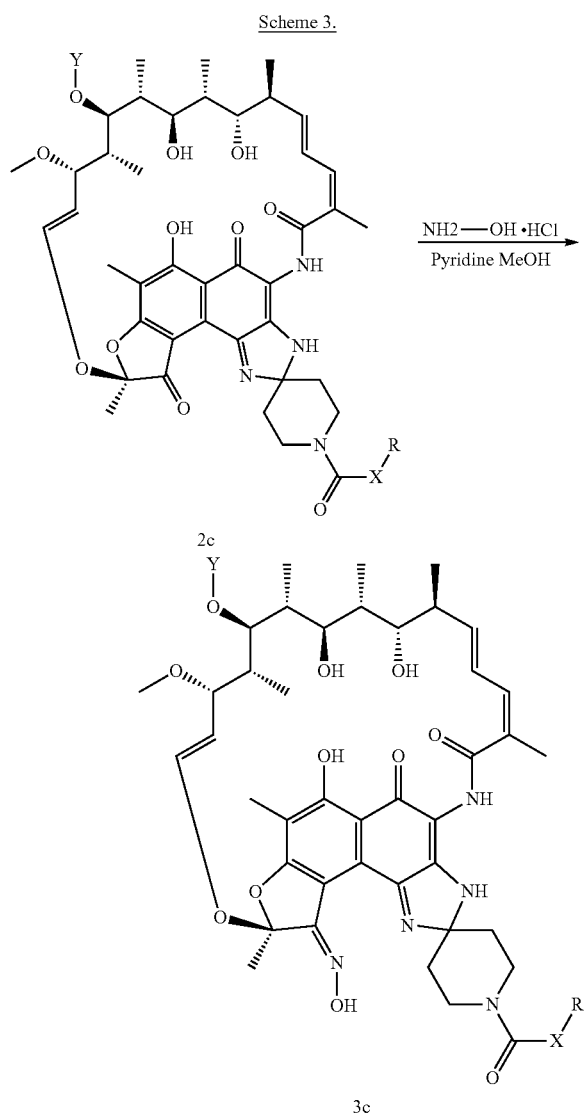

The above syntheses schemes are preferred schemes for the preparation of the indicated types of compounds It is apparent to one skilled in art that other sequences of the reactions, and alternative reagents can be used for the synthesis of the rifamycin derivatives of the present disclosure. These alternatives for the synthesis of the derivatives are within the scope of this invention.

The following examples provide synthesis schemes for specific rifabutin derivative compositions. All starting material used in these examples are either purchased from commercial sources or prepared according to published procedures. Reagents were purchased from commercial sources and used without further purification. Reactions with moisture-sensitive reagents were performed under a nitrogen atmosphere. Concentration of solutions was performed by reduced pressure (in vacuum) rotary evaporation. Column flash chromatography was performed using silica gel 60 as stationary phase. The preparative thin-layer chromatography (TLC) was performed using glass plates (20×20 cm) of silica gel (60 F254, thickness 1 mm or 2 mm).

Proton nuclear magnetic resonance (1H-NMR) spectra were recorded on a Varian Inova 300, or 500 MHz magnetic resonance spectrometer. 1H-NMR refers to proton nuclear magnetic resonance spectroscopy with chemical shifts reported in ppm (parts per million) downfield from tetramethylsilane or referred to a residue signal of solvent ($CHCl_3$=7.27). 13C-NMR spectra were recorded on Varian Inova 500 MHz spectrometer operating at 125 MHz and Chemical shifts were reported in ppm and referenced to residual solvent signals ($CHCl_3$=d 77.23 for carbon)

The high resolution mass spectra (HRMS) were carried out in a Bruker-micrOTOF-QII spectrometer, using electro spray ionization positive (ESI+) method and reported as M+H or M+Na, referring to protonated molecular ion or its sodium complex.

The following examples are for illustration purposes and are not intended to limit the scope of the invention. It will be apparent to one skilled in the art that the compounds of current invention can be prepared by a variety of synthetic routes, including but not limited to substitution of appropriate reagents, solvents or catalyst, change of reaction sequence, and variation of protecting groups.

General Procedure (A) for Synthesis of Compounds (1c in Scheme 1):

In a sealed reaction tube, a reaction mixture of 3-amino-4-imino-rifamycin S (1a) (0.1 mmol), piperidone or hexanon-type of ketone (1b) (0.2-0.3 mmol), and ammonium acetate (1 mmol) in THF (3 ml) was stirred at 60° C. overnight under nitrogen. The reaction mixture was allowed to cool to room temperature and diluted with DCM (20 ml) and water (20 ml). The aqueous phase was extracted with DCM (2×20 ml). The combined organic phase was washed with water (20 ml) and brine. The organic phase was dried over anhydrous sodium sulphate, filtered and concentrated under vacuum. The residue was purified either by silica gel column chromatography or by silica gel preparative thin-layer chromatography with methanol in DCM as eluent to give the product as purple solid.

General Procedure (B) for Synthesis of Compounds (2c in Scheme 1):

In a round bottom flask with condenser, a reaction mixture of 3-amino-4-imino-rifamycin S (1a) (0.1 mmol), piperidone or hexanon-type of ketone (1b) (0.2-0.3 mmol), and ammonium acetate (0.2-0.3 mmol) in THF (8 ml) was stirred at 75° C. overnight under nitrogen. The reaction mixture was allowed to cool to room temperature and diluted with DCM (20 ml) and water (20 ml). The aqueous phase was extracted with DCM (2×20 ml). The combined organic phase was washed with water (20 ml) and brine. The organic phase was dried over anhydrous sodium sulphate, filtered and concentrated under vacuum. The residue was purified either by silica gel column chromatography or by silica gel preparative thin-layer chromatography with methanol in DCM as eluent to give the product as purple solid.

General Procedure (C) for Synthesis of Compounds (1d in Scheme 1 and 2d in Scheme 2):

To a solution of rifamycin 11-imine or 11-oxo-compound (1c or 2c) (0.1 mmol) in THF (4 ml) was added a suspension of NaBH4 (0.2 mmol) in ethanol (4 ml) at room temperature. The reaction mixture stirred at room temperature for 1.5 hours and diluted with ethyl acetate (20 ml) and water (20 ml). The aqueous phase was extracted with ethyl acetate (2×20 ml). The combined organic phase was washed with water and brine. The organic phase was dried over anhydrous sodium sulphate, filtered and concentrated under vacuum. The residue was purified either by silica gel column chromatography or by silica gel preparative thin-layer chromatography with methanol in DCM as eluent to give the product as purple solid.

Preparation of RTI-33 11-deoxy-11-imino-4-deoxy-3,4[2-spiro-[1-(t-butyloxycarbonyl)-piperidin-4-yl]]-(1H)-imidazo-(2,5-dihydro)rifamycin S Following the general procedure (A), the title compound was obtained as a pure solid. HRMS (ESI+): 890.4570 (M+H)+; calculated for (M+H)+: 890.4553; 1H-NMR (300 MHz, CDCl$_3$) δ −0.09 (d, J=7 Hz, 3H), 0.61 (d, J=7 Hz, 3H), 0.84 (d, J=7 Hz, 3H), 1.04 (d, J=7 Hz, 3H), 1.44 (m, 1H), 1.50 (s, 9H), 1.6-1.85 (m, 4H), 1.88 (s, 3H), 1.9-2.15 (m, 2H), 2.02 (s, 3H), 2.05 (s, 3H), 2.35 (s, 3H), 2.40 (m, 1H), 3.00 (m, 1H), 3.09 (s, 3H), 3.33 (m, 1H), 3.49 (s, 1H), 3.60 (d, J=5 Hz, 1H), 3.68 (d, J=10 Hz, 1H), 3.6-3.8 (br, 2H), 3.95-4.1 (br, 2H), 4.72 (d, J=10 Hz, 1H), 5.07 (dd, J=12 and 7 Hz, 1H), 6.03 (dd, J=16 and 7 Hz, 1H), 6.16 (d, J=12 Hz, 1H), 6.28 (d, J=10 Hz, 1H), 6.40 (dd, J=16 and 10 Hz, 1H), 8.26 (s, 1H), 8.71 (bs, 1H), 12.93 (s, 1H), 14.21 (s, 1H).

Preparation of RTI-35 11-deoxy-11-imino-4-deoxy-3,4[2-spiro-tetrahydrothiopyran-4-yl]-(1H)-imidazo-(2,5-dihydro)rifamycin S Following the general procedure (A), the title compound was obtained as a pure solid. HRMS (ESI+): 807.3665 (M+H)+; calculated for (M+H)+: 807.3640; RTI-035A, 1H-NMR (300 MHz, CDCl3): −0.08 (d, J=7 Hz, 3H), 0.62 (d, J=7 Hz, 3H), 0.85 (d, J=7 Hz, 3H), 1.05 (d, J=7 Hz, 3H), 1.44 (m, 1H), 1.75-1.85 (m, 2H), 1.89 (s, 3H), 2.02 (s, 3H), 2.07 (s, 3H), 1.9-2.15 (m, 4H), 2.35 (s, 3H), 2.40 (m, 1H), 2.75-2.9 (m, 2H), 3.00 (m, 1H), 3.09 (s, 3H), 3.15-3.3 (m, 2H), 3.34 (dd, J=7 and 2 Hz, 1H), 3.47 (s, 1H), 3.60 (d, J=6 Hz, 1H), 3.68 (d, J=10 Hz, 1H), 4.72 (d, J=10 Hz, 1H), 5.07 (dd, J=12 and 8 Hz, 1H), 6.03 (dd, J=15 and 6 Hz, 1H), 6.18 (d, J=12 Hz, 1H), 6.30 (d, J=10 Hz, 1H), 6.40 (dd, J=15 and 10 Hz, 1H), 8.23 (s, 1H), 8.78 (s, 1H), 12.93 (s, 1H), 14.21 (s, 1H).

Preparation of RTI-44 11-deoxy-11-imino-4-deoxy-3,4[2-spiro-[piperidin-4-yl]]-(1H)-imidazo-(2,5-dihydro)rifamycin S Following the general procedure (A), the title compound was obtained as a pure solid. HRMS (ESI+): 790.4078 (M+H)+; calculated for (M+H)+: 790.4029; RTI-044C, 1H-NMR (300 MHz, CDCl3): −0.08 (d, J=7 Hz, 3H), 0.61 (d, J=7 Hz, 3H), 0.85 (d, J=7 Hz, 3H), 1.05 (d, J=7 Hz, 3H), 1.44 (m, 1H), 1.75-1.85 (m, 2H), 1.89 (s, 3H), 2.02 (s, 3H), 2.07 (s, 3H), 1.85-2.15 (m, 4H), 2.35 (s, 3H), 2.40 (m, 1H), 3.00 (m, 1H), 3.09 (s, 3H), 3.15-3.3 (m, 2H), 3.3-3.45 (m, 4H), 3.50 (s, 1H), 3.45-3.65 (br, 1H), 3.69 (d, J=10 Hz, 1H), 4.75 (d, J=10 Hz, 1H), 5.08 (dd, J=12 and 7 Hz, 1H), 6.04 (dd, J=15 and 6 Hz, 1H), 6.18 (d, J=12 Hz, 1H), 6.30 (d, J=10 Hz, 1H), 6.42 (dd, J=15 and 10 Hz, 1H), 8.24 (s, 1H), 8.82 (s, 1H), 13.00 (s, 1H), 14.28 (s, 1H).

Preparation of RTI-46 11-deoxy-11-imino-4-deoxy-3,4[2-spiro-cyclohexyl]-(1H)-imidazo-(2,5-dihydro)rifamycin S Following the general procedure (A), the title compound was obtained as a pure solid. HRMS (ESI+): 789.4122 (M+H)+; calculated for (M+H)+: 789.4076; RTI-046C, 1H-NMR (300 MHz, CDCl3): −0.09 (d, J=7 Hz, 3H), 0.61 (d, J=7 Hz, 3H), 0.85 (d, J=7 Hz, 3H), 1.04 (d, J=7 Hz, 3H), 1.44 (m, 1H), 1.7-1.9 (m, 10H), 1.89 (s, 3H), 2.01 (s, 3H), 2.06 (s, 3H), 1.95-2.1 (m, 2H), 2.33 (s, 3H), 2.40 (m, 1H), 3.00 (m, 1H), 3.08 (s, 3H), 3.34 (dd, J=7 and 3 Hz, 1H), 3.45 (s, 1H), 3.62 (d, J=6 Hz, 1H), 3.68 (d, J=10 Hz, 1H), 4.75 (d, J=10 Hz, 1H), 5.08 (dd, J=12 and 7 Hz, 1H), 6.03 (dd, J=15 and 6 Hz, 1H), 6.16 (d, J=12 Hz, 1H), 6.27 (d, J=10 Hz, 1H), 6.40 (dd, J=15 and 10 Hz, 1H), 8.21 (s, 1H), 8.87 (s, 1H), 13.00 (s, 1H), 14.33 (s, 1H).

Preparation of RTI-49 11-deoxy-11-imino-4-deoxy-3,4[2-spiro-[1-(benzyl)-piperidin-4-yl]]-(1H)-imidazo-(2,5-dihydro)rifamycin S Following the general procedure (A), the title compound was obtained as a pure solid. HRMS (ESI+): 880.4535 (M+H)+; calculated for (M+H)+: 880.4498; RTI-049A, 1H-NMR (300 MHz, CDCl3): −0.09 (d, J=7 Hz, 3H), 0.60 (d, J=7 Hz, 3H), 0.84 (d, J=7 Hz, 3H), 1.04 (d, J=7 Hz, 3H), 1.44 (m, 1H), 1.65-1.85 (m, 2H), 1.91 (s, 3H), 2.01 (s, 3H), 2.07 (s, 3H), 2.35 (s, 3H), 2.40 (m, 1H), 2.47 (t, J=6 Hz, 2H), 2.76 (t, J=6 Hz, 2H), 2.8-2.95 (m, 4H), 3.00 (m, 1H), 3.09 (s, 3H), 3.33 (dd, J=7 and 2 Hz, 1H), 3.46 (s, 1H), 3.60-3.72 (m, 4H), 4.74 (d, J=10 Hz, 1H), 5.08 (dd, J=12 and 7 Hz, 1H), 6.04 (dd, J=16 and 7 Hz, 1H), 6.18 (d, J=12 Hz, 1H), 6.27 (d, J=10 Hz, 1H), 6.40 (dd, J=16 and 10 Hz, 1H), 7.3-7.45 (m, 5H), 8.22 (s, 1H), 8.80 (s, 1H), 12.99 (s, 1H), 14.31 (s, 1H).

Preparation of RTI-51 11-deoxy-11-imino-4-deoxy-3,4[2-spiro-[1-(2-methoxyethyl)-piperidin-4-yl]]-(1H)-imidazo-(2,5-dihydro)rifamycin S Following the general procedure (A), the title compound was obtained as a pure solid. HRMS (ESI+): 848.4487 (M+H)+; calculated for (M+H)+: 848.4447; RTI-051A, 1H-NMR (300 MHz, CDCl3): −0.09 (d, J=7 Hz, 3H), 0.61 (d, J=7 Hz, 3H), 0.85 (d, J=7 Hz, 3H), 1.04 (d, J=7 Hz, 3H), 1.44 (m, 1H), 1.65-1.85 (m, 4H), 1.90 (s, 3H), 2.02 (s, 3H), 2.07 (s, 3H), 1.85-2.15 (br, 2H), 2.35 (s, 3H), 2.40 (m, 1H), 2.79 (t, J=5 Hz, 2H), 2.85-2.95 (m, 4H), 3.00 (m, 1H), 3.09 (s, 3H), 3.33 (dd, J=7 and 2 Hz, 1H), 3.41 (s, 3H), 3.49 (s, 1H), 3.59 (t, J=5 Hz, 2H), 3.64 (d, J=6 Hz, 1H), 3.68 (d, J=10 Hz, 1H), 4.75 (d, J=10 Hz, 1H), 5.08 (dd, J=12 and 7 Hz, 1H), 6.04 (dd, J=15 and 7 Hz, 1H), 6.16 (d, J=12 Hz, 1H), 6.27 (d, J=10 Hz, 1H), 6.41 (dd, J=15 and 10 Hz, 1H), 8.25 (s, 1H), 8.77 (s, 1H), 12.94 (s, 1H), 14.31 (s, 1H).

Preparation of RTI-53 11-deoxy-11-imino-4-deoxy-3,4[2-spiro-[1-(2-morpholinoethyl)-piperidin-4-yl]]-(1H)-imidazo-(2,5-dihydro)rifamycin S Following the general procedure (A), the title compound was obtained as a pure solid. HRMS (ESI+): 903.4904 (M+H)+; calculated for (M+H)+: 903.4869; RTI-053A, 1H-NMR (300 MHz, CDCl3): −0.09 (d, J=7 Hz, 3H), 0.61 (d, J=7 Hz, 3H), 0.85 (d, J=7 Hz, 3H), 1.04 (d, J=7 Hz, 3H), 1.44 (m, 1H), 1.65-1.85 (m, 4H), 1.90 (s, 3H), 2.02 (s, 3H), 2.07 (s, 3H), 1.85-2.15 (br, 2H), 2.34 (s, 3H), 2.40 (m, 1H), 2.5-2.65 (m, 6H), 2.74 (m, 2H), 2.85-2.95 (m, 4H), 3.00 (m, 1H), 3.09 (s, 3H), 3.33 (dd, J=7 and 2 Hz, 1H), 3.49 (s, 1H), 3.64 (d, J=6 Hz, 1H), 3.68 (d, J=10 Hz, 1H), 3.74 (t, J=5 Hz, 4H), 4.75 (d, J=10 Hz, 1H), 5.08 (dd, J=12 and 7 Hz, 1H), 6.04 (dd, J=15 and 7 Hz, 1H), 6.16 (d, J=12 Hz, 1H), 6.28 (d, J=10 Hz, 1H), 6.40 (dd, J=15 and 10 Hz, 1H), 8.25 (s, 1H), 8.77 (s, 1H), 12.94 (s, 1H), 14.29 (s, 1H).

Preparation of RTI-57 11-deoxy-11-imino-4-deoxy-3,4[2-spiro-[1-(cyclobutylmethyl)-piperidin-4-yl]]-(1H)-imidazo-(2,5-dihydro)rifamycin S Following the general procedure (A), the title compound was obtained as a pure solid. HRMS (ESI+): 858.4690

(M+H)+; calculated for (M+H)+: 858.4655; RTI-057A, 1H-NMR (300 MHz, CDCl3): −0.09 (d, J=7 Hz, 3H), 0.61 (d, J=7 Hz, 3H), 0.85 (d, J=7 Hz, 3H), 1.04 (d, J=7 Hz, 3H), 1.44 (m, 1H), 1.7-1.85 (m, 8H), 1.90 (s, 3H), 1.9-2.15 (m, 4H), 2.02 (s, 3H), 2.07 (s, 3H), 2.35 (s, 3H), 2.40 (m, 1H), 2.60 (m, 3H), 2.7-2.9 (br, 4H), 3.00 (m, 1H), 3.09 (s, 3H), 3.34 (dd, J=7 and 2 Hz, 1H), 3.46 (s, 1H), 3.63 (d, J=6 Hz, 1H), 3.68 (d, J=10 Hz, 1H), 4.75 (d, J=10 Hz, 1H), 5.08 (dd, J=12 and 7 Hz, 1H), 6.03 (dd, J=16 and 7 Hz, 1H), 6.17 (d, J=12 Hz, 1H), 6.28 (d, J=10 Hz, 1H), 6.40 (dd, J=16 and 10 Hz, 1H), 8.22 (s, 1H), 8.80 (s, 1H), 12.95 (s, 1H), 14.31 (s, 1H).

Preparation of RTI-59 11-deoxy-11-imino-4-deoxy-3,4[2-spiro-[1-(cyclopropylmethyl)-piperidin-4-yl]]-(1H)-imidazo-(2,5-dihydro)rifamycin S Following the general procedure (A), the title compound was obtained as a pure solid. HRMS (ESI+): 844.4536 (M+H)+; calculated for (M+H)+: 844.4498; RTI-059A, 1H-NMR (300 MHz, CDCl3): −0.09 (d, J=7 Hz, 3H), 0.18 (m, 2H), 0.57 (m, 2H), 0.61 (d, J=7 Hz, 3H), 0.84 (d, J=7 Hz, 3H), 0.93 (m, 1H), 1.04 (d, J=7 Hz, 3H), 1.44 (m, 1H), 1.7-1.85 (m, 4H), 1.90 (s, 3H), 1.95-2.15 (br, 2H), 2.02 (s, 3H), 2.07 (s, 3H), 2.35 (s, 3H), 2.40 (m, 1H), 2.46 (d, J=7 Hz, 2H), 2.8-3.05 (m, 5H), 3.09 (s, 3H), 3.35 (dd, J=7 and 2 Hz, 1H), 3.49 (s, 1H), 3.63 (d, J=6 Hz, 1H), 3.68 (d, J=10 Hz, 1H), 4.74 (d, J=10 Hz, 1H), 5.07 (dd, J=12 and 7 Hz, 1H), 6.03 (dd, J=16 and 7 Hz, 1H), 6.17 (d, J=12 Hz, 1H), 6.28 (d, J=10 Hz, 1H), 6.40 (dd, J=16 and 10 Hz, 1H), 8.25 (s, 1H), 8.78 (s, 1H), 12.93 (s, 1H), 14.31 (s, 1H).

Preparation of RTI-60 11-deoxy-11-imino-4-deoxy-3,4[2-spiro-[1-(isopropyl)-piperidin-4-yl]]-(1H)-imidazo-(2,5-dihydro)rifamycin S Following the general procedure (A), the title compound was obtained as a pure solid. HRMS (ESI+): 832.4542 (M+H)+; calculated for (M+H)+: 832.4498; RTI-060A, 1H-NMR (300 MHz, CDCl3): −0.09 (d, J=7 Hz, 3H), 0.60 (d, J=7 Hz, 3H), 0.84 (d, J=7 Hz, 3H), 1.04 (d, J=7 Hz, 3H), 1.16 (d, J=6 Hz, 6H), 1.44 (m, 1H), 1.7-1.8 (m, 4H), 1.88 (s, 3H), 1.95-2.15 (br, 2H), 2.01 (s, 3H), 2.05 (s, 3H), 2.33 (s, 3H), 2.40 (m, 1H), 2.75-3.05 (m, 6H), 3.08 (s, 3H), 3.34 (dd, J=7 and 2 Hz, 1H), 3.47 (s, 1H), 3.64 (d, J=6 Hz, 1H), 3.68 (d, J=10 Hz, 1H), 4.75 (d, J=10 Hz, 1H), 5.07 (dd, J=12 and 7 Hz, 1H), 6.03 (dd, J=16 and 7 Hz, 1H), 6.16 (d, J=12 Hz, 1H), 6.27 (d, J=10 Hz, 1H), 6.40 (dd, J=16 and 10 Hz, 1H), 8.22 (s, 1H), 8.76 (s, 1H), 12.91 (s, 1H), 14.31 (s, 1H).

Preparation of RTI-61 11-deoxy-11-imino-4-deoxy-3,4[2-spiro-[1-(t-ethyloxycarbonyl)-piperidin-4-yl]]-(1H)-imidazo-(2,5-dihydro)rifamycin S Following the general procedure (A), the title compound was obtained as a pure solid. HRMS (ESI+): 862.4270 (M+H)+; calculated for (M+H)+: 862.4240; RTI-61A, 1H-NMR (300 MHz, CDCl3): −0.08 (d, J=7 Hz, 3H), 0.62 (d, J=7 Hz, 3H), 0.84 (d, J=7 Hz, 3H), 1.04 (d, J=7 Hz, 3H), 1.30 (t, J=7 Hz, 3H), 1.44 (m, 1H), 1.6-1.85 (m, 4H), 1.89 (s, 3H), 2.0-2.15 (m, 2H), 2.02 (s, 3H), 2.06 (s, 3H), 2.35 (s, 3H), 2.40 (m, 1H), 3.00 (m, 1H), 3.09 (s, 3H), 3.33 (m, 1H), 3.50 (s, 1H), 3.61 (d, J=5 Hz, 1H), 3.68 (d, J=10 Hz, 1H), 3.6-3.8 (br, 2H), 4.0-4.2 (br, 2H), 4.21 (q, J=7 Hz, 2H), 4.72 (d, J=10 Hz, 1H), 5.07 (dd, J=12 and 7 Hz, 1H), 6.03 (dd, J=16 and 7 Hz, 1H), 6.17 (d, J=12 Hz, 1H), 6.29 (d, J=10 Hz, 1H), 6.41 (dd, J=16 and 10 Hz, 1H), 8.26 (s, 1H), 8.72 (bs, 1H), 12.93 (s, 1H), 14.21 (s, 1H).

Preparation of RTI-63 11-deoxy-11-imino-4-deoxy-3,4[2-spiro-[1-(acetyl)-piperidin-4-yl]]-(1H)-imidazo-(2,5-dihydro)rifamycin S Following the general procedure (A), the title compound was obtained as a pure solid. HRMS (ESI+): 832.4181 (M+H)+; calculated for (M+H)+: 832.4134. RTI-63A, 1H-NMR (300 MHz, CDCl3): −0.06 (d, J=7 Hz, 3H), 0.62 (d, J=7 Hz, 3H), 0.85 (d, J=7 Hz, 3H), 1.04 (d, J=7 Hz, 3H), 1.45 (m, 1H), 1.6-1.85 (m, 4H), 1.89 (s, 3H), 2.03 (s, 3H), 2.06 (s, 3H), 2.0-2.2 (m, 2H), 2.20 (s, 3H), 2.35 (s, 3H), 2.40 (m, 1H), 3.00 (m, 1H), 3.10 (s, 3H), 3.33 (m, 1H), 3.47 (s, 0.4H), 3.51 (s, 0.6H), 3.55-3.70 (m, 3H), 3.90 (m, 2H), 4.48 (m, 1H), 4.73 (m, 1H), 5.07 (m, 1H), 6.03 (dd, J=16 and 6 Hz, 1H), 6.18 (d, J=12 Hz, 1H), 6.29 (d, J=10 Hz, 1H), 6.38 (m, 1H), 8.25 (s, 1H), 8.66 (s, 0.6H), 8.71 (s, 0.4H), 12.92 (s, 1H), 14.16 (s, 0.4H), 14.19 (s, 0.6H).

Preparation of RTI-64 11-deoxy-11-imino-4-deoxy-3,4[2-spiro-[1-(n-propyl)-piperidin-4-yl]]-(1H)-imidazo-(2,5-dihydro)rifamycin S Following the general procedure (A), the title compound was obtained as a pure solid. HRMS (ESI+): 832.4552 (M+H)+; calculated for (M+H)+: 832.4498; RTI-064A, 1H-NMR (300 MHz, CDCl3): −0.09 (d, J=7 Hz, 3H), 0.61 (d, J=7 Hz, 3H), 0.85 (d, J=7 Hz, 3H), 0.96 (t, J=7 Hz, 3H), 1.04 (d, J=7 Hz, 3H), 1.44 (m, 1H), 1.55-1.65 (m, 2H), 1.7-1.85 (m, 4H), 1.90 (s, 3H), 1.95-2.15 (br, 2H), 2.02 (s, 3H), 2.07 (s, 3H), 2.35 (s, 3H), 2.40 (m, 1H), 2.54 (m, 2H), 2.8-2.9 (m, 4H), 3.00 (m, 1H), 3.09 (s, 3H), 3.35 (dd, J=7 and 2 Hz, 1H), 3.46 (s, 1H), 3.62 (d, J=6 Hz, 1H), 3.67 (d, J=10 Hz, 1H), 4.75 (d, J=10 Hz, 1H), 5.07 (dd, J=12 and 7 Hz, 1H), 6.03 (dd, J=16 and 7 Hz, 1H), 6.17 (d, J=12 Hz, 1H), 6.27 (d, J=10 Hz, 1H), 6.40 (dd, J=16 and 10 Hz, 1H), 8.21 (s, 1H), 8.78 (s, 1H), 12.95 (s, 1H), 14.30 (s, 1H).

Preparation of RTI-65 11-deoxy-11-imino-4-deoxy-3,4[2-spiro-[1-(cyclopropyl)-piperidin-4-yl]]-(1H)-imidazo-(2,5-dihydro)rifamycin S Following the general procedure (A), the title compound was obtained as a pure solid. HRMS (ESI+): 830.4386 (M+H)+; calculated for (M+H)+: 830.4342; RTI-065A, 1H-NMR (300 MHz, CDCl3): −0.09 (d, J=7 Hz, 3H), 0.45-0.55 (m, 5H), 0.61 (d, J=7 Hz, 3H), 0.85 (d, J=7 Hz, 3H), 1.04 (d, J=7 Hz, 3H), 1.44 (m, 1H), 1.7-1.85 (m, 4H), 1.90 (s, 3H), 1.95-2.15 (br, 2H), 2.02 (s, 3H), 2.07 (s, 3H), 2.35 (s, 3H), 2.40 (m, 1H), 2.9-3.1 (m, 5H), 3.09 (s, 3H), 3.35 (dd, J=7 and 2 Hz, 1H), 3.46 (s, 1H), 3.63 (d, J=6 Hz, 1H), 3.67 (d, J=10 Hz, 1H), 4.75 (d, J=10 Hz, 1H), 5.08 (dd, J=12 and 7 Hz, 1H), 6.04 (dd, J=16 and 7 Hz, 1H), 6.17 (d, J=12 Hz, 1H), 6.27 (d, J=10 Hz, 1H), 6.40 (dd, J=16 and 10 Hz, 1H), 8.21 (s, 1H), 8.79 (s, 1H), 12.97 (s, 1H), 14.30 (s, 1H).

Preparation of RTI-66 11-deoxy-11-imino-4-deoxy-3,4[2-spiro-[1-(ethyl)-piperidin-4-yl]]-(1H)-imidazo-(2,5-dihydro)rifamycin S Following the general procedure (A), the title compound was obtained as a pure solid. HRMS (ESI+): 818.4388 (M+H)+; calculated for (M+H)+: 818.4342; RTI-066A, 1H-NMR (300 MHz, CDCl3): −0.08 (d, J=7 Hz, 3H), 0.61

(d, J=7 Hz, 3H), 0.85 (d, J=7 Hz, 3H), 1.04 (d, J=7 Hz, 3H), 1.18 (t, J=7 Hz, 3H), 1.44 (m, 1H), 1.7-1.85 (m, 4H), 1.90 (s, 3H), 1.95-2.15 (br, 2H), 2.02 (s, 3H), 2.07 (s, 3H), 2.35 (s, 3H), 2.40 (m, 1H), 2.64 (q, J=7 Hz, 2H), 2.8-2.95 (m, 4H), 3.00 (m, 1H), 3.09 (s, 3H), 3.35 (d, J=7 Hz, 1H), 3.46 (s, 1H), 3.63 (d, J=6 Hz, 1H), 3.67 (d, J=10 Hz, 1H), 4.75 (d, J=10 Hz, 1H), 5.08 (dd, J=12 and 7 Hz, 1H), 6.04 (dd, J=16 and 7 Hz, 1H), 6.16 (d, J=12 Hz, 1H), 6.27 (d, J=10 Hz, 1H), 6.40 (dd, J=16 and 10 Hz, 1H), 8.22 (s, 1H), 8.77 (s, 1H), 12.95 (s, 1H), 14.29 (s, 1H).

Preparation of RTI-67 11-deoxy-11-imino-4-deoxy-3,4[2-spiro-[1-(beRTIoyl)-piperidin-4-yl]]-(1H)-imidazo-(2,5-dihydro)rifamycin S Following the general procedure (A), the title compound was obtained as a pure solid. HRMS (ESI$^+$): 916.4169 (M+Na)$^+$; calculated for (M+Na)$^+$: 916.4109. RTI-67A, 1H-NMR (300 MHz, CDCl3): −0.07 (br, 3H), 0.60 (br, 3H), 0.84 (br, 3H), 1.02 (d, J=7 Hz, 3H), 1.45 (m, 1H), 1.6-1.85 (m, 4H), 1.88 (s, 3H), 2.00 (s, 3H), 2.04 (s, 3H), 1.9-2.2 (m, 2H), 2.34 (s, 3H), 2.40 (m, 1H), 3.00 (m, 1H), 3.08 (s, 3H), 3.2-3.9 (br, 7H), 4.2 (br, 1H), 4.6 (br, 1H), 5.05 (br, 1H), 6.0 (br, 1H), 6.18 (br, 1H), 6.29 (br, 1H), 6.40 (br, 1H), 7.40 (m, 2H), 7.45 (m, 3H), 8.25 (s, 1H), 8.6 (brs, 1H), 12.93 (s, 1H), 14.16 (s, 1H).

Preparation of RTI-68 11-deoxy-11-imino-4-deoxy-3,4[2-spiro-[1-(benzyloxycarbonyl)-piperidin-4-yl]]-(1H)-imidazo-(2,5-dihydro)rifamycin S Following the general procedure (A), the title compound was obtained as a pure solid. HRMS (ESI$^+$): 924.4435 (M+H)$^+$; calculated for (M+H)$^+$: 924.4396; RTI-68A, 1H-NMR (300 MHz, CDCl3): −0.09 (d, J=7 Hz, 3H), 0.60 (d, J=7 Hz, 3H), 0.84 (d, J=7 Hz, 3H), 1.04 (d, J=7 Hz, 3H), 1.44 (m, 1H), 1.6-1.85 (m, 4H), 1.88 (s, 3H), 2.0-2.15 (m, 2H), 2.02 (s, 3H), 2.05 (s, 3H), 2.35 (s, 3H), 2.40 (m, 1H), 3.00 (m, 1H), 3.09 (s, 3H), 3.33 (br, 1H), 3.49 (s, 1H), 3.60 (d, J=5 Hz, 1H), 3.68 (d, J=10 Hz, 1H), 3.6-3.8 (br, 2H), 4.0-4.2 (m, 2H), 4.72 (d, J=10 Hz, 1H), 5.07 (dd, J=12 and 7 Hz, 1H), 5.20 (s, 2H), 6.03 (dd, J=16 and 7 Hz, 1H), 6.17 (d, J=12 Hz, 1H), 6.29 (d, J=10 Hz, 1H), 6.41 (dd, J=16 and 10 Hz, 1H), 7.38 (m, 5H), 8.26 (s, 1H), 8.70 (bs, 1H), 12.92 (s, 1H), 14.20 (s, 1H).

Preparation of RTI-69 11-deoxy-11-imino-4-deoxy-3,4[2-spiro-[1-(methyl)-piperidin-4-yl]]-(1H)-imidazo-(2,5-dihydro)rifamycin S Following the general procedure (A), the title compound was obtained as a pure solid. HRMS (ESI$^+$): 804.4213 (M+H)$^+$; calculated for (M+H)$^+$: 804.4185; RTI-069A, 1H-NMR (300 MHz, CDCl3): −0.08 (d, J=7 Hz, 3H), 0.61 (d, J=7 Hz, 3H), 0.85 (d, J=7 Hz, 3H), 1.04 (d, J=7 Hz, 3H), 1.45 (m, 1H), 1.7-1.85 (m, 4H), 1.90 (s, 3H), 1.95-2.15 (br, 2H), 2.02 (s, 3H), 2.07 (s, 3H), 2.35 (s, 3H), 2.40 (m, 1H), 2.49 (s, 3H), 2.7-2.95 (m, 4H), 3.00 (m, 1H), 3.09 (s, 3H), 3.34 (d, J=7 Hz, 1H), 3.48 (s, 1H), 3.63 (d, J=6 Hz, 1H), 3.68 (d, J=10 Hz, 1H), 4.75 (d, J=10 Hz, 1H), 5.08 (dd, J=12 and 7 Hz, 1H), 6.04 (dd, J=16 and 7 Hz, 1H), 6.17 (d, J=12 Hz, 1H), 6.27 (d, J=10 Hz, 1H), 6.40 (dd, J=16 and 10 Hz, 1H), 8.23 (s, 1H), 8.77 (s, 1H), 12.95 (s, 1H), 14.29 (s, 1H).

Preparation of RTI-70 11-deoxy-11-imino-4-deoxy-3,4[2-spiro-[1-(2-methylpropyl)-piperidin-4-yl]]-(1H)-imidazo-(2,5-dihydro)rifamycin S Following the general procedure (A), the title compound was obtained as a pure solid. HRMS (ESI$^+$): 846.4682 (M+H)$^+$; calculated for (M+H)$^+$: 846.4655; RTI-070A, 1H-NMR (500 MHz, CDCl3): −0.09 (d, J=7 Hz, 3H), 0.60 (d, J=7 Hz, 3H), 0.84 (d, J=7 Hz, 3H), 0.94 (d, J=7 Hz, 6H), 1.04 (d, J=7 Hz, 3H), 1.44 (m, 1H), 1.74-1.85 (m, 3H), 1.89 (s, 3H), 1.9-2.15 (m, 4H), 2.01 (s, 3H), 2.05 (s, 3H), 2.29 (d, J=7 Hz, 2H), 2.33 (s, 3H), 2.40 (m, 1H), 2.75-2.85 (m, 4H), 3.00 (m, 1H), 3.08 (s, 3H), 3.33 (dd, J=7 and 2 Hz, 1H), 3.46 (s, 1H), 3.63 (d, J=6 Hz, 1H), 3.68 (d, J=10 Hz, 1H), 4.75 (dd, J=10 and 2 Hz, 1H), 5.07 (dd, J=12 and 7 Hz, 1H), 6.03 (dd, J=16 and 7 Hz, 1H), 6.16 (d, J=12 Hz, 1H), 6.27 (d, J=10 Hz, 1H), 6.40 (dd, J=16 and 10 Hz, 1H), 8.23 (s, 1H), 8.78 (s, 1H), 12.96 (s, 1H), 14.30 (s, 1H). 13C-NMR (125 MHz, CDCl3).

Preparation of RTI-74 11-deoxy-11-imino-4-deoxy-3,4[2-spiro-[1-(phenylaminocarbonyl)-piperidin-4-yl]]-(1H)-imidazo-(2,5-dihydro)rifamycin S Following the general procedure (A), the title compound was obtained as a pure solid. HRMS (ESI$^+$): 909.4433 (M+H)$^+$; calculated for (M+H)$^+$: 909.4400; RTI-074A, 1H-NMR (300 MHz, CDCl3): −0.07 (d, J=7 Hz, 3H), 0.62 (d, J=7 Hz, 3H), 0.84 (d, J=7 Hz, 3H), 1.04 (d, J=7 Hz, 3H), 1.44 (m, 1H), 1.6-1.85 (m, 3H), 1.89 (s, 3H), 1.9-2.25 (m, 3H), 2.02 (s, 3H), 2.05 (s, 3H), 2.35 (s, 3H), 2.40 (m, 1H), 3.00 (m, 1H), 3.09 (s, 3H), 3.33 (m, 1H), 3.51 (s, 1H), 3.61 (d, J=6 Hz, 1H), 3.68 (d, J=10 Hz, 1H), 3.6-3.8 (br, 2H), 4.0-4.2 (br, 2H), 4.72 (d, J=10 Hz, 1H), 5.07 (dd, J=12 and 7 Hz, 1H), 6.03 (dd, J=16 and 7 Hz, 1H), 6.16 (d, J=12 Hz, 1H), 6.28 (d, J=10 Hz, 1H), 6.40 (m, 2H), 7.15 (m, 1H), 7.34 (m, 4H), 8.27 (s, 1H), 8.69 (s, 1H), 12.92 (s, 1H), 14.19 (s, 1H).

Preparation of RTI-77 11-deoxy-11-imino-4-deoxy-3,4[2-spiro-[1-(ethyloxycarbonyl)-piperidin-4-yl]]-(1H)-imidazo-(2,5-dihydro)rifamycin S Following the general procedure (A), the title compound was obtained as a pure solid. HRMS (ESI$^+$): 876.4417 (M+H)$^+$; calculated for (M+H)$^+$: 876.4396; RTI-77A, 1H-NMR (300 MHz, CDCl3): −0.08 (d, J=7 Hz, 3H), 0.61 (d, J=7 Hz, 3H), 0.84 (d, J=7 Hz, 3H), 1.04 (d, J=7 Hz, 3H), 0.99 (t, J=7 Hz, 3H), 1.44 (m, 1H), 1.6-1.85 (m, 6H), 1.88 (s, 3H), 2.0-2.15 (m, 2H), 2.02 (s, 3H), 2.05 (s, 3H), 2.35 (s, 3H), 2.40 (m, 1H), 3.00 (m, 1H), 3.09 (s, 3H), 3.33 (m, 1H), 3.49 (s, 1H), 3.60 (d, J=5 Hz, 1H), 3.68 (d, J=10 Hz, 1H), 3.6-3.8 (br, 2H), 4.0-4.2 (m, 4H), 4.72 (d, J=10 Hz, 1H), 5.07 (dd, J=12 and 7 Hz, 1H), 6.03 (dd, J=16 and 7 Hz, 1H), 6.17 (d, J=12 Hz, 1H), 6.28 (d, J=10 Hz, 1H), 6.41 (dd, J=16 and 10 Hz, 1H), 8.25 (s, 1H), 8.7 (bs, 1H), 12.93 (s, 1H), 14.20 (s, 1H).

Preparation of RTI-81 11-deoxy-11-imino-4-deoxy-3,4[2-spiro-[1-(isobutyloxycarbonyl)-piperidin-4-yl]]-(1H)-imidazo-(2,5-dihydro)rifamycin S Following the general procedure (A), the title compound was obtained as a pure solid. HRMS (ESI$^+$): 890.4552 (M+H)$^+$; calculated for (M+H)$^+$: 890.4553; RTI-081, 1H-NMR (300 MHz, CDCl3): −0.09 (d, J=7 Hz, 3H), 0.61 (d, J=7 Hz, 3H), 0.84 (d, J=7 Hz, 3H), 0.98 (d, J=7 Hz, 6H), 1.04 (d, J=7 Hz, 3H), 1.44 (m, 1H), 1.6-1.85 (m, 4H), 1.88 (s, 3H), 1.9-2.15 (m, 3H), 2.01 (s, 3H), 2.05 (s, 3H), 2.35 (s, 3H), 2.40 (m, 1H), 3.00 (m, 1H), 3.09 (s, 3H), 3.33 (m, 1H), 3.49 (s, 1H), 3.60 (d, J=6 Hz, 1H), 3.68 (d, J=10 Hz, 1H), 3.6-3.8 (br, 2H), 3.95 (m, 2H), 4.0-4.2 (br, 2H), 4.72 (d, J=10 Hz, 1H), 5.07 (dd, J=12 and 7 Hz, 1H), 6.03 (dd, J=16 and 7 Hz, 1H), 6.16 (d, J=12 Hz, 1H), 6.27 (d, J=10 Hz, 1H), 6.40 (dd, J=16 and 10 Hz, 1H), 8.25 (s, 1H), 8.7 (bs, 1H), 12.93 (s, 1H), 14.20 (s, 1H).

Preparation of RTI-82 11-deoxy-11-imino-4-deoxy-3,4[2-spiro-[1-(ethylaminocarbonyl)-piperidin-4-yl]]-(1H)-imidazo-(2,5-dihydro)rifamycin S Following the general procedure (A), the title compound was obtained as a pure solid. HRMS (ESI$^+$): 883.4175 (M+Na)$^+$; calculated for (M+Na)$^+$: 883.4218; RTI-082A, 1H-NMR (300 MHz, CDCl3): −0.08 (d, J=7 Hz, 3H), 0.61 (d, J=7 Hz, 3H), 0.84 (d, J=7 Hz, 3H), 1.04 (d, J=7 Hz, 3H), 1.20 (t, J=7 Hz, 3H), 1.44 (m, 1H), 1.6-1.85 (m, 3H), 1.88 (s, 3H), 1.9-2.25 (m, 3H), 2.02 (s, 3H), 2.05 (s, 3H), 2.35 (s, 3H), 2.40 (m, 1H), 3.00 (m, 1H), 3.09 (s, 3H), 3.3-3.4 (m, 3H), 3.50 (s, 1H), 3.61 (d, J=6 Hz, 1H), 3.68 (d, J=10 Hz, 1H), 3.6-3.7 (br, 2H), 3.8-4.0 (br, 2H), 4.52 (m, 1H), 4.72 (d, J=10 Hz, 1H), 5.07 (dd, J=12 and 7 Hz, 1H), 6.03 (dd, J=16 and 7 Hz, 1H), 6.16 (d, J=12 Hz, 1H), 6.28 (d, J=10 Hz, 1H), 6.40 (m, 1H), 8.25 (s, 1H), 8.69 (s, 1H), 12.92 (s, 1H), 14.20 (s, 1H).

Preparation of RTI-83 4-deoxy-3,4[2-spiro-[1-(ethylaminocarbonyl)-piperidin-4-yl]]-(1H)-imidazo-(2,5-dihydro)rifamycin S Following the general procedure (B), the title compound was obtained as a pure solid. HRMS (ESI$^+$): 884.4048 (M+Na)$^+$; calculated for (M+Na)$^+$: 884.4058; RTI-083A, 1H-NMR (300 MHz, CDCl3): −0.04 (d, J=7 Hz, 3H), 0.61 (d, J=7 Hz, 3H), 0.84 (d, J=7 Hz, 3H), 1.04 (d, J=7 Hz, 3H), 1.20 (t, J=7 Hz, 3H), 1.4-1.6 (m, 2H), 1.65-1.85 (m, 3H), 1.74 (s, 3H), 1.95-2.2 (m, 2H), 2.02 (s, 3H), 2.04 (s, 3H), 2.35 (s, 3H), 2.40 (m, 1H), 3.00 (m, 1H), 3.09 (s, 3H), 3.3-3.4 (m, 3H), 3.43 (s, 1H), 3.56 (d, J=6 Hz, 1H), 3.68 (d, J=10 Hz, 1H), 3.7-4.0 (m, 4H), 4.50 (m, 1H), 4.72 (d, J=10 Hz, 1H), 5.13 (dd, J=12 and 7 Hz, 1H), 6.03 (dd, J=16 and 7 Hz, 1H), 6.18 (d, J=12 Hz, 1H), 6.27 (d, J=10 Hz, 1H), 6.38 (m, 1H), 8.18 (s, 1H), 8.90 (s, 1H), 14.57 (s, 1H).

Preparation of RTI-84 11-deoxy-11-imino-4-deoxy-3,4[2-spiro-[1-(isopropyloxycarbonyl)-piperidin-4-yl]]-(1H)-imidazo-(2,5-dihydro)rifamycin S Following the general procedure (A), the title compound was obtained as a pure solid. HRMS (ESI$^+$): 898.4203 (M+Na)$^+$; calculated for (M+Na)$^+$: 898.4215; RTI-084A, 1H-NMR (300 MHz, CDCl3): −0.09 (d, J=7 Hz, 3H), 0.61 (d, J=7 Hz, 3H), 0.84 (d, J=7 Hz, 3H), 1.04 (d, J=7 Hz, 3H), 1.30 (d, J=6 Hz, 6H), 1.44 (m, 1H), 1.6-1.85 (m, 4H), 1.88 (s, 3H), 1.9-2.15 (m, 2H), 2.02 (s, 3H), 2.05 (s, 3H), 2.35 (s, 3H), 2.40 (m, 1H), 3.00 (m, 1H), 3.09 (s, 3H), 3.33 (m, 1H), 3.50 (s, 1H), 3.61 (d, J=6 Hz, 1H), 3.68 (d, J=10 Hz, 1H), 3.6-3.8 (br, 2H), 4.0-4.2 (br, 2H), 4.72 (d, J=10 Hz, 1H), 4.99 (m, 1H), 5.07 (dd, J=12 and 7 Hz, 1H), 6.03 (dd, J=16 and 7 Hz, 1H), 6.16 (d, J=12 Hz, 1H), 6.28 (d, J=10 Hz, 1H), 6.40 (dd, J=16 and 10 Hz, 1H), 8.27 (s, 1H), 8.7 (bs, 1H), 12.93 (s, 1H), 14.21 (s, 1H).

Preparation of RTI-86 4-deoxy-3,4[2-spiro-[1-(phenylaminocarbonyl)-piperidin-4-yl]]-(1H)-imidazo-(2, 5-dihydro)rifamycin S Following the general procedure (B), the title compound was obtained as a pure solid. HRMS (ESI$^+$): 932.4038 (M+Na)$^+$; calculated for (M+Na)$^+$: 932.4058; RTI-086A, 1H-NMR (300 MHz, CDCl3): −0.02 (d, J=7 Hz, 3H), 0.62 (d, J=7 Hz, 3H), 0.84 (d, J=7 Hz, 3H), 1.04 (d, J=7 Hz, 3H), 1.4-1.6 (m, 2H), 1.65-1.85 (m, 3H), 1.75 (s, 3H), 1.95-2.2 (m, 3H), 2.02 (s, 3H), 2.05 (s, 3H), 2.35 (s, 3H), 3.00 (m, 1H), 3.09 (s, 3H), 3.3 (m, 1H), 3.45 (s, 1H), 3.58 (d, J=6 Hz, 1H), 3.67 (d, J=10 Hz, 1H), 3.8-4.2 (m, 4H), 4.72 (d, J=10 Hz, 1H), 5.13 (dd, J=12 and 7 Hz, 1H), 6.03 (dd, J=16 and 7 Hz, 1H), 6.18 (d, J=12 Hz, 1H), 6.27 (d, J=10 Hz, 1H), 6.38 (m, 1H), 6.44 (s, 1H), 7.10 (m, 1H), 7.37 (m, 4H), 8.21 (s, 1H), 8.88 (s, 1H), 14.56 (s, 1H).

Preparation of RTI-91 11-deoxy-11-imino-4-deoxy-3,4[2-spiro-[1-(3,3-dimethylbutanoyl)-piperidin-4-yl]]-(1H)-imidazo-(2,5-dihydro)rifamycin S Following the general procedure (A), the title compound was obtained as a pure solid. HRMS (ESI$^+$): 910.4589 (M+Na)$^+$; calculated for (M+Na)$^+$: 910.4579; RTI-91A, 1H-NMR (300 MHz, CDCl3): −0.07 (d, J=7 Hz, 3H), 0.61 (d, J=7 Hz, 3H), 0.85 (d, J=7 Hz, 3H), 1.05 (m, 3H), 1.10 (s, 9H), 1.45 (m, 1H), 1.6-1.85 (m, 4H), 1.88 (s, 3H), 2.02 (s, 3H), 2.05 (s, 3H), 2.0-2.2 (m, 2H), 2.35 (s, 3H), 2.3-2.45 (m, 3H), 3.00 (m, 1H), 3.09 (s, 3H), 3.33 (m, 1H), 3.47 (s, 0.4H), 3.52 (s, 0.6H), 3.55-3.70 (m, 3H), 3.8-4.0 (m, 2H), 4.5 (m, 1H), 4.75 (m, 1H), 5.06 (m, 1H), 6.0 (m, 1H), 6.17 (m, 1H), 6.29 (d, J=10 Hz, 1H), 6.4 (m, 1H), 8.27 (s, 1H), 8.63 (s, 0.6H), 8.71 (s, 0.4H), 12.92 (s, 1H), 14.16 (s, 0.4H), 14.20 (s, 0.6H).

Preparation of RTI-94 11-deoxy-11-imino-4-deoxy-3,4[2-spiro-[1-(n-pentanoyl)-piperidin-4-yl]]-(1H)-imidazo-(2,5-dihydro)rifamycin S Following the general procedure (A), the title compound was obtained as a pure solid. HRMS (ESI$^+$): 874.4644 (M+H)$^+$; calculated for (M+H)$^+$: 874.4604; RTI-94A, 1H-NMR (300 MHz, CDCl3): −0.07 (d, J=7 Hz, 3H), 0.61 (d, J=7 Hz, 3H), 0.84 (d, J=7 Hz, 3H), 0.97 (t, J=7 Hz, 3H), 1.04 (m, 3H), 1.42 (m, 3H), 1.6-1.85 (m, 6H), 1.88 (s, 3H), 2.02 (s, 3H), 2.05 (s, 3H), 1.9-2.2 (m, 2H), 2.35 (s, 3H), 2.3-2.45 (m, 3H), 3.00 (m, 1H), 3.09 (s, 3H), 3.33 (m, 1H), 3.49 (s, 0.4H), 3.53 (s, 0.6H), 3.55-3.70 (m, 3H), 3.8-4.0 (m, 2H), 4.5 (m, 1H), 4.72 (m, 1H), 5.06 (m, 1H), 6.0 (m, 1H), 6.17 (m, 1H), 6.29 (d, J=10 Hz, 1H), 6.4 (m, 1H), 8.29 (s, 1H), 8.63 (s, 0.6H), 8.70 (s, 0.4H), 12.92 (s, 1H), 14.17 (s, 0.4H), 14.20 (s, 0.6H).

Preparation of RTI-97 11-deoxy-11-imino-4-deoxy-3,4[2-spiro-[1-(2-methylpropanoyl)-piperidin-4-yl]]-(1H)-imidazo-(2,5-dihydro)rifamycin S Following the general procedure (A), the title compound was obtained as a pure solid. HRMS (ESI$^+$): 860.4482 (M+H)$^+$; calculated for (M+H)$^+$: 860.4447. RTI-97A, 1H-NMR (300 MHz, CDCl3): −0.07 (d, J=7 Hz, 3H), 0.61 (d, J=7 Hz, 3H), 0.84 (d, J=7 Hz, 3H), 1.04 (m, 3H), 1.20 (d, J=7 Hz, 6H), 1.43 (m, 1H), 1.6-1.85 (m, 4H), 1.88 (s, 3H), 2.02 (s, 3H), 2.05 (s, 3H), 2.0-2.2 (m, 2H), 2.35 (s, 3H), 2.40 (m, 1H), 2.89 (m, 1H), 3.01 (m, 1H), 3.09 (s, 3H), 3.33 (m, 1H), 3.47 (s, 0.4H), 3.50 (s, 0.6H), 3.55-3.70 (m, 3H), 3.8-4.1 (m, 2H), 4.5 (m, 1H), 4.72 (m, 1H), 5.06 (m, 1H), 6.01 (dd, J=15 and 6 Hz, 1H), 6.18 (d, J=12 Hz, 1H), 6.29 (d, J=10 Hz, 1H), 6.39 (m, 1H), 8.25 (s, 1H), 8.67 (s, 0.6H), 8.70 (s, 0.4H), 12.93 (s, 1H), 14.16 (s, 0.4H), 14.19 (s, 0.6H).

Preparation of RTI-98 11-deoxy-11-imino-4-deoxy-3,4[2-spiro-[1-(3-methylbutanoyl)-piperidin-4-yl]]-(1H)-imidazo-(2,5-dihydro)rifamycin S Following the general procedure (A), the title compound was obtained as a pure solid. HRMS (ESI⁺): 874.4632 (M+H)⁺; calculated for (M+H)⁺: 874.4604. RTI-98A, 1H-NMR (300 MHz, CDCl3): −0.07 (d, J=7 Hz, 3H), 0.61 (d, J=7 Hz, 3H), 0.84 (d, J=7 Hz, 3H), 1.04 (m, 3H), 1.02 (d, J=7 Hz, 6H), 1.43 (m, 1H), 1.6-1.85 (m, 4H), 1.88 (s, 3H), 2.02 (s, 3H), 2.05 (s, 3H), 2.0-2.2 (m, 3H), 2.30 (m, 3H), 2.35 (s, 3H), 2.40 (m, 1H), 3.00 (m, 1H), 3.09 (s, 3H), 3.33 (m, 1H), 3.47 (s, 0.4H), 3.50 (s, 0.6H), 3.55-3.70 (m, 3H), 3.8-4.0 (m, 2H), 4.5 (m, 1H), 4.72 (m, 1H), 5.06 (m, 1H), 6.01 (m, 1H), 6.17 (d, J=12 Hz, 0.6H), 6.18 (d, J=12 Hz, 0.4H), 6.29 (d, J=10 Hz, 1H), 6.40 (m, 1H), 8.24 (s, 1H), 8.65 (s, 0.6H), 8.72 (s, 0.4H), 12.92 (s, 1H), 14.16 (s, 0.4H), 14.19 (s, 0.6H).

Preparation of RTI-101 4-deoxy-3,4[2-spiro-[1-(dimethylaminocarbonyl)-piperidin-4-yl]]-(1H)-imidazo-(2,5-dihydro)rifamycin S Following the general procedure (B), the title compound was obtained as a pure solid. HRMS (ESI⁺): 884.4036 (M+Na)⁺; calculated for (M+Na)⁺: 884.4058; RTI-101, 1H-NMR (300 MHz, CDCl3): −0.04 (d, J=7 Hz, 3H), 0.61 (d, J=7 Hz, 3H), 0.84 (d, J=7 Hz, 3H), 1.04 (d, J=7 Hz, 3H), 1.44 (m, 1H), 1.6 (m, 1H), 1.65-1.90 (m, 3H), 1.75 (s, 3H), 1.95-2.2 (m, 2H), 2.01 (s, 3H), 2.04 (s, 3H), 2.35 (s, 3H), 2.40 (m, 1H), 2.90 (s, 6H), 3.00 (m, 1H), 3.09 (s, 3H), 3.33 (m, 1H), 3.42 (s, 1H), 3.57 (d, J=6 Hz, 1H), 3.6-3.8 (m, 5H), 4.72 (d, J=10 Hz, 1H), 5.14 (dd, J=12 and 7 Hz, 1H), 6.00 (dd, J=16 and 7 Hz, 1H), 6.18 (d, J=12 Hz, 1H), 6.27 (d, J=10 Hz, 1H), 6.37 (m, 1H), 8.19 (s, 1H), 8.96 (s, 1H), 14.62 (s, 1H).

Preparation of RTI-102 4-deoxy-3,4[2-spiro-[1-(isobutylaminocarbonyl)-piperidin-4-yl]]-(1H)-imidazo-(2,5-dihydro)rifamycin S Following the general procedure (B), the title compound was obtained as a pure solid. HRMS (ESI⁺): 912.4326 (M+Na)⁺; calculated for (M+Na)⁺: 912.4371; RTI-102, 1H-NMR (300 MHz, CDCl3): −0.04 (d, J=7 Hz, 3H), 0.61 (d, J=7 Hz, 3H), 0.84 (d, J=7 Hz, 3H), 0.95 (d, J=7 Hz, 6H), 1.04 (d, J=7 Hz, 3H), 1.44 (m, 1H), 1.6 (m, 1H), 1.65-1.90 (m, 4H), 1.75 (s, 3H), 1.95-2.2 (m, 2H), 2.02 (s, 3H), 2.05 (s, 3H), 2.35 (s, 3H), 2.40 (m, 1H), 3.00 (m, 1H), 3.09 (s, 3H), 3.12 (m, 2H), 3.33 (m, 1H), 3.45 (s, 1H), 3.58 (d, J=6 Hz, 1H), 3.65 (d, J=10 Hz, 1H), 3.7-4.0 (m, 4H), 4.62 (m, 1H), 4.73 (d, J=10 Hz, 1H), 5.13 (dd, J=12 and 7 Hz, 1H), 6.00 (dd, J=16 and 7 Hz, 1H), 6.18 (d, J=12 Hz, 1H), 6.27 (d, J=10 Hz, 1H), 6.38 (m, 1H), 8.20 (s, 1H), 8.89 (s, 1H), 14.58 (s, 1H).

Preparation of RTI-103 4-deoxy-3,4[2-spiro-[1-(isopropylaminocarbonyl)-piperidin-4-yl]]-(1H)-imidazo-(2,5-dihydro)rifamycin S Following the general procedure (B), the title compound was obtained as a pure solid. HRMS (ESI⁺): 898.4194 (M+Na)⁺; calculated for (M+Na)⁺: 898.4215; RTI-103, 1H-NMR (300 MHz, CDCl3): −0.04 (d, J=7 Hz, 3H), 0.61 (d, J=7 Hz, 3H), 0.84 (d, J=7 Hz, 3H), 1.04 (d, J=7 Hz, 3H), 1.21 (d, J=7 Hz, 6H), 1.44 (m, 1H), 1.55 (m, 1H), 1.65-1.90 (m, 3H), 1.75 (s, 3H), 2.0-2.15 (m, 2H), 2.02 (s, 3H), 2.05 (s, 3H), 2.35 (s, 3H), 2.40 (m, 1H), 3.00 (m, 1H), 3.09 (s, 3H), 3.33 (m, 1H), 3.45 (s, 1H), 3.58 (d, J=6 Hz, 1H), 3.66 (d, J=10 Hz, 1H), 3.7-4.0 (m, 4H), 4.03 (m, 1H), 4.33 (d, J=7 Hz, 1H), 4.73 (d, J=10 Hz, 1H), 5.13 (dd, J=12 and 7 Hz, 1H), 6.00 (dd, J=16 and 7 Hz, 1H), 6.18 (d, J=12 Hz, 1H), 6.27 (d, J=10 Hz, 1H), 6.38 (m, 1H), 8.20 (s, 1H), 8.89 (s, 1H), 14.59 (s, 1H).

Preparation of RTI-104 4-deoxy-3,4[2-spiro-[1-((1-methylpropyl)aminocarbonyl)-piperidin-4-yl]]-(1H)-imidazo-(2,5-dihydro)rifamycin S Following the general procedure (B), the title compound was obtained as a pure solid. HRMS (ESI⁺): 912.4337 (M+Na)⁺; calculated for (M+Na)⁺: 912.4371; RTI-104, 1H-NMR (300 MHz, CDCl3): −0.04 (d, J=7 Hz, 3H), 0.61 (d, J=7 Hz, 3H), 0.84 (d, J=7 Hz, 3H), 0.95 (t, J=7 Hz, 3H), 1.04 (d, J=7 Hz, 3H), 1.18 (d, J=7 Hz, 3H), 1.4-1.6 (m, 4H), 1.65-1.85 (m, 3H), 1.75 (s, 3H), 2.0-2.15 (m, 2H), 2.02 (s, 3H), 2.05 (s, 3H), 2.35 (s, 3H), 2.40 (m, 1H), 3.00 (m, 1H), 3.09 (s, 3H), 3.33 (m, 1H), 3.45 (s, 1H), 3.58 (d, J=6 Hz, 1H), 3.66 (d, J=10 Hz, 1H), 3.7-4.0 (m, 5H), 4.30 (d, J=8 Hz, 1H), 4.73 (d, J=10 Hz, 1H), 5.13 (dd, J=12 and 7 Hz, 1H), 6.00 (dd, J=16 and 7 Hz, 1H), 6.18 (d, J=12 Hz, 1H), 6.27 (d, J=10 Hz, 1H), 6.38 (m, 1H), 8.20 (s, 1H), 8.89 (s, 1H), 14.59 (s, 1H).

Preparation of RTI-105 4-deoxy-3,4[2-spiro-[1-(t-butylaminocarbonyl)-piperidin-4-yl]]-(1H)-imidazo-(2,5-dihydro)rifamycin S Following the general procedure (B), the title compound was obtained as a pure solid. HRMS (ESI⁺): 912.4333 (M+Na)⁺; calculated for (M+Na)⁺: 912.4371; RTI-105, 1H-NMR (300 MHz, CDCl3): −0.05 (d, J=7 Hz, 3H), 0.61 (d, J=7 Hz, 3H), 0.84 (d, J=7 Hz, 3H), 1.04 (d, J=7 Hz, 3H), 1.40 (s, 9H), 1.4-1.6 (m, 2H), 1.7-1.85 (m, 3H), 1.75 (s, 3H), 2.0-2.15 (m, 2H), 2.01 (s, 3H), 2.05 (s, 3H), 2.35 (s, 3H), 2.40 (m, 1H), 3.00 (m, 1H), 3.09 (s, 3H), 3.33 (m, 1H), 3.46 (s, 1H), 3.59 (d, J=6 Hz, 1H), 3.66 (d, J=10 Hz, 1H), 3.7-4.0 (m, 4H), 4.43 (s, 1H), 4.73 (d, J=10 Hz, 1H), 5.13 (dd, J=12 and 7 Hz, 1H), 6.00 (dd, J=16 and 7 Hz, 1H), 6.18 (d, J=12 Hz, 1H), 6.27 (d, J=10 Hz, 1H), 6.38 (m, 1H), 8.22 (s, 1H), 8.87 (s, 1H), 14.60 (s, 1H).

Preparation of RTI-175 11-deoxy-11-hydroxy-4-deoxy-3,4[2-spiro-[1-(isobutyloxycarbonyl)-piperidin-4-yl]]-(1H)-imidazo-(2,5-dihydro)rifamycin S Following the general procedure (C), the title compound was obtained as a pure solid. HRMS (ESI⁺): 915.4334 (M+Na)⁺; calculated for (M+Na)⁺: 915.4368; RTI-175, 1H-NMR (300 MHz, CDCl3): 0.05 (d, J=7 Hz, 3H), 0.63 (d, J=7 Hz, 3H), 0.85 (d, J=7 Hz, 3H), 0.96 (d, J=7 Hz, 6H), 1.04 (d, J=7 Hz, 3H), 1.40-1.60 (m, 2H), 1.7-2.1 (m, 6H), 1.93 (s, 3H), 2.05 (s, 3H), 2.07 (s, 3H), 2.24 (s, 3H), 2.40 (m, 1H), 3.00 (m, 1H), 3.07 (s, 3H), 3.48 (m, 1H), 3.68 (s, 1H), 3.5-3.8 (m, 2H), 3.86 (d, J=6 Hz, 2H), 3.85-4.1 (m, 4H), 4.95 (dd, J=12 and 4 Hz, 1H), 5.05 (d, J=10 Hz, 1H), 5.54 (s, 1H), 5.99 (d, J=12 Hz, 1H), 6.16 (dd, J=16 and 6 Hz, 1H), 6.27 (d, J=10 Hz, 1H), 6.44 (dd, J=16 and 10 Hz, 1H), 6.72 (s, 1H), 8.07 (s, 1H), 8.22 (bs, 1H), 13.61 (s, 1H).

Preparation of RTI-176 11-deoxy-11-amino-4-deoxy-3,4[2-spiro-[1-(isobutyloxycarbonyl)-piperidin-4-yl]]-(1H)-imidazo-(2,5-dihydro)rifamycin S Following the general procedure (C), the title compound was obtained as a pure solid. HRMS (ESI⁺): 892.4689

(M+H)⁺; calculated for (M+H)⁺: 892.4710; RTI-176 (RTI2-63B, 1H-NMR (300 MHz) (CDCl3): −0.05 (d, J=7 Hz, 3H), 0.64 (d, J=7 Hz, 3H), 0.85 (d, J=7 Hz, 3H), 0.96 (d, J=7 Hz, 6H), 1.04 (d, J=7 Hz, 3H), 1.40-1.70 (m, 2H), 1.7-1.9 (m, 4H), 1.9-2.1 (m, 2H), 1.94 (s, 3H), 2.05 (s, 3H), 2.08 (s, 3H), 2.24 (s, 3H), 2.40 (m, 1H), 2.6-2.8 (br, 2H), 3.03 (m, 1H), 3.07 (s, 3H), 3.52 (m, 1H), 3.67 (s, 1H), 3.6-3.7 (m, 2H), 3.80 (d, J=10 Hz, 1H), 3.91 (d, J=6 Hz, 2H), 3.85-4.1 (m, 2H), 4.11 (d, J=4 Hz, 1H), 4.77 (s, 1H), 4.87 (dd, J=12 and 4 Hz, 1H), 5.09 (d, J=10 Hz, 1H), 5.98 (d, J=12 Hz, 1H), 6.18 (dd, J=16 and 6 Hz, 1H), 6.25 (d, J=10 Hz, 1H), 6.44 (dd, J=16 and 11 Hz, 1H), 8.19 (s, 1H), 8.24 (bs, 1H), 13.93 (s, 1H).

Preparation of RTI-181 11-deoxy-11-amino-4-deoxy-3,4[2-spiro-[1-(2-methylpropyl)-piperidin-4-yl]]-(1H)-imidazo-(2,5-dihydro)rifamycin S Following the general procedure (C), the title compound was obtained as a pure solid. HRMS (ESI⁺): 848.4777 (M+H)⁺; calculated for (M+H)⁺: 848.4811; RTI-181, 1H-NMR (300 MHz, CDCl3): −0.05 (d, J=7 Hz, 3H), 0.63 (d, J=7 Hz, 3H), 0.85 (d, J=7 Hz, 3H), 0.92 (d, J=6 Hz, 6H), 1.04 (d, J=7 Hz, 3H), 1.40-1.50 (m, 1H), 1.7-2.1 (m, 9H), 1.94 (s, 3H), 2.05 (s, 3H), 2.07 (s, 3H), 2.23 (s, 3H), 2.24 (m, 2H), 2.40 (m, 1H), 2.6-2.8 (m, 4H), 3.03 (m, 1H), 3.07 (s, 3H), 3.50 (m, 1H), 3.68 (s, 1H), 3.80 (d, J=10 Hz, 1H), 4.11 (d, J=4 Hz, 1H), 4.76 (s, 1H), 4.87 (dd, J=12 and 4 Hz, 1H), 5.09 (d, J=10 Hz, 1H), 5.98 (d, J=12 Hz, 1H), 6.18 (dd, J=16 and 6 Hz, 1H), 6.25 (d, J=10 Hz, 1H), 6.44 (dd, J=16 and 11 Hz, 1H), 8.27 (s, 1H), 8.32 (s, 1H), 14.03 (s, 1H).

Preparation of RTI-182 11-deoxy-11-imino-4-deoxy-3,4[2-spiro-[1-(isobutylaminocarbonyl)-piperidin-4-yl]]-(1H)-imidazo-(2,5-dihydro)rifamycin S Following the general procedure (A), the title compound was obtained as a pure solid. HRMS (ESI⁺): 889.4678 (M+H)⁺; calculated for (M+H)⁺: 889.4713; RTI-182, 1H-NMR (300 MHz, CDCl3): −0.08 (d, J=7 Hz, 3H), 0.61 (d, J=7 Hz, 3H), 0.84 (d, J=7 Hz, 3H), 0.96 (d, J=7 Hz, 6H), 1.04 (d, J=7 Hz, 3H), 1.4 (m, 1H), 1.65 (m, 1H), 1.7-1.85 (m, 4H), 1.88 (s, 3H), 1.95-2.15 (m, 2H), 2.02 (s, 3H), 2.05 (s, 3H), 2.34 (s, 3H), 2.40 (m, 1H), 3.00 (m, 1H), 3.09 (s, 3H), 3.12 (m, 2H), 3.33 (m, 1H), 3.50 (s, 1H), 3.62 (d, J=5 Hz, 1H), 3.67 (d, J=9 Hz, 1H), 3.6-3.7 (m, 2H), 3.8-4.0 (m, 2H), 4.62 (t, J=5 Hz, 1H), 4.72 (d, J=10 Hz, 1H), 5.06 (dd, J=12 and 7 Hz, 1H), 6.02 (dd, J=15 and 7 Hz, 1H), 6.16 (d, J=12 Hz, 1H), 6.29 (d, J=10 Hz, 1H), 6.38 (m, 1H), 8.27 (s, 1H), 8.67 (s, 1H), 12.92 (s, 1H), 14.58 (s, 1H).

Preparation of RTI-183 11-deoxy-11-amino-4-deoxy-3,4[2-spiro-[1-(isobutylaminocarbonyl)-piperidin-4-yl]]-(1H)-imidazo-(2,5-dihydro)rifamycin S Following the general procedure (C), the title compound was obtained as a pure solid. HRMS (ESI⁺): 891.4843 (M+H)⁺; calculated for (M+H)⁺: 891.4870; RTI-183, 1H-NMR (300 MHz, CDCl3): −0.05 (d, J=7 Hz, 3H), 0.64 (d, J=7 Hz, 3H), 0.85 (d, J=7 Hz, 3H), 0.94 (d, J=7 Hz, 6H), 1.04 (d, J=7 Hz, 3H), 1.48 (m, 1H), 1.7-1.89 (m, 8H), 1.94 (s, 3H), 2.01 (m, 1H), 2.04 (s, 3H), 2.08 (s, 3H), 2.24 (s, 3H), 2.40 (m, 1H), 3.03 (m, 1H), 3.07 (s, 3H), 3.09 (m, 2H), 3.52 (m, 1H), 3.55-3.75 (m, 3H), 3.75 (s, 1H), 3.81 (d, J=10 Hz, 1H), 3.85-4.0 (m, 1H), 4.13 (d, J=4 Hz, 1H), 4.62 (t, J=5 Hz, 1H), 4.77 (s, 1H), 4.88 (dd, J=12 and 4 Hz, 1H), 5.09 (d, J=10 Hz, 1H), 5.98 (d, J=12 Hz, 1H), 6.18 (dd, J=16 and 6 Hz, 1H), 6.26 (d, J=10 Hz, 1H), 6.44 (dd, J=16 and 11 Hz, 1H), 8.20 (s, 1H), 8.35 (s, 1H), 13.94 (s, 1H).

Preparation of RTI-75 4-deoxy-3,4[2-spiro-[1-(t-butyloxycarbonyl)-piperidin-4-yl]]-(1H)-imidazo-(2,5-dihydro)rifamycin S Following the general procedure (B), the title compound was obtained as a pure solid. HRMS (ESI⁺): 913.4267 (M+Na)⁺; calculated for (M+Na)⁺: 913.4211; RTI-75A, 1H-NMR (300 MHz, CDCl3): −0.04 (d, J=7 Hz, 3H), 0.61 (d, J=7 Hz, 3H), 0.84 (d, J=7 Hz, 3H), 1.04 (d, J=7 Hz, 3H), 1.40-1.60 (m, 2H), 1.51 (s, 9H), 1.7-1.85 (m, 3H), 1.75 (s, 3H), 1.9-2.1 (m, 2H), 2.02 (s, 3H), 2.05 (s, 3H), 2.35 (s, 3H), 2.40 (m, 1H), 3.00 (m, 1H), 3.09 (s, 3H), 3.33 (m, 1H), 3.43 (s, 1H), 3.57 (d, J=5 Hz, 1H), 3.67 (d, J=10 Hz, 1H), 3.6-3.8 (br, 2H), 3.9-4.1 (br, 2H), 4.72 (d, J=10 Hz, 1H), 5.13 (dd, J=12 and 7 Hz, 1H), 6.02 (dd, J=16 and 7 Hz, 1H), 6.18 (d, J=12 Hz, 1H), 6.28 (d, J=10 Hz, 1H), 6.40 (dd, J=16 and 10 Hz, 1H), 8.19 (s, 1H), 8.93 (bs, 1H), 14.59 (s, 1H).

Preparation of RTI-76 4-deoxy-3,4[2-spiro-[1-(ethyloxycarbonyl)-piperidin-4-yl]]-(1H)-imidazo-(2,5-dihydro)rifamycin S Following the general procedure (B), the title compound was obtained as a pure solid. HRMS (ESI⁺): 885.3945 (M+Na)⁺; calculated for (M+Na)⁺ 885.3898; RTI-76A, 1H-NMR (300 MHz, CDCl3): −0.04 (d, J=7 Hz, 3H), 0.61 (d, J=7 Hz, 3H), 0.84 (d, J=7 Hz, 3H), 1.04 (d, J=7 Hz, 3H), 1.30 (t, J=7 Hz, 3H), 1.40-1.60 (m, 2H), 1.7-1.85 (m, 3H), 1.75 (s, 3H), 1.9-2.1 (m, 2H), 2.02 (s, 3H), 2.05 (s, 3H), 2.35 (s, 3H), 2.40 (m, 1H), 3.00 (m, 1H), 3.09 (s, 3H), 3.33 (m, 1H), 3.44 (s, 1H), 3.57 (d, J=5 Hz, 1H), 3.66 (d, J=10 Hz, 1H), 3.7-3.9 (br, 2H), 4.0-4.2 (br, 2H), 4.21 (q, J=7 Hz, 2H), 4.72 (d, J=10 Hz, 1H), 5.13 (dd, J=12 and 7 Hz, 1H), 6.00 (dd, J=16 and 7 Hz, 1H), 6.18 (d, J=12 Hz, 1H), 6.27 (d, J=10 Hz, 1H), 6.40 (dd, J=16 and 10 Hz, 1H), 8.20 (s, 1H), 8.92 (bs, 1H), 14.58 (s, 1H).

Preparation of RTI-78 4-deoxy-3,4[2-spiro-[1-(n-propyloxycarbonyl)-piperidin-4-yl]]-(1H)-imidazo-(2, 5-dihydro)rifamycin S Following the general procedure (B), the title compound was obtained as a pure solid. HRMS (ESI⁺): 899.3989 (M+Na)⁺; calculated for (M+Na)⁺ 899.4054; RTI-78A, 1H-NMR (300 MHz, CDCl3): −0.04 (d, J=7 Hz, 3H), 0.61 (d, J=7 Hz, 3H), 0.84 (d, J=7 Hz, 3H), 0.99 (t, J=7 Hz, 3H), 1.04 (d, J=7 Hz, 3H), 1.40-1.60 (m, 2H), 1.69 (m, 2H), 1.7-1.85 (m, 3H), 1.75 (s, 3H), 1.95-2.1 (m, 2H), 2.02 (s, 3H), 2.05 (s, 3H), 2.35 (s, 3H), 2.40 (m, 1H), 3.00 (m, 1H), 3.09 (s, 3H), 3.33 (m, 1H), 3.42 (s, 1H), 3.56 (d, J=5 Hz, 1H), 3.66 (d, J=10 Hz, 1H), 3.7-3.9 (br, 2H), 4.0-4.2 (br, 2H), 4.11 (t, J=7 Hz, 2H), 4.72 (d, J=10 Hz, 1H), 5.13 (dd, J=12 and 7 Hz, 1H), 6.00 (dd, J=16 and 7 Hz, 1H), 6.18 (d, J=12 Hz, 1H), 6.27 (d, J=10 Hz, 1H), 6.40 (dd, J=16 and 10 Hz, 1H), 8.17 (s, 1H), 8.92 (bs, 1H), 14.57 (s, 1H).

Preparation of RTI-79 4-deoxy-3,4[2-spiro-[1-(isobutyloxycarbonyl)-piperidin-4-yl]]-(1H)-imidazo-(2, 5-dihydro)rifamycin S Following the general procedure (B), the title compound was obtained as a pure solid. HRMS (ESI⁺): 913.4163 (M+Na)⁺; calculated for (M+Na)⁺ 913.4211; RTI-79A, 1H-NMR (300 MHz, CDCl3): −0.03 (d, J=7 Hz, 3H), 0.61

(d, J=7 Hz, 3H), 0.84 (d, J=7 Hz, 3H), 0.97 (d, J=7 Hz, 6H), 1.04 (d, J=7 Hz, 3H), 1.40-1.60 (m, 2H), 1.7-1.85 (m, 3H), 1.75 (s, 3H), 1.9-2.1 (m, 3H), 2.02 (s, 3H), 2.05 (s, 3H), 2.35 (s, 3H), 2.40 (m, 1H), 3.00 (m, 1H), 3.09 (s, 3H), 3.33 (m, 1H), 3.42 (s, 1H), 3.56 (d, J=5 Hz, 1H), 3.66 (d, J=10 Hz, 1H), 3.7-3.9 (br, 2H), 3.93 (d, J=6 Hz, 2H), 4.0-4.2 (br, 2H), 4.72 (d, J=10 Hz, 1H), 5.13 (dd, J=12 and 7 Hz, 1H), 6.00 (dd, J=16 and 7 Hz, 1H), 6.19 (d, J=12 Hz, 1H), 6.27 (d, J=10 Hz, 1H), 6.39 (dd, J=16 and 10 Hz, 1H), 8.17 (s, 1H), 8.93 (bs, 1H), 14.57 (s, 1H).

Preparation of RTI-80 4-deoxy-3,4[2-spiro-[1-(beR-TIyloxycarbonyl)-piperidin-4-yl]]-(1H)-imidazo-(2,5-dihydro)rifamycin S Following the general procedure (B), the title compound was obtained as a pure solid. HRMS (ESI+): 947.3987 (M+Na)+; calculated for (M+Na)+ 947.4054; RTI-80A, 1H-NMR (300 MHz, CDCl3): −0.04 (d, J=7 Hz, 3H), 0.61 (d, J=7 Hz, 3H), 0.84 (d, J=7 Hz, 3H), 1.04 (d, J=7 Hz, 3H), 1.40-1.60 (m, 2H), 1.7-1.85 (m, 3H), 1.74 (s, 3H), 1.9-2.1 (m, 2H), 2.01 (s, 3H), 2.04 (s, 3H), 2.35 (s, 3H), 2.40 (m, 1H), 3.00 (m, 1H), 3.09 (s, 3H), 3.33 (br, 1H), 3.42 (br, 1H), 3.56 (d, J=5 Hz, 1H), 3.66 (d, J=10 Hz, 1H), 3.7-3.9 (br, 2H), 4.0-4.2 (br, 2H), 4.72 (d, J=10 Hz, 1H), 5.13 (dd, J=12 and 7 Hz, 1H), 5.20 (m, 2H), 6.00 (dd, J=16 and 7 Hz, 1H), 6.18 (d, J=12 Hz, 1H), 6.27 (d, J=10 Hz, 1H), 6.39 (dd, J=16 and 10 Hz, 1H), 7.39 (m, 5H), 8.16 (s, 1H), 8.93 (bs, 1H), 14.57 (s, 1H).

Preparation of RTI-174 11-deoxy-11-hydroxy-4-deoxy-3,4[2-spiro-[1-(2-methylpropyl)-piperidin-4-yl]]-(1H)-imidazo-(2,5-dihydro)rifamycin S Following the general procedure (C), the title compound was obtained as a pure solid. HRMS (ESI+): 871.4433 (M+Na)+; calculated for (M+Na)+ 871.4470.

Preparation of RTI-197 11-deoxy-11-hydroxyimino-4-deoxy-3,4[2-spiro-[1-(isobutyloxycarbonyl)-piperidin-4-yl]]-(1H)-imidazo-(2,5-dihydro)rifamycin S Following the general procedure (D), the title compound was obtained as a solid. HRMS (ESI+): 906.4535 (M+H)+; calculated for (M+H)+ 906.4535; RTI-197, 1H-NMR (300 MHz, CDCl3): −0.03 (d, J=7 Hz, 3H), 0.62 (d, J=7 Hz, 3H), 0.84 (d, J=7 Hz, 3H), 0.97 (d, J=7 Hz, 6H), 1.04 (d, J=7 Hz, 3H), 1.35-1.40 (m, 1H), 1.7-1.8 (m, 1H), 1.85-2.1 (m, 6H), 2.00 (s, 3H), 2.04 (s, 3H), 2.13 (s, 3H), 2.33 (s, 3H), 2.40 (m, 1H), 3.00 (m, 1H), 3.10 (s, 3H), 3.34 (m, 1H), 3.42-3.50 (m, 2H), 3.67 (d, J=10 Hz, 1H), 3.8-3.9 (m, 4H), 3.93 (d, J=6 Hz, 2H), 4.60 (d, J=10 Hz, 1H), 5.23 (dd, J=12 and 8 Hz, 1H), 5.98 (dd, J=15 and 6 Hz, 1H), 6.30 (d, J=12 Hz, 2H), 6.40 (dd, J=16 and 10 Hz, 1H), 8.35 (s, 1H), 8.92 (bs, 1H), 14.13 (s, 1H).

Preparation of RTI-217 11-deoxy-11-hydroxyimino-4-deoxy-3,4[2-spiro-[1-(isobutylaminocarbonyl)-piperidin-4-yl]]-(1H)-imidazo-(2,5-dihydro)rifamycin S Following the general procedure (D), the title compound was obtained as a solid. HRMS (ESI+): 905.4695 (M+H)+; calculated for (M+H)+ 905.4662; RTI-217, 1H-NMR (300 MHz, CDCl3): −0.03 (d, J=7 Hz, 3H), 0.62 (d, J=7 Hz, 3H), 0.84 (d, J=7 Hz, 3H), 0.95 (d, J=7 Hz, 6H), 1.04 (d, J=7 Hz, 3H), 1.35-1.40 (m, 1H), 1.7-1.8 (m, 1H), 1.85-2.1 (m, 6H), 2.00 (s, 3H), 2.04 (s, 3H), 2.13 (s, 3H), 2.33 (s, 3H), 2.40 (m, 1H), 3.00 (m, 1H), 3.10 (s, 3H), 3.08-3.14 (m, 2H), 3.34 (m, 1H), 3.45 (s, 1H), 3.47 (d, J=6 Hz, 1H), 3.65-3.8 (m, 5H), 4.60 (m, 2H), 5.23 (dd, J=12 and 8 Hz, 1H), 5.98 (dd, J=16 and 7 Hz, 1H), 6.30 (d, J=12 Hz, 2H), 6.40 (dd, J=16 and 10 Hz, 1H), 8.34 (s, 1H), 8.89 (s, 1H), 14.14 (s, 1H).

Example 13: Preparation of a Rifabutin Derivative Modified on Alternative Sites

Biotin-glycine-substituted rifabutin derivative RTI-173 contains a substitution at the 21-hydroxy site, yet has a similar activity as rifabutin on G3 cells when combined with doxorubicin, suggesting that this site may be modified without affecting drug-sensitization or cancer inhibition effects. Biotin-glycine-linked rifabutin derivative (RTI-173) has the following formula:

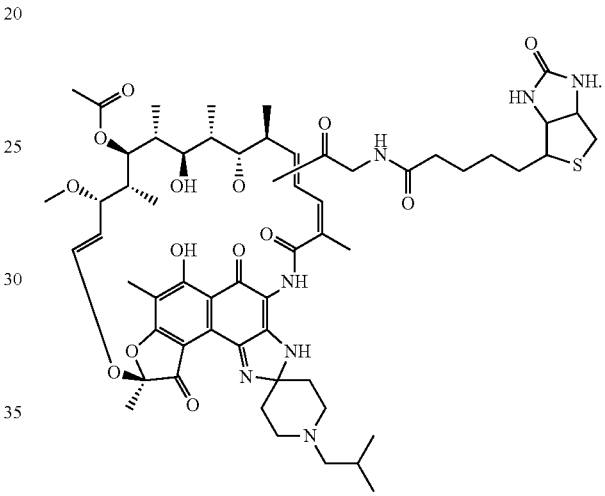

RTI-173

RTI-173 was prepared by the following method:

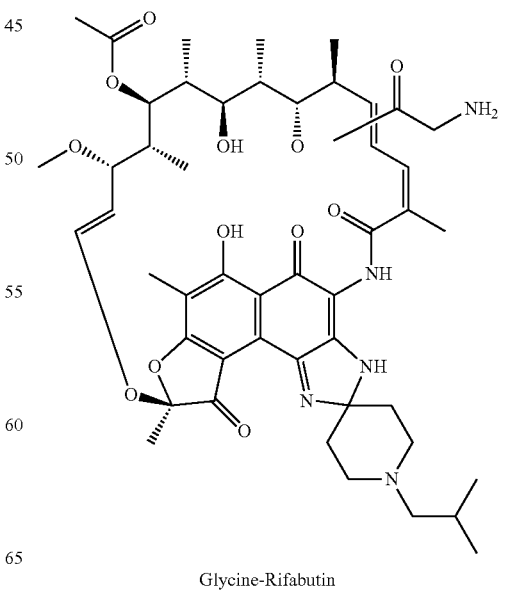

Glycine-Rifabutin

+

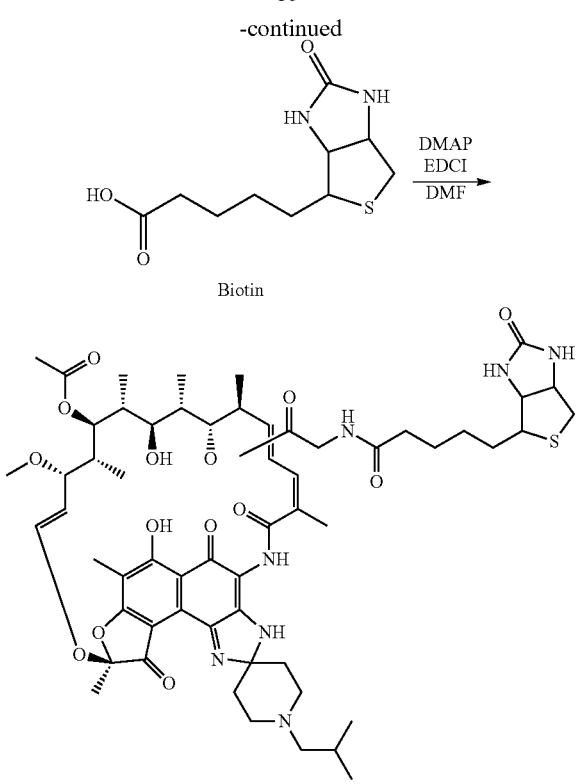

A solution of Glycine-rifabutin (240 mg, 0.27 mmole) in DMF (2 ml) was added to a solution of biotin (65 mg, 0.27 mmol), DMAP (33 mg, 0.27 mmol) and EDCI (52 mg, 0.27 mmole) in DMF (3 ml) at room temperature. The reaction mixture stirred at room temperature overnight and diluted with DCM (40 ml) and washed with water and brine. The organic phase was dried over anhydrous sodium sulphate, filtered and concentrated under vacuum. The residue was purified by silica gel column chromatography with methanol in DCM as eluent to give 108 mg of the product as purple solid. HRMS (ESI$^+$): 1152.5538 (M+Na)$^+$; calculated for (M+Na)$^+$ 1152.5304.

Example 14: Example Rifabutin and Rifabutin Derivative Compositions and Methods of Administration to a Chemotherapeutic-Resistant Cancer Patient Rifamycin and rifamycin derivatives, such as rifabutin and rifabutin derivative compositions may be prepared as described herein. Compositions formulated in the same ways as rifabutin, rifamycin, or related drugs typically currently formulated may be useful for administration to cancer patients. These compositions may contain rifamycin, a rifamycin derivative, rifabutin, or a rifabutin derivative, such as the RTI-79 derivative described herein.

In particular, compositions may be formulated in tablets or capsules for oral use. These tablets or capsules may be extended release tablets or capsules to provide a more stable and continuous supply of the rifamycin or rifamycin derivative to the cancer cells in the patient. Tablets or capsules may contain at least 10 mg, at least 50 mg, at least 100 mg, at least 150 mg, or at least 200 mg of rifamycin or rifamycin derivative. Combination tablets or capsules with other drugs, such as chemotherapeutic drugs or other drugs commonly administered with chemotherapy may be prepared, particularly if the recommended dosing schedule for those drugs is similar to that of the rifamycin or rifamycin derivative. For example, the rifamycin or rifamycin derivative may be combined with the prednisone portion of CHOP therapy or another steroid or other drug that is intended to be administered daily.

Compositions may also be formulated for intravenous injection as well. In general, the amount of rifamycin or rifamycin derivative, such as rifabutin or a rifabutin derivative, may be lower in a dose formulated for intravenous injection than in a dose formulated for oral administration because intravenous injection avoids the need for absorption through the intestines. Injectable doses of rifamycin or rifamycin derivative, including rifabutin or a rifabutin derivative, may be provided in multi-use containers or in single-use containers. These containers may be compatible for use with standard intravenous needles and syringes as well as intravenous drip systems and more complex chemotherapeutic administration systems. Single-use containers may contain the entire amount of rifamycin or rifamycin derivative administered with a round a chemotherapy to avoid the need for multiple injections of the drug. Alternatively, they may contain amounts appropriate for daily doses. Single-use containers may contain at least 1 mg, at least 5 mg, at least 10 mg, at least 50 mg, at least 100 mg, or at least 150 mg of rifamycin or rifamycin derivative. Multi-use containers may be designed to allow administration of these same amounts of rifamycin or rifamycin derivative. Injectable compositions may further contain other injectable chemotherapeutic drugs or other drugs commonly administered with chemotherapy. In one specific example, injectable compostions may contain doxorubicin or a similar chemotherapeutic in a liposome. In such compositions, the rifamycin or rifamycin derivate may also be in the liposome. In general, due to improvements in delivery via liposomes, if the rifamycin or rifamycin derivative is contained in a liposome, the total amount in the dose may be less than if the rifamycin or rifamycin derivative is injectable, but not in a liposome.

Rifamycin and rifamycin derivatives, such as rifabutin and rifabutin derivatives may be administered to patients with cancer in the form of any compositions described in this example or elsewhere herein or any other form. The patients with cancer may have a cancer that is resistant to one or more chemotherapeutics, may be at risk for developing cancer resistant to one or more chemotherapeutics, may benefit from administration of reduced amounts of one or more chemotherapeutics, or may benefit from the administration of a particular chemotherapeutic to which rifamycin or a rifamycin derivative sensitizes the patient's cancer cells.

In one example, the rifamycin or rifamycin derivates may be administered orally to patients with cancer. In particular, they may be administered in the form of tablets or capsules. The rifamycin or rifamycin derivative may be administered such that the patient receives at least 50 mg/adult human/week, at least 100 mg/adult human/week, at least 150 mg/adult human/week, or at least 300 mg/adult human/week. Amounts may be reduced for children. For example, a child under age 5 might receive one quarter or less of an adult human dose. A child age 5 to age 10 may receive one half to one quarter the adult human dose. A child age 10 or over may receive three quarters to one half the adult human dose. In another embodiment, the rifamycin or rifamycin derivative may be administered such that the patient receives at least 0.5 mg/kg/week, at least 1 mg/kg/week, at least 2 mg/kg/week, at least 5 mg/kg/week, at least 10 mg/kg/week, at least 20 mg/kg/week, at least 30 mg/kg/week, at least 50 mg/kg/week or at least 100 mg/kg/week.

Rifamycin or a rifamycin derivative administered orally in this fashion may be administered weekly, daily, or multiple times per day. The dosing schedule may be adjusted so as to maintain minimal blood concentrations for a period of time, particularly with extended release formulations. Alternatively, maintenance of minimal blood concentrations may not be necessary for some methods of treatment and dosing may instead be designed to achieve a total blood concentration for a shorter period of time, such as for four hours or less. Although amounts are expressed as weekly totals, it will be understood that the compositions do not have to be administered for a full week. For example, a patient may receive a single dose in connection with a chemotherapeutic treatment and may not receive a further dose until much later, with another chemotherapeutic treatment, or not at all. Furthermore, it is possible to administer the weekly total through various combinations of doses on various days. For example, it may be possible to administer doses only every other day or every few days. Doses also need not be the same each day. For example, a patient may receive doses that increase or decrease over time, particularly due to the schedule for administration of chemotherapeutics. In one example, the patient may be provided with a pack of varying-dose tablets or capsules labeled by day (e.g. Day 1, Day 2, etc.), by portions of the day (e.g. Day 1 morning, Day 1 evening, etc.), or by week (e.g. Week 1, Week 2, etc.) and instructed to begin taking the tablets or capsules at a specified time dictated by the schedule for administration of a chemotherapeutic.

In general, the rifamycin or rifamycin derivative may be administered in connection with administration of a chemotherapeutic. In one example, it may be administered at least weekly or at least daily the entire time the patient is receiving a course of a chemotherapeutic, such as for several months. In another example it may be administered only to coincide with administration of a chemotherapeutic, such as for one day to one week each month coinciding with a once monthly chemotherapeutic administration.

In one specific example, the rifamycin or rifamycin derivative may be rifabutin or RTI-79 administered orally in one to three doses of rifabutin or RTI-79 in 100 mg to 300 mg amounts over a period of up to 48 hours beginning within 24 hours before or after the administration of a chemotherapeutic, such as DOXIL®. A single oral dose of 300 mg rifabutin causes a mean (±SD) peak plasma concentration (Cmax) of 375 (±267) ng/mL (range 141 to 1033 ng/mL). The plasma elimination of rifabutin is biphasic with an initial half-life of approximately 4 hours, followed by a mean terminal half-life of 45 (±17) hours (range 16 to 69 hours). The rifabutin derivative RTI-79 is expected to present similar results. Accordingly, appropriate dosages for variations of this example using intravenously injected rifabutin or RTI-79 rather than orally administered forms may be calculated.

In an alternative embodiment, rifamycin or a rifamycin derivative, such as rifabutin or RTI-79, may be administered in a method that matches the pharmokinetics of the rifamycin or rifamycin derivative to that of the chemotherapeutic also administered to the patient. For example, maximal doxorubicin tissue absorption occurs 48 hours after administration. Maximal RTI-79 plasma concentration is reached within 3 hours of administration. Accordingly, administrating RTI-79 orally 24 and 48 hours after intravenous doxorubicin administration may maximize efficacy.

In another alternative embodiment, rifamycin or a rifamycin derivative, such as rifabutin or RTI-79, may be administered in amounts similar to those described herein after the cessation of chemotherapy to reduce or prevent metastasis.

Although only exemplary embodiments of the invention are specifically described above, it will be appreciated that modifications and variations of these examples are possible without departing from the spirit and intended scope of the invention. For example, various specific formulations including components not listed herein and specific methods of administering such formulations may be developed using the ordinary skill in the art. Numeric amounts expressed herein will be understood by one of ordinary skill in the art to include amounts that are approximately or about those expressed. Furthermore, the term "or" as used herein is not intended to express exclusive options (either/or) unless the context specifically indicates that exclusivity is required; rather "or" is intended to be inclusive (and/or).

The invention claimed is:

1. A method of increasing reactive oxygen species (ROS) in a cancer cell comprising administering rifamycin or rifabutin to the cancer cell in an amount and for a time sufficient to increase ROS in the cancer cell.

2. The method according to claim 1, wherein the ROS comprises a superoxide.

3. A method of increasing susceptibility of a cancer cell to a drug comprising:
   administering rifamycin or rifabutin to the cancer cell in an amount and for a time sufficient to increase reactive oxygen species (ROS) in the cancer cell; and
   administering the drug to the cancer cell in an amount and for a time sufficient to inhibit the cancer cell, wherein the amount or time are less than that required to achieve the same inhibition in the absence of increased ROS.

4. The method of claim 3, wherein the ROS comprises superoxide.

5. The method of claim 3, wherein the drug comprises a chemotherapeutic.

6. The method of claim 3, wherein the cancer cell comprises a cancer cell resistant to the drug.

7. The method of claim 1, further comprising administering the rifamycin or rifabutin to the cancer cell a second or greater time.

8. The method of claim 1, wherein the cancer cell is a carcinoma, a sarcoma, a leukemia, a lymphoma, or a glioma.

9. The method of claim 1, further comprising administering a superoxide dismutase inhibitor to the cancer cell in an amount and for a time sufficient to further increase ROS in the cancer cell.

10. The method of claim 1, further comprising administering an apoptotic pathway inhibitor to the cancer cell.

11. The method of claim 1, further comprising administering a chemotherapeutic to the cancer cell.

12. The method of claim 3, further comprising administering rifamycin or rifabutin to the cancer cell before the drug.

13. The method of claim 3, further comprising administering rifamycin or rifabutin to the cancer cell concurrently with the drug.

14. The method of claim 3, further comprising administering rifamycin or rifabutin to the cancer cell after the drug.

15. The method of claim 3, further comprising administering the rifamycin or rifabutin to the cancer cell a second or greater time.

16. The method of claim 3, wherein the cancer cell is a carcinoma, a sarcoma, as leukemia, a lymphoma, or a glioma.

17. The method of claim 3, wherein the cancer cell is a metastatic cancer cell.

18. The method of claim 3, further comprising administering a superoxide dismutase inhibitor to the cancer cell in an amount and for a time sufficient to further increase ROS in the cancer cell.

19. The method of claim 3, further comprising administering an apoptotic pathway inhibitor to the cancer cell.

20. The method of claim 1, wherein the cancer cell is a metastatic cancer cell.

* * * * *